United States Patent [19]

Sass et al.

[11] Patent Number: 5,477,001
[45] Date of Patent: Dec. 19, 1995

[54] RECOMBINANT DNA CODING FOR A NOVEL PROTEIN HAVING β-1,3-GLUCANASE ACTIVITY, BACTERIA CONTAINING THIS DNA, TRANSFORMED PLANT CELLS AND PLANTS

[75] Inventors: Catherine Sass, Verdun, Canada; Jean-Jacques Leguay, Paris, France; René Grison, Escalquens, France; Alain Toppan, Cornebarrieu, France

[73] Assignees: Elf Sanofi, Paris; Societe Nationale Elf Aquitaine, Courbevoie, both of France

[21] Appl. No.: 966,187
[22] PCT Filed: Mar. 25, 1992
[86] PCT No.: PCT/FR92/00268
 § 371 Date: Jan. 25, 1993
 § 102(e) Date: Jan. 25, 1993
[87] PCT Pub. No.: WO92/16632
 PCT Pub. Date: Oct. 10, 1992

[30] Foreign Application Priority Data

Mar. 25, 1991 [FR] France ................... 91 03588

[51] Int. Cl.⁶ ............................. A01H 5/00; C12N 9/24; C12N 15/29
[52] U.S. Cl. .................. 800/205; 800/200; 800/255; 435/69.1; 435/69.8; 435/172.3; 435/200; 435/240.4; 435/252.3; 530/370; 530/378; 536/23.1; 536/23.2; 536/23.6; 935/60; 935/67; 935/72
[58] Field of Search ................... 435/69.1, 70.1, 435/71.2, 172.3, 183, 200, 240.4, 69.8, 320.1, 252.3; 800/205, 250, 255, 200; 935/9, 10, 14, 67, 72; 536/23.2, 23.6, 23.4; 530/370, 378

[56] References Cited

FOREIGN PATENT DOCUMENTS 0392225 3/1990 European Pat. Off. .

OTHER PUBLICATIONS

Edington et al, "cDNA Cloning And Characterization of a Putative 1,3-β-D-glucanase Transcript Induced By Fungal Elicitor in Bean Cell Suspension Cultures," *Plant Molecular Biology*, 16:81–94 (1991).

Takeuchi et al, "Molecular Cloning and Ethylene Induction of mRNA Encoding a Phytoalexin Elicotor–Releasing Factor, β–1,3–Endoglucanase, in Soybean," *Plant Physiol.*, 93:673–682, (1990).

Keen et al, "β–1,3–Endoglucanase From Soybean Releases Elicotor–Active Carbohydrates From Fungus Cell Walls," *Plant Physiol.*, 71:460–465, (1983).

Cline et al, "Host–Pathogen Interactions," *Plant Physiol.*, 68:221–228, (1981).

De Loose et al, "Primary Structure of a Hormonally Regulated β–Glucanase of Nicotiana Plumbaginifolia," *Gene*, 70:13–23, (1988).

Cline et al, "Host–Pathogen Interactions", *Plant Physiol.*, 68:207–220, (1981).

M J Chrispeels (1991) Ann Rev Plant Physiol Plant Mol Biol 42:21–53.

I K Vasil (1990) Bio/technology 8:296–300.

J. Danecke et al (1990) Plant Cell 2:51–59.

*Primary Examiner*—David T. Fox
*Assistant Examiner*—Bruce Campell
*Attorney, Agent, or Firm*—Foley & Lardner

[57] ABSTRACT

The invention provides a protein, isolated from soybean, having β-1,3-glucanase activity and comprising the amino acid sequence of SEQ ID No: 1. DNA constructs encoding said protein, and transformed plants expressing the protein, are also provided.

25 Claims, 21 Drawing Sheets

100pb

```
HindIII    SphI
         ▼   ▼
.AAGCTTGCATGCCTGCAGGTCGACTCTAGAGGATCCCCCCTGGCGATCATCAAGCCCTAAT
          10           30                50

AGAGGGCTAATCCCTTCACTTGTTTGTTTTGTGGTGTATTATTACATTTTGCACCATGCCT
         70           90               110                MetPro

TCTCTCTTCGCTAGAAACCAGAGGTTCTCATTGGCTACTCTCCTGCTTCTTCTGGAACTA
        130          150               170
SerLeuPheAlaArgAsnGlnArgPheSerLeuAlaThrLeuLeuLeuLeuLeuGluLeu

SphI
                                                   ▼
TTGACAGGAAACCTTCGCATGGCAGATGCTCAAATTGGTGTGTGTTATGGCATGCTGGGC
        190          210               230
LeuThrGlyAsnLeuArgMetAlaAspAlaGlnIleGlyValCysTyrGlyMetLeuGly

AACAATCTACCGTCAGCAAACGATGTTATAGGTCTTTATAGATCAAATAACATAAAGAGA
        250          270               290
AsnAsnLeuProSerAlaAsnAspValIleGlyLeuTyrArgSerAsnAsnIleLysArg

ATGAGACTCTATGATCCTAATCAAGCTGCTCTAGAAGCACTTAGAAATTCTGGCATTGAA
        310          330               350
MetArgLeuTyrAspProAsnGlnAlaAlaLeuGluAlaLeuArgAsnSerGlyIleGlu
```

FIG. 2A

```
370                        390                          410
CTCATTCTTGGGGTGCCAAACTCTGACCTTCAAGGCCTTGCCACCAATCCTGACACTTCT
LeuIleLeuGlyValProAsnSerAspLeuGlnGlyLeuAlaThrAsnProAspThrSer 430                        450                          470
CGTCAATGGGTGCAAAAAACGTGTTGAACTTTTGGCCTAGTGTCAAATCAAGTACGTG
ArgGlnTrpValGlnLysAsnValLeuAsnPheTrpProSerValLysIleLysTyrVal 490                        510                          530
GCAGTTGGAAATGAAGTGAGTCCCCGTTGGAGGCTCTCTTCTTCGGTAGCCCAATATGTTCTA
AlaValGlyAsnGluValSerProValGlyGlySerSerSerValAlaGlnTyrValLeu

550                   SacI 570                          590
CCTGCCCATCCAAAAATGTATACCAAGCAATAAGAGCTCAAGGCCTTCATGATCAAATCAAG
ProAlaIleGlnAsnValTyrGlnAlaIleArgAlaGlnGlyLeuHisAspGlnIleLys 610                        630                          650
GTTTCAACACATCTATTGACATGACCCTAATAGGAAACTCTTTCCCTCCATCGCAAGGTTCC
ValSerThrSerIleAspMetThrLeuIleGlyAsnSerPheProProSerGlnGlySer 670                        690                          710
TTCAGGGGTGATGTGAGATCATACCTAGATCCCATAATTGGGTACTTGGTATATGCAAAT
PheArgGlyAspValArgSerTyrLeuAspProIleIleGlyTyrLeuValTyrAlaAsn
```

FIG. 2B

```
730                               750                               770
GCACCATTACTAGTCAATGTGTACCCCTTATTTTAGTTACACTGGTAACCCCCGTGACATA
AlaProLeuLeuValAsnValTyrProTyrPheSerTyrThrGlyAsnProArgAspIle 790                               810                               830
TCACTTCCCTATGCTCTTTTCACAGCACCAAATGTGTGGTATGGGATGGTCAATATGGG
SerLeuProTyrAlaLeuPheThrAlaProAsnValValValTrpAspGlyGlnTyrGly 850                               870                               890
TACCAAAATTGTTTGATGCTATGTTGGATTCAGTACATGCAGCCATTGATAACACTAAG
TyrGlnAsnLeuPheAspAlaMetLeuAspSerValHisAlaAlaIleAspAsnThrLys 910                               930                               950
ATTGGTTATGTGGAGGTTGTTGTATCCGAGAGTGGGTGGCCATCAGATGGAGGATTTGCT
IleGlyTyrValGluValValSerGluSerGlyTrpProSerAspGlyGlyPheAla 970                               990                               1010
GCCACTTATGACAACGCCACGCGTGTACTTAGACAATTTGGTTCGTGCTAATAGAGGA
AlaThrTyrAspAsnAlaArgValTyrLeuAspAsnLeuValAlaArgArgAlaAsnArgGly 1030                              1050                              1070
AGCCCAAGAAGGCCTTCGAAGCCCACTGAGACTTATATATTTGCCATGTTCGATGAAAAT
SerProArgArgProSerLysProThrGluThrTyrIlePheAlaMetPheAspGluAsn
```

FIG. 2C

```
1090                                    1110                                    1130
CAAAAATCCAGAGATAGAGAAACATTTTGGGCTCTCTTCAATCCCAACAAAAAAA
GlnLysAsnProGluIleGluLysHisPheGlyLeuPheAsnProAsnLysGlnLysLys 1150                                    1170                                    1190
TACCCATTTGGGTTTGGAGGAAAGAGGCTAGGGAAAGTTGTTATTGACGACTTCAATGCA
TyrProPheGlyPheGlyGlyLysArgLeuGlyLysValValIleAspAspPheAsnAla 1210                                    1230                                    1250
ACAACTTCCATTAAGAGTGATGTGTAAGGTTGGAATCCTACTCCCTCAAAATCTCTGTTAT
ThrThrSerIleLysSerAspVal End 1270                                    1290                                    1310
TCCACCCATAAAATAAGAGAGAATATGTTGTTTGTGTGAAATATGTATATATCCTTCAGT 1330                                    1350                                    1370
CTTGGATGAATAAAATTTGTGAAAATTTTATTTTTTTTTTTTTGGACTAGAAATAGCCT 1390                                    1410                                    1430
GATACTTAATTATTATTCTTTTTATACCACGTTGGTTCCTTCATGAGTACAAACCGAA 1450                                    1470  HindIII
ATAAAACCAACAATTAATCTTGTTTTATTACAACACACAAGCTT
```

FIG. 2D

```
HindIII   10                      30                           50
.AAGCTTGCATGCCCTGCAGGTCGACTCTAGAGGATCCCCCTGGCGATCATCAAGCCTAAT
                                                        BamHI
             70                     90                    NdeI 110
AGAGGGCTAATCCCTTCACTTGTTTGTTTTGTGGTGTATTCATATGTTTGAACCATGCCT
                                                        MetPro 130                    150                          170
TCTCTCTCTTCGCTAGAAACCAGAGGTTCTCATTGGCTACTCTCCTGCTTCTTCTGGAACTA
SerLeuPheAlaArgAsnGlnArgPheSerLeuAlaThrLeuLeuLeuLeuLeuGluLeu 190                    210                   SphI 230
TTGACAGGAAGATGCAGAGATGCTCAAATTGGTGTGTGTTATGGCATGCTGGGC
LeuThrGlyAsnLeuArgMetAlaAspAlaGlnIleIleGlyValCysTyrGlyMetLeuGly 250                    270                          290
AACAATCTACCGTCAGCAAACGATGTTATAGGTCTTTATAGATCAAATAACATAAAGAGA
AsnAsnLeuProSerAlaAsnAspValIleGlyLeuTyrArgSerAsnAsnIleLysArg 310                    330                          350
ATGAGACTCTATGATCCTAATCAAGCTGCTCTAGAAGCACTTAGAAATTCTGGCATTGAA
MetArgLeuTyrAspProAsnGlnAlaAlaLeuGluAlaLeuArgAsnSerGlyIleGlu
```

FIG. 3A

```
                    370                              390                              410
CTCATTCTTGGGGGTGCCAAACTCTGACCTTCAAGGCCTTGCCACCAATCCTGACACTTCT
LeuIleLeuGlyValProAsnSerAspLeuGlnGlyLeuAlaThrAsnProAspThrSer 430                              450                              470
CGTCAATGGGGTGCAAAAAAACGTGTTGAACTTTTGGCCTAGTGTCAAATCAAGTACGTG
ArgGlnTrpValGlnLysAsnValLeuAsnPheTrpProSerValLysIleLysTyrVal 490                              510                              530
GCAGTTGGAAATGAAGTGAGTCCCCGTTGGGAGGCTCTTCTTCGGTAGCCCAATATGTTCTA
AlaValGlyAsnGluValSerProValGlyGlySerSerSerValAlaGlnTyrValLeu 550                              570                              590
CCTGCCATCCAAAATGTATACCAAGCAATAAGAGCACAAGGCCTTCATGATCAAATCAAG
ProAlaIleGlnAsnValTyrGlnAlaIleArgAlaGlnGlyLeuHisAspGlnIleLys 610                              630                              650
GTTTCAACAATCTATTGACATGACCCTAATAGGAAACTCTTTCCCTCCATCGCAAGGTTCC
ValSerThrSerIleAspMetThrLeuIleGlyAsnSerPheProProSerGlnGlySer 670                              690                              710
TTCAGGGGTGATGTGAGAATCATACCTAGATCCCATAATTGGGTACTTGGTATATGCAAAT
PheArgGlyAspValArgSerTyrLeuAspProIleIleGlyTyrLeuValTyrAlaAsn
```

FIG. 3B

```
                                                            770
                           750
   730
GCACCATTACTAGTCAATGTGTACCCTTATTTTAGTTACACTGGTAACCCCCGTGACATA
AlaProLeuLeuValAsnValTyrProTyrPheSerTyrThrGlyAsnProArgAspIle 830
                           810
   790
TCACTTCCCTATGCTCTTTTTCACAGCACCAAATGTTGTGGTATGGGATGGTCAATATGGG
SerLeuProTyrAlaLeuPheThrAlaProAsnValValValTrpAspGlyGlnTyrGly 890
                           870
   850
TACCAAAATTTGTTTGATGCTATGTTGGATTCAGTACATGCAGCCATTGATAACACTAAG
TyrGlnAsnLeuPheAspAlaMetLeuAspSerValHisAlaAlaIleAspAsnThrLys 950
                           930
   910
ATTGGTTATGTGGAGGTTGTTGTATCCGAGAGTGGGTGGCCATCAGATGGAGGATTTGCT
IleGlyTyrValGluValValSerGluSerGlyTrpProSerAspGlyGlyPheAla 1010
                           990
   970
GCCACTTATGACAACGCACGCGTGTACTTAGACAATTTGGTTCGTCGTGCTAATAGAGGA
AlaThrTyrAspAsnAlaArgValTyrLeuAspAsnLeuValArgArgAlaAsnArgGly 1070
                           1050
   1030
AGCCCAAGAAGGCCTTCGAAGCCCACTGAGACTTATATATATTTGCCATGTTCGATGAAAAT
SerProArgArgProSerLysProThrGluThrTyrIlePheAlaMetPheAspGluAsn
```

FIG. 3C

```
1090                                    1110
CAAAAATCCAGAGAGATAGAGAAAACATTTGGGCTCTCTTCAATCCCAACAAAAAAAA
GlnLysAsnProGluIleGluLysHisPheGlyLeuPheAsnProAsnLysGlnLysLys 1150                                    1170                              1190
TACCCATTTGGGGTTTGGAGGAAAGAGGCTAGGGAAAGAGTTGTTATTGACGACTTCAATGCA
TyrProPheGlyPheGlyGlyLysArgLeuGlyLysLysValValIleAspAspPheAsnAla 1210                    1230  SacI HindIII  1250
ACAACTTCCATTAAGAGTGATGTGTAAGGTTGAGCTCCTAAGCTTCAAATCTCTGTTAT
ThrThrSerIleLysSerAspValEnd 1270                                    1290                              1310
TCCACCCCATAAAATAAGAGAGAATATGTTGTTTGTGTGAAATATGTATATCCTTCAGT 1330                                    1350                              1370
CTTGGGATGAATAAAATTTGTGAAAATTTTATTTTTTTTTTTTTGGACTAGAAATAGCCT 1390                                    1410                              1430
GATACTTAATTATTATTATCTTTTTATACCACACGTTGGTTTCCTTCATGAGTACAAACCGAA 1450                    1470  HindIII
ATAAAACCAACAACAATTAATCTTGTTTTAATTACAACACACAAGCTT
```

FIG. 3D

```
NdeI       10                           30                            50
 ↓
CATATGATTGGTGTGTGTTATGGCATGCTGGGCAACAATCTACCGTCAGCAAACGATGTT
     MetIleGlyValCysTyrGlyMetLeuGlyAsnAsnLeuProSerAlaAsnAspVal 70                           90                           110
ATAGGTCTTTATAGATCAAATAACATAAAGAGAATGAGACTCTATGATCCTAATCAAGCT
 IleGlyLeuTyrArgSerAsnAsnIleLysArgMetArgLeuTyrAspProAsnGlnAla 130                          150                          170
GCTCTAGAAGCACTTAGAAATTCTGGCATTGAACTCATTCTTGGGGTGCCAAACTCTGAC
 AlaLeuGluAlaLeuArgAsnSerGlyIleLeuIleLeuGlyValProAsnSerAsp 190                          210                          230
CTTCAAGGCCTTGCCACCAATCCTGACACTTCTCGTCAATGGGTGCAAAAAACGTGTTG
 LeuGlnGlyLeuAlaThrAsnProAspThrSerArgGlnTrpValGlnLysAsnValLeu 250                          270                          290
AACTTTTGGCCTAGTGTCAAAATCAAGTACGTGGCAGTTGGAAATGAAGTGAGTCCCGTT
 AsnPheTrpProSerValLysIleLysTyrValAlaValGlyAsnGluValSerProVal 310                          330                          350
GGAGGCTCTTCTTCGGTAGCCCAATATGTTCTACCTGCCATCCAAAATGTATACCAAGCA
 GlyGlySerSerSerValAlaGlnTyrValLeuProAlaIleGlnAsnValTyrGlnAla
```

FIG. 4A

```
                    370                                    390                                    410
ATAAGAGCACAAGGCCCTTTCATGATCAAATCAAGGTTTCAACATCTATTGACACATGACCCTA
IleArgAlaGlnGlyLeuHisAspGlnIleLysValSerThrSerIleAspMetThrLeu 430                                    450                                    470
ATAGGAAACTCTTTCCCTCCATCGCAAGGTTCCTTCAGGGGTGATGTGAGATCATACCTA
IleGlyAsnSerPheProProSerGlnGlySerPheArgGlyAspValArgSerTyrLeu 490                                    510                                    530
GATCCCATAATTGGGTACTTGGTATATGCAAATGCACCATTACTAGTCAATGTGTACCCT
AspProIleIleGlyTyrLeuValTyrAlaAsnAlaProLeuLeuValAsnValTyrPro 550                                    570                                    590
TATTTTAGTTACACTGGTAACCCCCGTGACATATCACTTCCCTATGCTCTTTTCACAGCA
TyrPheSerTyrThrGlyAsnProArgAspIleSerLeuProTyrAlaLeuPheThrAla 610                                    630                                    650
CCAAATGTTGTGGTATGGGATGGTCAATATATGGGTACCAAAATTTGTTTGATGCTATGTTG
ProAsnValValValTrpAspGlyGlnTyrGlyTyrGlnAsnLeuPheAspAlaMetLeu 670                                    690                                    710
GATTCAGTACATGCAGCCATTGATAACACTAAGATTGGTTATGTGGAGGTTGTTGTATCC
AspSerValHisAlaAlaIleAspAsnThrLysIleGlyTyrValGluValValSer
```

FIG. 4B

```
                                              770
                  750
730
GAGAGTGGGTGGCCATCAGATGGAGGATTTGCTGCCACTTATGACAACGCACGCGTGTAC
GluSerGlyTrpProSerAspGlyGlyPheAlaAlaThrTyrAspAsnAlaArgValTyr 830
                  810
790
TTAGACAATTTGGTTCGTCGTGCTAATAGAGGAAGCCCAAGAAGGCCTTCGAAGCCCACT
LeuAspAsnLeuValArgArgAlaAsnArgGlySerProArgArgProSerLysProThr 890
                  870
850
GAGACTTATATATTTGCCATGTTCGATGAAAATCAAAAAATCCAGAGATAGAGAAACAT
GluThrTyrIlePheAlaMetPheAspGluAsnGlnLysAsnProGluIleGluLysHis 950
                  930
910
TTTGGGCTCTTCAATCCCAACAAAAACAAAAAATACCCATTTGGGTTTGGAGGAAAGAGG
PheGlyLeuPheAsnProAsnLysGlnLysLysTyrProPheGlyPheGlyLysArg 1010
                  990
970
CTAGGGAAAGTTGTTATTGACGACTTCAATGCAACAACTTCCATTAAGAGTGATGTGTAA
LeuGlyLysValValIleAspAspPheAsnAlaThrThrSerIleLysSerAspValEnd

1030  HindIII
GGTTGAGCTCCTAAGCTT
```

FIG. 4C

HindIII    10              30              50
▼
.AAGCTTGCACGACACACTTGTCTACTCCAAAATATCAAAGATACAGTCCTCAGAAGAC 70              90              110
CAAAGGGCCAATTGAGACTTTTCAACAAAGGGTAATATCCGGAAACCCTCGGATTCCA 130             150             170
TTGCCCAGCTATCTGTGTCACTTTATTGTGAAGATAGTGGAAAAGGAAGGTGGCTCCTACAA 190             210             230
ATGCCATCATTGCCGATAAAGGAAAAGGCCATCGTGTTGAAGATGCCCTCTGCCGACAGTGGTCC 250             270             290
CAAAGATGGACCCCCCACCCCACGAGGAGCATCGTGTGGAAAAAGAAGAAGACGTTCCAACCACGTC 310             330             350
TTCAAAGCAAGTGGATTGATGTGATATCTCCACTGACTGACGTAAGGGATGACGCACAATCCCA 370             390             410
CTATCCTTCGCAAGACCCTTCCCTCTATATAAGGAAGTTCATTTCATTTGGAGAGAACACG

FIG. 5A

```
                    BamHI
      430            ▼            450                           470
GGGGACTCTAGAGGATCCATGCCTTCTCTCTTCGCTAGAAACCAGAGGTTCTCATTGCT
                    MetProSerLeuPheAlaArgAsnGlnArgPheSerLeuAla 490                        510                            530
ACTCTCCTGCTTCTTCTGGAACTATTGACAGGAAACCTTCGCATGGCAGATGCTCAAATT
ThrLeuLeuLeuLeuLeuGluLeuLeuThrGlyAsnLeuArgMetAlaAspAlaGlnIle 550                        570                            590
GGTGTGTGTTATGGCATGCTGGGCAACAATCTACCGTCAGCAAACGATGTTATAGGTCTT
GlyValCysTyrGlyMetLeuGlyAsnAsnLeuProSerAlaAsnAspValIleGlyLeu 610                        630                            650
TATAGATCAAATAACATAAAGAGAATGAGACTCTATGATCCTAATCAAGCTGCTCTAGAA
TyrArgSerAsnAsnIleLysArgMetArgLeuTyrAspProAsnGlnAlaAlaLeuGlu 670                        690                            710
GCACTTAGAAATTCTGGCATTGAACTCATTCTTGGGGTGCCAAACTCTGACCTTCAAGGC
AlaLeuArgAsnSerGlyIleLeuIleLeuLeuGlyValProAsnSerAspLeuGlnGly 730                        750                            770
CTTGCCACCAATCCCTGACACTTCTCGTCAATGGGTGCAAAAAACGTGTTGAACTTTTGG
LeuAlaThrAsnProAspThrSerArgGlnTrpValGlnLysAsnValLeuAsnPheTrp
```

FIG. 5B

```
                                            830
           810
 790
CCTAGTGTCAAAATCAAGTACGTGGCAGTTGGAAATGAAGTGAGTCCCGTTGGAGGCTCT
ProSerValLysIleLysTyrValAlaValGlyAsnGluValSerProValGlyGlySer 890
           870
 850
TCTTCGGTAGCCCAATATGTTCTACCTGCCATCCAAAATGTATACCAAGCAATAAGAGCA
SerSerValAlaGlnTyrValLeuProAlaIleGlnAsnValTyrGlnAlaIleArgAla 950
           930
 910
CAAGGCCTTCATGATCAAATCAAGGTTTCAACATCTATTGACATGACCCTAATAGGAAAC
GlnGlyLeuHisAspGlnIleLysValSerThrSerIleAspMetThrLeuIleGlyAsn 1010
           990
 970
TCTTTCCCTCCATCGCAAGGTTCCTTCAGGGGTGATGTGAGATCATACCTAGATCCCATA
SerPheProProSerGlnGlySerPheArgGlyAspValArgSerTyrLeuAspProIle 1070
           1050
 1030
ATTGGGTACTTGGTATATGCAAATGCACCATTACTAGTCAATGTGTACCCTTATTTTAGT
IleGlyTyrLeuValTyrAlaAsnAlaProLeuLeuValAsnValTyrProTyrPheSer 1130
           1110
 1090
TACACTGGTAACCCCCGTGACATATCACTTCCCTATGCTCTTTTCACAGCACCAAATGTT
TyrThrGlyAsnProArgAspIleSerLeuProTyrAlaLeuPheThrAlaProAsnVal
```

FIG. 5C

```
                                        1150                                            1170                                           1190
GTGGTATGGGGATGGGTCAATATGGGTACCAAAATTTGTTTGATGCTATGTTGGATTCAGTA
ValValTrpAspGlyGlnTyrGlyTyrGlnAsnLeuPheAspAlaMetLeuAspSerVal 1210                                            1230                                           1250
CATGCAGCCATTGATAACACTAAGATTGGTTATGTGGAGGTTGTTGTATCCGAGAGTGGG
HisAlaAlaIleAspAsnThrLysIleGlyTyrValGluValValValSerGluSerGly 1270                                            1290                                           1310
TGGCCATCAGATGGAGGATTTGCTGCCACTTATGACAACGCACGCGTGTACTTAGACAAT
TrpProSerAspGlyGlyPheAlaAlaThrTyrAspAsnAlaArgValTyrLeuAspAsn 1330                                            1350                                           1370
TTGGTTCGTCGTGCTAATAGAGAGGAAGCCCAAGAAGGCCTTCGAAGCCCACTGAGACTTAT
LeuValArgArgAlaAsnArgGlySerProArgArgProSerLysProThrGluThrTyr 1390                                            1410                                           1430
ATATTTGCCATGTTCGATGAAAATCAAAAATCCAGAGATAGAGAAACATTTTGGGCTC
IlePheAlaMetPheAspGluAsnGlnLysAsnProGluIleGluLysHisPheGlyLeu 1450                                            1470                                           1490
TTCAATCCCAACAAACAAAAAAATACCCATTTGGGTTTGGAGGAAAGAGGCTAGGGAAA
PheAsnProAsnLysGlnLysTyrProPheGlyPheGlyLysArgLeuGlyLys
```

FIG. 5D

```
                                                                     SacI
       1510                  1530             1550            ↓
GTTGTTATTGACGACTTCAATGCAACAACTTCCATTAAGAGTGATGTGTAAGGTTGAGCT
ValValIleAspAspPheAsnAlaThrThrSerIleLysSerAspValEnd 1570             1590               1610
CGAATTCCCCGATCGTTCAAACATTGGCAATAAAGTTTCTTAAGATTGAATCCTGTTG 1630              1650              1670
CCGGTCTTGCGATGATTATCATATATAATTTCTGTTGAATTACGTTAAGCATGTAATAATTA 1690              1710             1730
ACATGTAATGCATGACGTTATTTATGAGATGGGGTTTTTATGATTAGAGTCCCCGCAATTAT 1750              1770             1790
ACATTTAATACGCGATAGAAAACAAAATATAGCGCGCAAACTAGGATAAATTATCGGCG
                                EcoRI
        1810                          ↓
CGGTGTCATCTATGTTACTAGATCGAATTC
```

FIG. 5E

```
IleGlyValCysTyrGlyMet
LeuGlyAsnAsnLeuProSerAlaAsnAspValIleGlyLeuTyrArgSerAsnAsnIle
LysArgMetArgLeuTyrAspProAsnGlnAlaAlaLeuGluAlaLeuArgAsnSerGly
IleGluLeuIleLeuGlyValProAsnSerAspLeuGlyLeuAlaThrAsnProAsp
ThrSerArgGlnTrpValGlnLysAsnValLeuAsnPheTrpProSerValLysIleLys
TyrValAlaValGlyAsnGluValSerProValGlyGlySerSerSerValAlaGlnTyr
ValLeuProAlaIleGlnAsnAsnValTyrGlnAlaIleArgAlaGlnGlyLeuHisAspGln
IleLysValSerThrSerIleAspMetThrLeuIleGlyAsnSerPheProProSerGln
GlySerPheArgGlyAspValArgSerTyrLeuAspProIleIleGlyTyrLeuValTyr
```

FIG. 6A

AlaAsnAlaProLeuLeuValAsnValTyrProTyrPheSerTyrThrGlyAsnProArg
AspIleSerLeuProTyrAlaLeuPheThrAlaProAsnValValValTrpAspGlyGln
TyrGlyTyrGlnAsnLeuPheAspAlaMetLeuAspSerValHisAlaAlaIleAspAsn
ThrLysIleGlyTyrValGluValValValValSerGluSerGlyTrpProSerAspGlyGly
PheAlaAlaThrTyrAspAsnAlaArgValTyrLeuAspAsnLeuValArgArgAlaAsn
ArgGlySerProArgArgProSerLysProThrGluThrTyrIlePheAlaMetPheAsp
GluAsnGlnLysAsnProGluIleGluLysHisPheGlyLeuPheAsnProAsnLysGln
LysLysTyrProPheGlyPheGlyLysArgLeuGlyLysValValIleAspAspPhe
AsnAlaThrThrSerIleLysSerAspVal

FIG. 6B

```
1    MPSLFARNQRFSLATLLLLLELLTGNLRMADAQIGVCYGMLGNNLPSAND     50
          : :  . : :|  :|:..:  |     :.|::.|||||||||||
1    .MDTSHKHIALQMAAIILLGLLVSSTEIVGAQSVGVCYGMLGNNLPPASQ     49

51   VIGLYRSNNIKRMRLYDPNQAALEALRNSGIELILGVPNSDLQGLATNPD    100
     |:: ||:.||:||||||||||||| ||||:|:|:||||||||| :.|
50   VVQLYKSKNIRRMRLYDPNQAALQALRGSNIEVMLGVPNSDLQNIAANPS     99

101  TSRQWVQKNVLNFWPSVKIKYVAVGNEVSPVGGSSSVAQYVLPAIQNVYQ    150
     .: ||:|:|| |:||:||||:|:||||||| ||.:||||||:|||: |:
100  NANNWVQRNVRNFWPAVKFRYIAVGNEVSPVTGTSSLTRYLLPAMRNIRN    149

151  AIRAQGLHDQIKVSTSIDMTLIGNSFPPSQGSFRGDVRSYLDPIIGYLVY    200
     ||.: ||:|:|||:|.||||||||||||||||| ||||| ||||||::|
150  AISSAGLQNNIKVSSSVDMTLIGNSFPPSQGSFRNDVRSFIDPIIGFVRR    199
```

FIG. 7A

```
201 ANAPLLVNVYPYFSYTGNPRDISLPYALFTAPNVVVWDGQYGYQNLFDAM 250
    |.||||:||||||||||||||||||||||||||:|| .||.|||||||||
200 INSPLLVNIYPYFSYAGNPRDISLPYALFTAPNVVVQDGSLGYRNLFDAM 249

251 LDSVHAAIDNTKIGYVEVVVSESGWPSDGGFAATYDNARVYLDNLVRRAN 300
    |.|.||..:.|:||||| |..:||||||||:|:|||| .|.|.:.:..:
250 SDAVYAALSRAGGGSIEIVVSESGWPSAGAFAATTNNAATYYKNLIQHVK 299

301 RGSPRRPSKPTETYIFAMFDENQKNPEIEKHFGLFNPNKQKKYPFGFG.G 349
    |||||||.|.:|||:||||||||:|||:||||||||.||:||||.||.|
300 RGSPRRPNKVIETYLFAMFDENNKNPELEKHFGLFSPNKQPKYPLSFGFS 349

350 KRLGKVVIDDFNATTSIKSDV* 371
    .|..:..|:::|.|:|..:|
350 DRYWDISAENNATAAASLISEM. 370
```

FIG. 7B

RECOMBINANT DNA CODING FOR A NOVEL PROTEIN HAVING β-1,3-GLUCANASE ACTIVITY, BACTERIA CONTAINING THIS DNA, TRANSFORMED PLANT CELLS AND PLANTS

BACKGROUND OF THE INVENTION

The invention relates to a recombinant DNA coding for a novel protein having β-1,3-glucanase activity, or for a precursor of this protein, to a bacterium containing this recombinant DNA, to a plant cell, plant or plant part, especially a plant seed, transformed by this recombinant DNA, as well as to this novel protein and to a method for preparing it.

Crop plants are known to be subjected to attack by parasites such as phytopathogenic fungi, which are responsible for substantial harvest losses. The main means at present for controlling these fungi lies in the use of chemical substances having fungicidal activity. It is now known that plants react naturally to such attack by various defence mechanisms, which are unfortunately, in general, triggered too late and at too low an intensity to be sufficiently effective.

One of these mechanisms comprises the induction of an enzyme known as β-1,3-glucanase E.C.3.2.1.39 (Kombrink et al., 1988, Pr. Ntl. Acad. Sci. USA, 85,982–986 and Pegg et al., 1981, Physiol. Plant. Pathol. 19,371–382). This induction can be triggered artificially through the effect of elicitors, that is to say compounds of biological origin capable of inducing in a healthy plant the defence reactions which it deploys naturally during an infection by pathogenic agents, or during a hormonal imbalance caused by auxin, cytokinins or ethylene (Abeles et al., 1971, Plant Physiol. 47,129–134 and de Loose et al., 1988, Gene, 70,13–23).

β-1,3-glucans are linear polysaccharide polymers consisting of glucose units linked via β-(1→3) linkages, sometimes possessing β-(1→4) or β-(1→6) type branching (Farka 1982, in "Fungal protoplasts", Peberdy and Ferencry, published by Dekker Inc.). These polysaccharides constitute a typical component of the skeleton of the wall of most fungi, and in particular phytopathogenic fungi. β-1,3-glucanases are capable of degrading them by fragmentation of the β-1,3-glucan chains. Most known plant β-1,3-glucanases are of the endo type.

It is known, moreover, that recent progress in so-called recombinant DNA technology and in the transformation of plant cells, as well as in the regeneration of whole plants from the latter, enable a gene of interest to be introduced into plant cells, a plant or a plant part so as to obtain an advantageous phenotype.

SUMMARY OF THE INVENTION

DNA sequences coding for several plant β-1,3-glucanases, in particular a *Nicotiana plumbaginifolia* β-1,3-glucanase (De Loose et al., 1988, Gene, 70,13–23) and a soybean β-1,3-glucanase (Takeuchi et al., 1990, Plant Physiol., 93,673–682), have been isolated, cloned and determined. Patent Application EP-A-0,353,191 describes the isolation and cloning of different fragments of complementary DNA, the assembling of which enables the complementary DNA sequence coding for a tobacco β-1,3-glucanase to be deduced, as well as of the genomic DNA sequence coding for this enzyme. The document EP-0,392,225 discloses, in particular, the construction of a chimeric gene coding for this tobacco β-1,3-glucanase, the transformation of tobacco with the latter and the verification, by Western blot and visualisation using polyclonal antibodies, of the over-expression of this endogenous protein in the transformed plants. This patent application does not show that the recombinant tobacco β-1,3-glucanase is biologically active, nor a fortiori that it confers a resistance of the said transformed plants to pathogenic agents.

It is known, moreover, that β-1,3-glucanases such as, for example, *Bacillus subtilis* β-1,3-glucanase are useful enzymes in the conversion of biomass, in particular in some sectors of the papermaking industry and in the agri-foodstuffs industry, especially brewing (Meaden, 1986, Brewers Guardian, 115, 7 and MacQueen, October 1987, New Scientist, 66).

It is known, lastly, that many recombinant proteins can be produced by eukaryotic cells and bacteria, following introduction into these of genes coding for the said proteins using conventional genetic engineering techniques.

The present invention relates to a novel recombinant DNA, characterised in that it codes for a protein having β-1,3-glucanase activity or for a precursor thereof, this protein having β-1,3-glucanase activity comprising the following amino acid sequence $(a_1)$ (SEQ ID NO:1):

---

Ile Gly Val Cys Tyr Gly Met Leu Gly Asn Asn Leu Pro Ser
Ala Asn Asp Val Ile Gly Leu Tyr Arg Ser Asn Asn Ile Lys
Arg Met Arg Leu Tyr Asp Pro Asn Gln Ala Ala Leu Glu Ala
Leu Arg Asn Ser Gly Ile Glu Leu Ile Leu Gly Val Pro Asn
Ser Asp Leu Gln Gly Leu Ala Thr Asn Pro Asp Thr Ser Arg
Gln Trp Val Gln Lys Asn Val Leu Asn Phe Trp Pro Ser Val
Lys Ile Lys Tyr Val Ala Val Gly Asn Glu Val Ser Pro Val
Gly Gly Ser Ser Ser Val Ala Gln Tyr Val Leu Pro Ala Ile
Gln Asn Val Tyr Gln Ala Ile Arg Ala Gln Gly Leu His Asp
Gln Ile Lys Val Ser Thr Ser Ile Asp Met Thr Leu Ile Gly
Asn Ser Phe Pro Pro Ser Gln Gly Ser Phe Arg Gly Asp Val
Arg Ser Tyr Leu Asp Pro Ile Ile Gly Tyr Leu Val Tyr Ala
Asn Ala Pro Leu Leu Val Asn Val Tyr Pro Tyr Phe Ser Tyr
Thr Gly Asn Pro Arg Asp Ile Ser Leu Pro Tyr Ala Leu Phe
Thr Ala Pro Asn Val Val Val Trp Asp Gly Gln Tyr Gly Tyr
Gln Asn Leu Phe Asp Ala Met Leu Asp Ser Val His Ala Ala
Ile Asp Asn Thr Lys Ile Gly Tyr Val Glu Val Val Val Ser
Glu Ser Gly Trp Pro Ser Asp Gly Gly Phe Ala Ala Thr Tyr
Asp Asn Ala Arg Val Tyr Leu Asp Asn Leu Val Arg Arg Ala
Asn Arg Gly Ser Pro Arg Arg Pro Ser Lys Pro Thr Glu Thr
Tyr Ile Phe Ala Met Phe Asp Glu Asn Gln Lys Asn Pro Glu
Ile Glu Lys His Phe Gly Leu Phe Asn Pro Asn Lys Gln Lys
Lys

--- or a sequence possessing a high degree of homology with the sequence $(a_1)$, (SEQ ID NO:1).

A high degree of homology means here a homology (ratio of identical amino acids to the total number of amino acids) of at least 80%, and preferably at least 90%, of the amino acid sequences when they are aligned on the basis of maximal homology according to the optimal sequence alignment method of Needleman and Wunsch, 1970, J. Mol. Biol., 48, 443–453. This method is used, in particular, in the University of Wisconsin's UWGCG software : Devereux et al., 1984, Nucl. Ac. Res., 12, 8711–8721—GAP option.

The already known peptide sequence closest to that of the sequence $(a_1)$ (SEQ ID NO.1): of 307 amino acids is that of the protein of 369 amino acids deduced from the complementary DNA of a *Nicotiana plumbaginifolia* β-1,3-glucanase SEQ ID NO.12) (see Swissprot data bank ref. Gus$ Nipl. and De Loose et al., 1988, Gene, 70, 13–23). A comparison of these two sequences using the method of Needleman and Wunsch, 1970, J. Mol. Biol., 48,443–453, shows that 213 amino acids out of 307 are identical, equivalent to an approximately 69% homology. This algorithmic method, which considers all possible alignments and creates an alignment, shown in FIGS. 7A and 7B in which the largest possible number of identical amino acids are paired and the number of holes in the aligned sequences is minimal, is used, in particular, in the University of Wisconsin's UWGCG software: Devereux et al., 1984, Nucl. Ac. Res., 12, 8711–8721—GAP option.

This novel recombinant DNA may be used for the expression of this protein having β-1,3-glucanase activity, either to confer an enhanced resistance to pathogenic agents on a plant or plant part expressing the protein, or to produce this protein using eukaryotic cells, in particular ascomycetes such as yeast or filamentous fungi, for example *Cryphonectria parasitica*, or plant cells, or prokaryotic microorganisms such as, for example, *Escherichia coli*.

This recombinant DNA can contain, immediately downstream of the nucleotide sequence coding for the amino acid sequence ($a_1$) (SEQ ID NO1), the nucleotide sequence coding for the following amino acid sequence ($a_4$) (SEQ ID NO:4):

Tyr Pro Phe Gly Phe Gly Gly Lys Arg Leu Gly Lys Val Val
Ile Asp Asp Phe Asn Ala Thr Thr Ser Ile Lys Ser Asp Val truncated in its carboxy-terminal portion by 0 to 27 amino acids.

Advantageously, this recombinant DNA comprises immediately upstream of the nucleotide sequence coding for the amino acid sequence ($a_1$) (SEQ ID NO:1), a codon for Gln.

An especially high valued DNA such as defined above is that which codes for a protein having β-1,3-glucanase activity or a precursor thereof, and which comprises the following sequence ($a_5$) (SEQ ID NO:3):

Gln
Ile Gly Val Cys Tyr Gly Met Leu Gly Asn Asn Leu Pro Ser
Ala Asn Asp Val Ile Gly Leu Tyr Arg Ser Asn Asn Ile Lys
Arg Met Arg Leu Tyr Asp Pro Asn Gln Ala Ala Leu Glu Ala
Leu Arg Asn Ser Gly Ile Glu Leu Ile Leu Gly Val Pro Asn
Ser Asp Leu Gln Gly Leu Ala Thr Asn Pro Asp Thr Ser Arg
Gln Trp Val Gln Lys Asn Val Leu Asn Phe Trp Pro Ser Val
Lys Ile Lys Tyr Val Ala Val Gly Asn Glu Val Ser Pro Val
Gly Gly Ser Ser Ser Val Ala Gln Tyr Val Leu Pro Ala Ile
Gln Asn Val Tyr Gln Ala Ile Arg Ala Gln Gly Leu His Asp
Gln Ile Lys Val Ser Thr Ser Ile Asp Met Thr Leu Ile Gly
Asn Ser Phe Pro Pro Ser Gln Gly Ser Phe Arg Gly Asp Val
Arg Ser Tyr Leu Asp Pro Ile Ile Gly Tyr Leu Val Tyr Ala
Asn Ala Pro Leu Leu Val Asn Val Tyr Pro Tyr Phe Ser Tyr
Thr Gly Asn Pro Arg Asp Ile Ser Leu Pro Tyr Ala Leu Phe
Thr Ala Pro Asn Val Val Val Trp Asp Gly Gln Tyr Gly Tyr
Gln Asn Leu Phe Asp Ala Met Leu Asp Ser Val His Ala Ala
Ile Asp Asn Thr Lys Ile Gly Tyr Val Glu Val Val Val Ser
Glu Ser Gly Trp Pro Ser Asp Gly Gly Phe Ala Ala Thr Tyr
Asp Asn Ala Arg Val Tyr Leu Asp Asn Leu Val Arg Arg Ala
Asn Arg Gly Ser Pro Arg Arg Pro Ser Lys Pro Thr Glu Thr
Tyr Ile Phe Ala Met Phe Asp Glu Asn Gln Lys Asn Pro Glu
Ile Glu Lys His Phe Gly Leu Phe Asn Pro Asn Lys Gln Lys
Lys Tyr Pro Phe Gly Phe Gly Gly Lys Arg Leu Gly Lys Val
Val Ile Asp Asp Phe Asn Ala Thr Thr Ser Ile Lys Ser Asp
Val

This recombinant DNA preferably contains, upstream of the sequence coding for the sequence ($a_1$) (SEQ ID NO:1) optionally preceded by a codon for Gln, a signal sequence, chosen in accordance with the host cell, which has the function of enabling the protein to be exported from the cytoplasm.

For an expression in prokaryotic microorganisms such as, for example, *Escherichia coli*, this signal sequence can be either a sequence derived from a sequence coding for a natural precursor of a protein exported by a prokaryotic microorganism, for example the OmpA signal peptide (Ghrayeb et al., 1984, EMBO Journal, 3, 2437–2442) or an alkaline phosphatase precursor (J. Bact. 1983, 154, 366–3747), or a non-endogenous sequence originating from a sequence coding for a eukaryotic precursor (for example the signal peptide of one of the natural precursors of human growth hormone), or a sequence coding for a synthetic signal peptide (for example that described in French Patent Application No. 2,636,643, of sequence (SEQ ID NO:4):

Met Ala Pro Ser Gly Lys Ser Thr Leu Leu Leu Leu Phe Leu
Leu Leu Cys Leu Pro Ser Trp Asn Ala Gly Ala.

For an expression in eukaryotic cells such as ascomycetes, for example *Saccharomyces cerevisiae* yeast or the filamentous fungus *Cryphonectria parasitica*, this signal sequence is preferably a sequence derived from a sequence coding for a natural precursor of a protein secreted by these cells, for example, for yeast, the invertase precursor (Patent Application EP-0,123,298) or the precursor of the prepro sequence of the alpha pheromone (Patent Application DK 2484/84), or for *Cryphonectria parasitica*, the precursor of the prepro sequence of endothiapepsin (described in French patent application no. 2 666 590), of sequence (SEQ ID NO: 5):

Met Ser Ser Pro Leu Lys Asn Ala Leu Val Thr Ala Met Leu
Ala Gly Gly Ala Leu Ser Ser Pro Thr Lys Gln His Val Gly
Ile Pro Val Asn Ala Ser Pro Glu Val Gly Pro Gly Lys Tyr
Ser Phe Lys Gln Val Arg Asn Pro Asn Tyr Lys Phe Asn Gly
Pro Leu Ser Val Lys Lys Thr Tyr Leu Lys Tyr Gly Val Pro
Ile Pro Ala Trp Leu Glu Asp Ala Val Gln Asn Ser Thr Ser
Gly Leu Ala Glu Arg

For an expression in plant cells, either a sequence coding for the signal peptide of a plant cell protein known to be exported, for example the following sequence described in French patent application no. 2 665 177 (SEQ ID NO:6):

Met Arg Arg Thr Ser Lys Leu Thr Thr Phe Ser Leu
Leu Phe Ser Leu Val Leu Leu Ser Ala Ala Leu Ala or a signal sequence coding for the signal peptide of the following sequence ($a_2$) (SEQ ID NO:7):

Met Pro Ser Leu Phe Ala Arg Asn Gln Arg Phe Ser Leu
Ala Thr Leu Leu Leu Leu Leu Glu Leu Leu Thr Gly Asn Leu
Arg Met Ala Asp Ala is used as a signal sequence.

The amino acid sequences ($a_1$), ($a_2$) and ($a_4$), (SEQ ID NOS:1, 7 and 2, respectively) can, for example, be encoded by the nucleotide sequences ($Na_1$) (SEQ ID NO:8), ($Na_2$) and ($Na_4$) below:

(Na₁):
ATTGGTGTGT GTTATGGCAT GCTGGGCAAC AATCTACCGT CAGCAAACGA
TGTTATAGGT CTTTATAGAT CAAATAACAT AAAGAGAATG AGACTCTATG
ATCCTAATCA AGCTGCTCTA GAAGCACTTA GAAATTCTGG CATTGAACTC
ATTCTTGGGG TGCCAAACTC TGACCTTCAA GGCCTTGCCA CCAATCCTGA
CACTTCTCGT CAATGGGTGC AAAAAAACGT GTTGAACTTT TGGCCTAGTG
TCAAAATCAA GTACGTGGCA GTTGGAAATG AAGTGAGTCC CGTTGGAGGC
TCTTCTTCGG TAGCCCAATA TGTTCTACCT GCCATCCAAA ATGTATACCG
AGCAATAAGA GCTCAAGGCC TTCATGATCA AATCAAGGTT TCAACATCTA
TTGACATGAC CCTAATAGGA AACTCTTTCC CTCCATCGCA AGGTTCCTTC
AGGGGTGATG TGAGATCATA CCTAGATCCC ATAATTGGGT ACTTGGTATA
TGCAAATGCA CCATTACTAG TCAATGTGTA CCCTTATTTT AGTTACACTG
GTAACCCCCG TGACATATCA CTTCCCTATG CTCTTTTCAC AGCACCAAAT
GTTGTGGTAT GGGATGGTCA ATATGGGTAC CAAAATTTGT TTGATGCTAT
GTTGGATTCA GTACATGCAG CCATTGATAA CACTAAGATT GGTTATGTGG
AGGTTGTTGT ATCCGAGAGT GGGTGGCCAT CAGATGGAGG ATTTGCTGCC
ACTTATGACA ACGCACGCGT GTACTTAGAC AATTTGGTTC GTCGTGCTAA
TAGAGGAAGC CCAAGAAGGC CTTCGAAGCC CACTGAGACT TATATATTTG
CCATGTTCGA TGAAAATCAA AAAAATCCAG AGATAGAGAA ACATTTTGGG
CTCTTCAATC CCAACAAACA AAAAAAA
(Na₂) (SEQ ID NO: 9):
ATGCCTTCTC TCTTCGCTAG AAACCAGAGG TTCTCATTGG CTACTC.TCCT
GCTTCTTCTG GAACTATTGA CAGGAAACCT TCGCATGGCA GATGCT
(Na₄) (SEQ ID NO: 10):
TACCCATTTG GGTTTGGAGG AAAGAGGCTA GGGAAAGTTG TTATTGACGA
CTTCAATGCA ACAACTTCCA TTAAGAGTGA TGTG The invention also relates to a unit for expression of the recombinant DNA defined above, advantageously carried out by a vector, termed expression vector.

For an expression in procaryotic microorganisms, especially in *Escherichia coli*, the recombinant DNA must be inserted in an expression unit containing, in particular, an effective promoter, followed by a ribosome binding site upstream of the gene to be expressed, as well as an effective transcription stop sequence downstream of the gene to be expressed. This unit must also contain a selection marker or be introduced into the host cell at the same time as a unit for expression of a selection marker (for example using an expression vector which carries both of these units). All these sequences must be chosen in accordance with the host cell.

For an expression in eukaryotic cells such as ascomycetes, the expression unit according to the invention comprises the recombinant DNA defined above with the means needed for its expression.

For an expression in ascomycete cells such as yeast, for example *Saccharomyces cerevisiae*, it is appropriate to insert the recombinant DNA between, on the one hand sequences recognised as an effective promoter, and on the other hand a transcription terminator. The expression unit carries a selection marker or is introduced into the host cell at the same time as a selection marker. Preferably, this selection marker is an auxotrophic marker (which complements a mutation of the recipient cells) which permits the selection of cells which have integrated the recombinant DNA in a high copy number, either into their genome or into a multicopy vector. For an expression in ascomycete cells such as those of filamentous fungi, for example those of the genera Aspergillus, Neurospora, Podospora, Trichoderma or Cryphonectria, the expression unit according to the invention carries the recombinant DNA defined above with the means needed for its expression, and optionally a selection marker and/or telomeric sequences. It is, in effect, possible to select transformants which have integrated a DNA of interest using a selection marker located either on the same unit as the DNA of interest or on another unit, these two units then being introduced by cotransformation. The recombinant DNA of the invention may be either integrated in the genome of the filamentous fungi, or preserved in extrachromosomal form by means of sequences enabling this DNA to be replicated and split.

For an expression in plant cells, it is appropriate to insert the recombinant DNA defined above between a promoter and a terminator which are effective in plants.

The promoter is preferably a strong constitutive promoter, for example the 35S promoter of the cauliflower mosaic virus, or a promoter controlling the tissue- or organ-specific expression, such as the promoter of the small subunit of ribulose 1,5-bisphosphate carboxylase/oxygenase, which is expressed preferentially in the leaves and most especially the mesophyll tissues (Kuhlemeier et al., 1987, Ann Rev Plant Physiol 38: 221–257). It is also possible to use a specific promoter controlling, for example, an expression in the seeds or during a precise stage of development of the plant, or a promoter which is inducible following a thermal shock, a wound or interaction between the plant and parasites (Kuhlemeier et al., 1987, reference cited above), if an expression of recombinant DNA is desired in these situations.

The terminator sequence containing polyadenylation sites which can be isolated from plant genes or from genes which are expressed in plants, such as, for example, the nopaline synthase terminator *Agrobacterium tumefaciens*, is used.

The invention also relates to a bacterium, for example of the species *E. coli*, which contains the recombinant DNA defined above with the means needed for its replication and its expression. This bacterium may be used in the preparation of a protein having β-1,3-glucanase activity.

The invention also relates to a bacterium, for example of the species *E. coli*, which contains the recombinant DNA defined above with the means enabling it to be replicated, which bacterium may hence be used for the cloning of this recombinant DNA, and also to a bacterium capable of infecting a plant with transfer of genetic material, for example of one of the species *Agrobacterium rhizogenes* and *Agrobacterium tumefaciens*, which contains this DNA in a context enabling it to be replicated and may hence be used for transforming plant cells. The transformation of plant cells with the above recombinant DNA may also be performed by another biological method such as the pollen tube method (Zhong-xun Luo et al., Plant Molec. Biol. Rep., 1988, 6, 165–176) and the direct transformation of germinating seeds (Toepfer R. et al., 1989, The Plant Cell., 1, 133–139), or by a physical method such as the use of polyethylene glycol, electroporation (Chistou P. et al., 1987, Proc. Ntl. Acad. Sci. USA, 84, 3662–3699) and bombardment using microprojectiles (Klein T. M. et al., 1988, Proc. Ntl. Acad. Sci. USA, 85, 8502–8505).

The invention also relates to a plant cell, characterised in that it is transformed by the recombinant DNA defined above with the means needed for its expression. This plant cell can originate from a major crop species such as, for example, maize, soybean, beet, wheat, barley, poppy, rape, sunflower, alfafa and sorghum, a floral species such as rose, carnation and gerbera or a culinary species such as carrot, tomato, lettuce, chicory, pepper, melon and cabbage. Especially highly valued species are *Brassica napus* rape, *Helianthus annuus* sunflower and *Nicotiana tabacum* tobacco.

The step of transformation which involves one or a few cells is followed by a step of multiplication of these transformed cells so as to obtain calluses, which can give rise to transformed plants by processes of organogenesis or embryogenesis.

The invention hence also relates to a plant or plant part, characterised in that it contains the recombinant DNA defined above with the means needed for its expression. An especially highly valued plant part is the part capable of forming a complete new plant, in particular after sowing, burying in the ground or transplanting, or of producing seeds. Such a plant part is, for example, a grain, a mature fertilised ovule, a seed, a cutting, a runner, and the like. These plants can be any one of the above species, and more especially of the species *Nicotiana tabacum, Helianthus annuus* and *Brassica napus*.

The invention also relates to a method for obtaining plants resistant to parasites, such as phytopathogenic fungi, which comprises a step of transformation of plant cells with this recombinant DNA, followed by a step of multiplication of the transformed cells and a step of regeneration of the plants.

Preferably, the step of transformation of the plant cells is performed in vitro using an agrobacterium (that is to say a bacterium of the genus Agrobacterium) which has integrated recombinant DNA of interest.

The invention also relates to plants resistant to pathogenic agents, which are capable of being obtained using the method defined above.

The invention also relates to the use of a plant containing the recombinant DNA defined above with the means needed for its expression, as a parent in a selection programme for creating new plant varieties.

The invention also relates to a novel protein having β-1,3-glucanase activity, which comprises the sequence ($a_1$) (SEQ ID NO:1) and optionally, immediately downstream of the sequence ($a_1$), the sequence ($a_4$) (SEQ ID NO:2) truncated in its carboxy-terminal portion by 0 to 27 amino acids, and to a novel protein comprising the sequence ($a_5$) (SEQ ID NO:3).

This protein preferably possesses an apparent molecular mass of 36±3, 37±3 or 39±3 kDa.

This protein is of interest as an enzyme for conversion of biomass which contains β-1,3-glucans, in particular in some sectors of the papermaking industry and in the agri-foodstuffs industry, especially brewing.

The invention also relates to a method for preparing this protein, which comprises the culturing of bacteria, plant cells, plant calluses, plants or plant parts containing the recombinant DNA defined above, lysis thereof and isolation and purification of this protein.

A better understanding of the invention will be gained from the description below, divided into sections, which comprises experimental results and a discussion of the latter. Some of these sections relate to experiments performed with the object of carrying out the invention, and others to examples of embodiment of the invention which are naturally given purely by way of illustration.

A large part of the collective techniques below, which are well known to a person skilled in the art, is described in detail in the work by Sambrook et al.: "Molecular cloning: a Laboratory manual" published in 1989 by Cold Spring Harbor Press editions, New York (2nd edition).

BRIEF DESCRIPTION OF THE DRAWINGS

A better understanding of the description below will be gained by reference to FIGS. 1 to 7.

FIGS. 2A–2D show the nucleotide sequence (SEQ ID NO:11) of the HindIII-HindIII insert, part of the complementary DNA of soybean β-1,3-glucanase, the restriction sites used for cloning in M13mp19 and for the subsequent constructions being indicated by arrows, as well as the peptide sequence (SEQ ID NO:12) deduced from this complementary DNA.

FIGS. 3A–3D show the nucleotide sequence (SEQ ID NO:13) of the HindIII-HindIII fragment of the complementary DNA of soybean β-1,3-glucanase after mutagenesis (at the end of section 6c), the restriction sites used for cloning in M13mp19 and for the subsequent constructions being indicated by arrows, as well as the peptide sequence of the protein translated.

FIGS. 4A–4C show the nucleotide sequence (SEQ ID NO:15) of the NdeI-HindIII fragment of the coding portion of plasmid pBR59, an expression plasmid in *E. coli*, flanked by NdeI and HindIII restriction sites, and the peptide sequence (SEQ ID NO:16): of the protein translated.

FIGS. 5A–5E show the nucleotide sequence (SEQ ID NO:17) of the complete recombinant gene and the peptide sequence of (SEQ ID NO:18) of the protein translated.

FIGS. 6A–6B show the peptide sequence (SEQ ID NO:25) of the common portion of the proteins translated in *E, coli* and in tobacco.

FIGS. 7A and 7B show an alignment, on the basis of the method of Needleman and Wunsch, 1970, J. Mol. Biol. 48, 443–453, of the peptide sequence (SEQ ID NO:12) deduced from the complementary DNA of soybean β-1,3-glucanase (see FIGS. 2A–2D) and the closest known peptide sequence (SEQ ID NO:26), that deduced from the complementary DNA of *Nicotiana plumbaginifolia* β-1,3-glucanase (Swissprot data bank ref. Gub$-Nipl).

DETAILED DESCRIPTION OF THE INVENTION

Figure 1:
FIG. 1 shows a restriction map of the HindIII-EcoRI fragment contained in plasmid pBR 1310 and containing the complementary DNA coding for soybean β-1,3-glucanase.

Section1: Preparation of polyclonal antibodies against tobacco β-1,3-glucanase
a) Purification of tobacco β-1,3-glucanase.

A tobacco β-1,3-glucanase was purified to homogeneity from tobacco calluses as described below. Tobacco calluses were cultured in vitro on a Murashige and Skoog medium (Murashige T. and Skoog F., 1962, Physiol. Plant., 15, 473–497). Cell extracts are obtained by grinding the plant material in a 50 mM Tris-HCl buffer solution, pH 8.4, containing 15 mM β-mercaptoethanol and 5% of polyvinylpyrrolidone.

The protein is purified from this extract by ammonium sulphate precipitation, liquid chromatography on a cation exchange column based on synthetic polymer and exclusion chromatography (molecular sieving) on a crosslinked agarose, according to the protocol described below.

Step 1:

The protein extract is treated with ammonium sulphate (43% saturation). The proteins which have precipitated are collected by centrifugation (15,000 g for 30 min), solubilised in a buffer solution (100 mM ammonium acetate, pH 5.2) and dialysed overnight at 4° C. against a 100 mM ammonium acetate buffer solution, pH 5.2.

Immediately before proceeding, the acetate concentration of the buffer solution of the protein extract is brought to 10 mM by passage through ready-to-use minicolumns (Pharmacia PD-10).

Step 2:

The protein extract is then purified by ion exchange chromatography using a column based on synthetic polymer (Pharmacia Mono-S column) according to the Pharmacia FPLC technique.

The extract is applied to a Mono-S column equilibrated with a 10 mM ammonium acetate buffer, pH 5.2. The proteins retained on the column are eluted with a linear gradient from 10 to 500 mM ammonium acetate.

At each step, the β-1,3-glucanase is identified by its molecular weight (polyacrylamide gel electrophoresis in the presence Of SDS—visualisation with silver), and its activity is measured by a colorimetric method (see section 8 below) using laminarin (β-1,3-glucan extracted from *Laminaria digitataz*—Sigma—ref. L9634) as a substrate.

b) Preparation of polyclonal antibodies.

Rabbits were then injected with 25 μg of tobacco β-1,3-glucanase in 500 μl of Freund's complete adjuvant. Three booster injections of 25 μg in Freund's incomplete adjuvant (500 μl) were carried out at 3-week intervals. The immune serum was drawn 3 weeks after the final injection.

This immune serum recognises tobacco β-1,3-glucanase; it also recognises soybean β-1,3-glucanase. It was, in effect, verified that it enables the latter protein to be visualised by the Western blot technique (described in section 13 below) from an extract of total soybean (Glycine max cv Mandarin) proteins.

Section 2: Construction of a phage library of complementary DNA from messenger RNAs of soybean cell cultures.

a) Preparation of messenger RNAs of soybean cells.

The total RNA of 5-day-old soybean cells (Glycine max cv Mandarin), cultured in vitro in the absence of auxin according to the method described by Leguay et al., 1987, Develop. Genetics 8: 351–364, was extracted according to the method described by Jouanneau et al., 1984 Plant Physiol 74; 663–668, summarised below. The cells, washed beforehand in saline solution, are ground in liquid nitrogen; the homogenate is then extracted with a mixture of redistilled phenol and chloroform. After an ethanol precipitation step, the total RNA is dissolved in a solution buffered to pH 7.6.

The poly(A)$^+$ fraction of the messenger RNA (mRNA) was isolated after 2 cycles of affinity chromatography on an oligo(dT)-cellulose column as described in Sambrook et al., ("Molecular cloning: A Laboratory manual", second edition, Cold Spring Harbor Laboratory 1989). Quantification of the messenger RNAs is carried out by spectrophotometry according to a protocol well known to a person skilled in the art.

b) Synthesis of complementary DNAs

Complementary DNAs (cDNAs) were synthesised according to the method described by Gübler and Hoffman, 1983 (Gene, 25: 263–269), which method favours the synthesis and cloning of complete cDNAs: 7 μg of mRNA were treated in this manner for the manufacture of the first strand of cDNA using the Promega "Protoclone GT system" kit (ref. P3010).

c) Cloning of complementary DNAs.

The synthesised double-stranded cDNA is then methylated using EcoRI methylase under the conditions described in the reference work by Sambrook et al. (op. cit.). This enzyme enables the possible EcoRI sites of the cDNA to be protected against cleavage by the endonuclease EcoRI, this protection disappearing for the replicates of the cDNA (which are not methylated).

Synthetic EcoRI linkers (double-stranded DNA fragments containing the EcoRI site) are then added by ligation to the ends of the cDNA. After cleavage with the endonuclease EcoRI and removal of the linkers by chromatography on a column of G-50 molecular sieve (Pharmacia), the cDNA is ligated using T4 DNA ligase in phage lambda gt11, a cloning and expression vector described by Huynh et al., "DNA cloning: a practical approach" IRL Press, D. M. Glover 1985, p. 49, according to the Promega protocol (ref. T3011) "lambda gt11 system", the phage DNA being opened beforehand with the restriction endonuclease EcoRI and dephosphorylated. Aliquot portions of the ligation medium are then packaged in phage particles using the kit marketed by Amersham ("In vitro packaging system for lambda DNA", ref. N334).

The number of recombinants is then estimated by counting the lytic plaques obtained on a bacterial lawn of *E. coli* strain Y1090 (Sambrook et al., ref. above, op. cit.). Approximately $10^6$ clones were obtained. The plating out of an aliquot portion of the phage suspension on a bacterial lawn in the presence of X-gal (5-bromo-4-chloro-3-indolyl β-D-galactoside) and isopropyl β-D-thiogalactoside (IPTG), according to the technique described by Huynh et al., ref. above, enabled it to be determined that 81% of these phages integrated a soybean cDNA.

3: Section Immunological screening of the phage library of complementary DNA constructed from soybean cell messenger RNAs.

The production of a library in the vector lambda gt11 makes it possible to carry out the expression of the cloned cDNAs, that is to say to synthesise the proteins encoded by the messenger RNAs which were used for constructing this library. This synthesis takes place after induction with IPTG (isopropyl β-D-thiogalactoside); the synthesised proteins can then be recognised by the antibodies obtained against tobacco β-1,3-glucanase (see section 1). The clones producing these proteins can then be identified and isolated according to a protocol known to a person skilled in the art and described, for example, in Sambrook et al. (op. cit.).

$10^6$ phages of the soybean cDNA library are plated out on Petri dishes, and lytic plaques are obtained after 2 h 30 min of incubation at 42° C. A nitrocellulose filter (Schleicher and Schell, BA 85) impregnated with IPTG is placed on the surface of the dishes and left in contact with the agar medium for 4 h at a temperature of 37° C., and then replaced by a second filter which is left for 6 h on the same medium.

The filters removed from the dish are then immersed for 30 min in a solution, referred to as TNT solution, composed of 10 mM Tris-HCl, pH 8.0, 150 mM NaCl, 0.05% of Tween 20 detergent, and then for 30 minutes in a buffer, referred to as blocking buffer, composed of gelatin in 1% solution in TNT solution. The filters are then treated for 3 h in a solution containing the anti-β-1,3-glucanase polyclonal antibodies obtained above (see Section 1), diluted in the blocking buffer. They were then immersed for 10 minutes successively in each of the following solutions:

TNT solution+0.1% BSA (bovine serum albumin)

TNT solution+0.1% BSA+0.1% Nonidet P40 detergent (Sigma)

TNT solution+0.1% BSA.

The antigen-antibody complex formed is then visualised using secondary antibodies conjugated by coupling with a peroxidase ("Immuno conjugate GAR/IgG (H+L)/Po" of Nordic Immunology, Tilburg, Holland). The chemical visualisation reaction employs 4-chloro-1-naphthol as a chromogenic substrate (giving a blue precipitate). The positive lyric plaques, that is to say those corresponding to clones which synthesise β-1,3-glucanase, are then identified on the Petri dish, and the bacteriophages are removed and purified by means of a secondary immunological screening, performed in a strictly identical manner to the primary screening. One of these clones was selected for continuation of the study.

Section 4: Partial characterisation of the phage DNA of the soybean β-1,3-glucanase clone.

a) Preparation of phage DNA.

The selected phage clone is amplified and its DNA is extracted according to the protocol described in the Amersham kit "cDNA cloning system GT11" (ref. RPN 1280), summarised below. The phages are removed using a coring tool and transferred to a culture of $E.\ coli$ strain Y1090; after 15 min, 5 ml of Luria medium (Gibco) containing 5 mM of $CaCl_{12}$ and 50 μg/ml of ampicillin are added. After incubation for 4 h at 43° C. with agitation, the culture is centrifuged at 3,000 rpm for 10 min. The DNA of the phage particles present in the supernatant is then extracted and purified by treatment with polyethylene glycol and sodium chloride NaCl, centrifugation, treatment with proteinase K and precipitation.

b) Analysis of the phage DNA of the selected clones

DNA of the β-1,3-glucanase clones was hydrolysed with the restriction enzyme EcoRI. A single approximately 2,300-bp EcoRI-EcoRI fragment was thereby obtained by cleavage at the cloning sites. There is hence no EcoRI site in the complementary DNA.

Analysis by agarose gel electrophoresis of the fragments obtained by the action of several endonucleases on the approximately 2,300-bp EcoRI-EcoRI fragment enabled it to be shown that the latter contains a PvuII site a few base pairs from one of the EcoRI sites.

Section 5: Construction of plasmid pBR1310, isolation of the complementary DNA insert coding for soybean β-1,3-glucanase and determination of its sequence.

a) Cloning into plasmid pGEM-3Z

By hydrolysis of the clone selected using the restriction enzyme EcoRI and PvuII, the approximately 2,300 bp EcoRI-PvuII fragment containing the soybean β-1,3-glucanase cDNA was isolated after electrophoresis on low-melting-temperature agarose gel.

Plasmid pGEM-3Z (Promega, Madison, Wis, U.S.A.) was opened using the restriction endonucleases EcoRI and SmaI, then purified and isolated by electrophoresis on low-melting-temperature agarose gel. This plasmid comprises a "polylinker" (cloning multisite) successively containing EcoRI, SmaI and HindIII restriction sites.

Ligation using T4 DNA ligase of the approximately 2,300-bp EcoRI-PvuII fragment, containing the cDNA coding for soybean β-1,3-glucanase, into this plasmid thus opened enables a plasmid referred to as plasmid pBR1310 (ligation of the SmaI and PvuII blunt ends with disappearance of these sites) to be obtained, which plasmid is cloned into the $E.\ coli$ bacterium strain JM109 (Sambrook et al., op. cit.). The vector obtained was then extracted and purified by the alkaline lysis method (Birnboim and Doly, in Sambrook et al., op. cit.).

The use of several restriction enzymes made it possible to draw up the restriction map of the HindIII-EcoRI fragment contained in plasmid pBR1310 and containing the cDNA coding for β-1,3-glucanase, shown in FIG. 1.

The HindIII-HindIII fragment (of approximately 1490 bp) was prepared by the digestion of the HindIII-EcoRI fragment with the endonuclease HindIII, purified by electrophoresis on low-melting-temperature agarose gel and isolated. This fragment was cloned into the DNA of the replicative form of the single-stranded phage M13mp19 (Pharmacia) opened at the HindIII restriction site. The vector M13 containing the 1490-bp HindIII-HindIII insert is referred to as M13BR137. The sequence of this insert is determined according to the dideoxyribonucleotide method (Sanger et al., PNAS-USA, 14, 5463–5467, 1977).

b) Analysis of the cDNA sequence of soybean 62 -1,3-glucanase.

A better understanding of the description below will be gained with the aid of FIGS. 2A–2D.

This sequence contains a single open reading frame (not interrupted by a stop codon) compatible with the apparent molecular weight observed by agarose gel electrophoresis: the sequence beginning with an ATG codon at position 114 and terminating with the TAA stop codon at position 1224–1226 coding for a protein of 370 amino acids.

The University of Wisconsin's UWGCG software: Devereux et al., 1984, Nucl. Ac. Res., 12, 8711–8721- option: Testing for a signal peptide according to the method of G. von Heijne, 1986, Nucl. Ac. Res., 14, 483–490, provides in this sequence for a single portion coding for a signal peptide for an expression in eukaryotic cells, the following sequence ($Na_2$) referred to as a pre sequence (beginning at nucleotide 114 and terminating at nucleotide 209):

ATGCCTTCTC TCTTCGCTAG AAACCAGAGG TTCTCATTGG CTACTCTCCT
GCTTCTTCTG GAACTATTGA CAGGAAACCT TCGCATGGCA GATGCT coding for the signal peptide of 32 amino acids of the following sequence ($a_2$) (SEQ ID NO:7):

Met Pro Ser Leu Phe Ala Arg Asn Gln Arg Phe Ser Leu Ala
Thr Leu Leu Leu Leu Leu Glu Leu Leu Thr Gly Asn Leu Arg
Met Ala Asp Ala

A signal peptide is expected by a person skilled in the art, since β-1,3-glucanases are proteins which can be naturally either accumulated in the vacuoles of plant cells or secreted, thereby demanding the presence of a signal peptide.

The already-known peptide sequence closest to that of the protein of 370 amino acids deduced from the complementary DNA of soybean β-1,3-glucanase (SEQ ID NO:12) is that of the protein of 369 amino acids deduced from the complementary DNA of a *Nicotiana plumbaginifolia* β-1,3-glucanase (SEQ ID NO:22) (see Swissprot data bank ref. Gub$Nipl. and De Loose et al., 1988, Gene, 70, 13–23).

A comparison of these two sequences using the method of Needleman and Wunsch, 1970, J. Mol. Biol, 48,443–453, employed in the University of Wisconsin's UWGCG software: Devereux et al., 1984, Nucl. Ac. Res. 12,8711–8721, GAP option, shows that 224 amino acids are identical, equivalent to an approximately 60% homology. This algorithmic method considers all possible alignments and creates an alignment, shown in FIGS. 7A and 7B, in which the largest possible number of identical amino acids are paired and the number of holes in the aligned sequences is minimal. Comparison of the amino-terminal region of the predicted mature soybean β-1,3-glucanase with the published amino-terminal sequences of β-1,3-glucanases Four plant β-1,3-glucanases are known at present, the amino-terminal sequences of which have been determined experimentally. They are the β-1,3-glucanases of *Nicotiana tabacum* (H. Shinshi et al., 1988, Proc. Natl. Acad. Sci. USA 85, 5541–5545), of *Nicotiana plumbaginifolia* (M. De Loose et al., 1988, Gene, 70, 13–23), of *Phaseolus vulgaris* bean (B. V. Edington et al., 1991, Plant Molecular Biology, 16, 81–94) and of *Hordeum vulgare* barley (P. B. Hoj et al., 1988, Febs Lett., 230, 67–71).

Their amino-terminal sequences display a strong homology, of the order of 80% for the 15 amino-terminal amino acids. In the case of the dicotyledons (*Nicotiana tabacum, Nicotiana plumbaginifolia* and *Phaseolus vulgaris*), they all begin with a Gln followed, after a possible Ser, by the sequence Ile Gly Val Cys Tyr Gly (amino acid residues 1–6 of SEQ ID NO:12). It may be noted that the sequence of mature soybean (dicotyledon) β-1,3-glucanase predicted by the above software also begins with the sequence Gln Ile Gly Val Cys Tyr Gly (amino acid residues 1–6 of SEQ ID NO:12).

Section 6: Construction of a vector for expression in *E. coli*: plasmid pBR59.

a) Silent mutagenesis of the coding portion to remove the SacI restriction site (at position 575) of the coding portion.

The sequence GAG CTC of the SacI restriction site located at position 575 of the vector M13BR137 is replaced, by directed mutagenesis as described below, by the sequence GAG CAC. The codon GCT, corresponding to an alanine residue in the initial cDNA sequence, is hence replaced by the codon GCA, also corresponding to an alanine residue (silent mutation).

The single-stranded form of the vector M13BR137 is isolated according to the protocol described by Sambrook et al., op. cit., from a culture of the *E. coli* bacterial strain DH5αF' (Gibco-BRL) transformed beforehand with this vector according to the protocol recommended by the manufacturer. On this single-stranded template, mutagenesis is performed according to the protocol of the "Oligonucleotide-directed in vitro mutagenesis system" kit (Amersham—ref. RPN 1523—version 2), using an oligonucleotide synthesised chemically on the Millipore Biosearch 8700 DNA synthesiser, the sequence of which is shown below (SEQ ID NO:19):

GATCATGAAG GCCTTGTGCT CTTATTGCTT GG

The directed mutagenesis technique described in detail in the booklet accompanying this kit, and summarised below, consists in hybridising the above oligonucleotide with the single-stranded form of the vector M13BR137, and then in reacting Klenow polymerase and T4 DNA ligase in the presence of the thionucleotide dCTP-α-S (α-thiodeoxycytidine triphosphate) so as to obtain a circular double-stranded form of the recombinant phage, one of the strands of which carries the desired mutation and is protected from cleavage by the endonuclease NciI and degradation by exonuclease III. On the other strand (which has served as a template) a break is then introduced using the endonuclease NciI, and this strand is thereafter removed by the subsequent action of exonuclease III.

The resulting vector, referred to as vector M13BR138, was cloned into *E. coli* strain DH5αGF' and sequenced; it possesses, as expected, a sequence mutated by replacement of a codon GCT by a codon GCA, which has eliminated the SacI restriction site from the coding portion.

b) Mutagenesis of the 5' portion of the insert coding for soybean β-1,3-glucanase to introduce NdeI and BamHI restriction sites.

The single-stranded form of the vector M13BR138 is isolated as described above, and a directed mutagenesis is then carried out under the same conditions as before using the chemically synthesised oligonucleotide the sequence of which is noted below (SEQ ID NO:20)

GAGAAGGCAT GGATCCAAAC ATATGAATAC ACCAC

The vector derived from this mutagenesis, referred to as vector M13BR139, is cloned into the *E. coli* bacterial strain DH5αF'; it was sequenced, which confirmed the introduction of NdeI and BamHI restriction sites upstream of the ATG translation initiation codon.

c) Mutagenesis of the 3' portion of the insert of the vector M13BR139 to introduce HindIII and SacI restriction sites.

The single-stranded form of the vector M13BR139 is isolated, and a directed mutagenesis is then carried out on the 3' portion of the insert using the oligonucleotide of the following sequence and under the conditions already described SEQ ID NO:21:

CAGAGATTTT GAAGCTTAGG AGCTCAACCT TACACATC

The vector resulting from this mutagenesis, referred to as vector M13BR140, is cloned into the *E. coli* bacterial strain DH5αF'. Its sequence was determined, which confirmed the creation of HindIII and SacI restriction sites downstream of the TAA stop codon. This sequence is shown in FIGS. 3A–3D and in SEQ ID NO:13.

d) Construction of plasmid pBR141.

The replicative form of the vector M13BR140 is isolated and purified according to the protocol of Birnboim and Doly described in Sambrook et al., op. cit. The NdeI-HindIII insert containing the β-1,3-glucanase coding portion was isolated by digestion with the restriction enzymes NdeI and HindIII, and purified by agarose gel electrophoresis and electroelution (Sambrook et al., op. cit.). This insert is then ligated using T4 DNA ligase in the large NdeI-HindIII fragment of plasmid p373,2, the construction and constitutive elements of which are described in Patent Application EP-A-0,360,641 (FIGS. 3A–3D of this document shows the restriction map of this plasmid), opened beforehand by digestion with the restriction enzymes NdeI and HindIII. This large fragment contains, in particular, successively from the NdeI end to the HindIII end, a promoter analogous to the "tac" promoter (Sambrook et al., op. cit.) which is inducible with isopropyl β-D-galactoside, a gene coding for β-lactamase (conferring resistance to ampicillin) in a context permitting its expression, an origin of replication in *E. coli* and a transcription terminator derived from the phage fd. The vector obtained, referred to as plasmid pBR141, is cloned into *E. coli* strain RR1. The structure of the plasmid is verified by producing a restriction map.

e) Construction of plasmid pBR59

The plasmid DNA of the clone containing plasmid pBR141 is extracted according to the protocol of Birnboim and Doly (Sambrook et al., op. cit.).

Removal of the envisaged prokaryotic pre sequence (see section 5) of soybean β-1,3-glucanase is carried out by removal of the sequence comprised between the NdeI and SphI restriction sites and replacement of this sequence by the synthetic linker of sequence given below (SEQ ID NO:22):

```
TATGATTGGT GTGTGTTATG GCATGACTAA CCACACACAA
TACC
``` so as to re-form the sequence coding for the protein devoid of the signal peptide envisaged in prokaryotic cells, the first amino acid of this protein, namely the glutamine residue (capable of cyclising to pyroglutamate, which makes it impossible to determine the amino-terminal sequence), being replaced by a translation initiation methionine residue.

Ligation of this linker using T4 DNA ligase enables a plasmid, referred to as plasmid pBR59, to be obtained, which plasmid is cloned into the *E. coli* bacterial strain RR1. In this vector, the β-1,3-glucanase is under the control of a promoter (described in Patent Application EP-A-0,360,641) analogous to the "tac" promoter (Sambrook et al., op. cit.) which is inducible with isopropyl β-D-thiogalactoside (IPTG). The sequence of the coding portion of plasmid pBR59, flanked by the NdeI and HindIII sites, is shown in FIGS. 4A–4C and in SEQ ID NO:15.

Section 7: Expression of soybean β-1,3-glucanase in *E. coli*.

The *E. coli* strain RR1 containing the expression vector pBR59 and an *E. coli* strain RR1 containing plasmid p373,2 are cultured in Luria medium (Gibco) containing 100 mg/l of the antibiotic ampicillin overnight at 37° C. After a dilution of the culture to 1/100 in the same medium, the bacteria are returned to culture for 1 hour at 37° C. and IPTG is then added at a final concentration of 1 mM. Culturing is then continued for 3 hours and the bacteria are harvested by centrifugation.

The bacteria are resuspended in a buffer, referred to as loading buffer, of the following composition:

0.125M Tris-HCl, pH 6.8

4% sodium dodecyl sulphate

20% glycerol 0.02% bromophenol blue

10% β-mercaptoethanol and the mixture is then brought to 100° C. for 10 min (causing lysis of the bacteria and denaturation of the proteins). 10 µg of solubilised proteins are applied to a polyacrylamide electrophoresis gel according to the protocol described by Laemmli (U. K. Laemmli, Nature 227, 1970, 680–685). After electrophoresis, the gel is stained using Coomassie blue. The presence of three extra bands absent in the case of the control strain is noted in the case of the β-1,3-glucanase clone.

Section 8: Measurement of the enzymatic activity of the recombinant soybean β-1,3-glucanase expressed in *E. coli*, isolation and purification of three forms of this protein and determination of their amino-terminal sequences.

1. Measurement of the enzymatic activity of the recombinant β-1,3-glucanase.

β-1,3-glucanase activity is measured by a colorimetric method enabling the amount of monomers or oligomers liberated by the enzyme from a substrate (laminarin) to be estimated by determining the reducing power of the sugars thus liberated. This method, described by G. Ashwell, 1957, in "Methods in Enzymology III", 73–105, S. P. Colowick and N. U. Kaplan Eds., is summarised below.

50 µl of a solution containing 50 mg/ml of laminarin (β-1,3-glucan extracted from *Laminaria digitata*—Sigma—ref. L9634) are added to a solution containing a concentration of β-1,3-glucanase chosen so as to fall within a linear response range. The volume of the reaction mixture is adjusted to 500 µl using a 0.2M sodium acetate buffer solution, pH 5.0. After incubation for one hour at 40° C., a 200 µl aliquot portion is added to 200 µl of Somogyi's reagent (mixture of 25 ml of an aqueous solution comprising 2.5% of $Na_2CO_3$, 2.5% of $KNaC_4H_4O_6.4H_2O$, 2% of $NaHCO_3$, 20% of $Na_2SO_4$ and 1 ml of aqueous solution containing 15% of $CuSO_4.5H_2O$) and then brought to 100° C. for 45 min. The tubes are then cooled in ice before adding 200 µl of Nelson's reagent (aqueous solution of 5.5% of ammonium molybdate, 4.6% of concentrated sulphuric acid and 12% of $Na_2SO_4.7H_2O$).

The volume of the mixture is adjusted to 5 ml with distilled water and its absorbance is measured by spectrophotometry at a wavelength of 500 nm.

The amount of reducing sugars liberated is estimated by comparison with the absorbance values obtained with a calibration series established using a glucose solution. The β-1,3-glucanase enzymatic activity is expressed in nanomoles of glucose equivalent liberated per minute under the conditions of the enzymatic test described above.

2. Isolation and purification of three forms of recombinant β-1,3-glucanase:

a) Method

The different forms of the recombinant protein were isolated and purified from the centrifugate obtained in section 7 (end of the first paragraph). The isolation and purification comprise steps of extraction, ammonium sulphate precipitation, FPLC liquid chromatography on a cation exchange column based on synthetic polymer and exclusion chromatography (molecular sieving) on a crosslinked agarose, according to the protocol described below:

STEP 1:

The bacterial pellet is treated with agitation at 4° C. with a pH 8 buffer solution (30 mM Tris, 1 mM EDTA). After centrifugation (15,000 g, 30 min), the supernatant collected (lysate) constitutes the crude extract.

STEP 2:

The protein extract is precipitated with ammonium sulphate (60% saturation). The proteins which have precipitated are collected by centrifugation (15,000 g for 30 min), solubilised in a buffer solution (100 mM ammonium acetate, pH 5.2) and dialysed overnight at 4° C. against a 100 mM ammonium acetate buffer solution, pH 5.2.

Immediately before proceeding, the concentration of the buffer solution of the protein extract is brought to 10 mM by passage through ready-to-use minicolumns (Pharmacia PD-10).

STEP 3:

The protein extract is then purified by ion exchange chromatography on a column based on synthetic polymer (Pharmacia Mono-S column) according to the Pharmacia FPLC technique.

The extract is applied to the Mono-S column equilibrated with a 10 mM ammonium acetate buffer, pH 5.2. The proteins retained on the column are eluted with a linear gradient from 10 to 500 mM ammonium acetate.

STEP 4:

The fractions containing a β-1,3-glucanase activity are concentrated by ultrafiltration on a Centricon 10 concentration cartridge (Amicron). The purification of the protein is continued by chromatography (molecular sieving) on a crosslinked agarose (Pharmacia Superose 12 column). Elution is carried out with a 500 mM ammonium acetate buffer, pH 5.2.

At each step, the different forms of recombinant β-1,3-glucanase are identified by their molecular weight (polyacrylamide gel electrophoresis in the presence of SDS—visualisation with silver), by their activities measured by the colorimetric method described above and by their positive reactions with the polyclonal antibodies directed towards tobacco β-1,3-glucanase prepared in section 1.

b) Results

Three forms of the recombinant protein possessing a β-1,3-glucanase activity, of apparent molecular weights 36±3, 37±3 and 39±3 kDa, are thereby isolated and purified. (The molecular weight of the protein deduced from the coding sequence is 37,387 Da). Their respective measured specific activities are 1.65, 1.75 and 1.76 nanomoles of glucose equivalent liberated per minute per microgram of proteins, values which are not significantly different.

3. Determination of the amino-terminal sequence of the three forms of recombinant β-1,3-glucanase.

Sequencing of the amino-terminal ends of the three forms of recombinant β-1,3-glucanase was carried out. The samples to be treated are brought to the surface of a PVDF (polyvinylidene difluoride) filter, which is introduced into a protein sequencer (Model 470 A, marketed by the company Applied Biosystems USA) equipped with a chromatograph (Applied Biosystems Model 430) which continuously analyses the phenylthiohydantoin derivatives formed, after each degradation cycle.

The respective amino-terminal sequences determined are shown below, the symbol X representing an amino acid not determined (SEQ ID NOS:23, 24, and 24, respectively):

---

Met Ile Gly Val X Tyr Gly Met Leu
Met Ile Gly Val X Tyr Gly Met Leu Gly Asn Asn Leu Pro
Met Ile Gly Val X Tyr Gly Met Leu Gly Asn Asn Leu Pro

---

These sequences correspond to the sequence deduced from the coding portion of plasmid pBR59 (see FIGS. 4A–4C). There is hence no post-translational maturation of the amino-terminal portion. The observed differences in molecular weight for a similar specific activity are hence probably the result of a carboxy-terminal post-translational maturation which occurs on 27 amino acids approximately.

Section 9: Construction of a vector for expression in plant cells: the binary vector pBR60.

a) Preparation of a complete recombinant gene for soybean β-1,3-glucanase and cloning thereof into the binary vector pBIN19.

The DNA carrying the coding sequence was obtained by cleavage of the vector M13BR140, obtained in section 6c) (see FIGS. 3A–D and SEQ NO:13), using the restriction enzymes BamHI and SacI, and purified by electrophoresis on low-melting-temperature agarose gel. This DNA was inserted between a promoter sequence comprising so-called 35S promoter of the cauliflower mosaic virus (35S CaMV) and a terminator sequence comprising the nopaline synthase terminator of Agrobacterium tumefaciens.

b) Preparation of the promoter sequence comprising the 35S promoter of the cauliflower mosaic virus.

The approximately 900-bp HindIII-BamHI fragment containing the 35S promoter is isolated from plasmid pBI121 (Clontech) by cleavage using the endonucleases HindIII and BamHI followed by agarose gel electrophoresis. This fragment is cut again with HindII. The approximately 410-bp fragment carrying the BamHI site is treated with T4 DNA ligase in the presence of a HindIII linker (synthetic sequence containing a HindIII site). After cleavage with the endonuclease HindIII and agarose gel electrophoresis, the resulting HindIII-BamHI fragment (of approximately 420-bp) is isolated and purified.

c) Preparation of the terminator sequence comprising the nopaline synthase (NOS) terminator of Agrobacterium tumefaciens.

An approximately 250-bp fragment containing the nopaline synthase terminator was isolated from plasmid pBI121 (Clontech) by cleavage using the restriction enzymes SacI and EcoRI followed by agarose gel electrophoresis.

The promoter sequence, the coding sequence of the complementary DNA of β-1,3-glucanase and the terminator sequence were ligated using T4 DNA ligase in the binary vector pBIN19 opened using the endonucleases HindIII and EcoRI. This vector carries two genes for resistance to kanamycin, one capable of being expressed in bacteria, and the other, located immediately upstream of the complete recombinant gene (see Bevan, 984, Nucl. Ac. Res., 12, 8711–8721), capable of being transferred to plant cells. The gene for resistance to kanamycin will serve as a selection marker during the steps of transformation and analysis of the progeny of the transformed plants.

The vector obtained is referred to as plasmid pBR60. The nucleotide sequence of the complete recombinant gene, verified by sequencing, together with the peptide sequence deduced are shown in FIGS. 5A–5E. The plasmid is cloned into E. coli strain MC1061 (Clontech).

Section 1: Transfer into Agrobacterium tumefaciens of plasmid pBR60 containing the recombinant gene for β-1,3-glucanase.

a) Transfer into Acrobacterium tumefaciens.

This transfer is carried out as described below by three-way conjugation between the E. coli strain MC1061 containing the vector pBR60 and Agrobacterium tumefaciens strain LBA4404 (Clontech) using E. coli strain HB101 containing the mobilising plasmid pRK2013 (D. M. Figurski et al., 1979, Pro. Ntl. Ac. Sci. USA, 76, 1648–1652).

The E. coli strain MC1061 containing plasmid pBR60 and an E. coli strain HB101 (Clontech) containing the mobilising plasmid pRK2013 are cultured at 37° C. in Luria medium (Gibco) in the presence of 25 mg/l of kanamycin. Agrobacterium tumefaciens strain LBA4404 is cultured at 28° C. in Luria medium (Gibco) in the presence of 100 mg/l of rifampicin (it is resistant to this antibiotic); 200 μl of each of the three cultures are mixed, plated out on Luria agar medium (Gibco) and incubated overnight at 28° C. The bacteria are then resuspended in 5 ml of Luria medium and aliquot portions are plated out on Petri dishes containing an agar minimum medium (described in 'Plant Molecular Biology Manual" Gelvin et al., Kluwer Academic Press, 1988) in the presence of 100 mg/l of rifampicin and 25 mg/l of kanamycin. Under these conditions, only Agrobacterium tumefaciens colonies which have integrated plasmid pBR60 grow (E. coli strains cannot grow under these conditions). These colonies contain the recombinant gene for β-1,3-glucanase in a context permitting its replication.

The resistance of the selected colonies to both antibiotics is verified by transplanting them on the same selection medium twice in succession. The presence of the recombinant gene for β-1,3-glucanase in Agrobacterium tumefaciens is verified by the Southern blot method on a total DNA preparation (cell lysis, purification of the DNA by extraction using a phenol/chloroform mixture, according to the protocol described by Gelvin in the work cited above, cleavage of the purified DNA using restriction enzymes, agarose gel electrophoresis, transfer onto a membrane and hybridisation according to techniques well-known to those skilled in the art).

b) Transfer into *Agrobacterium rhizogenes*

This transfer is carried out in the same manner as the transfer into *Agrobacterium tumefaciens* described in a), with *Agrobacterium rhizogenes* strain A4 described by GUERCHE et al., (1987) Mol. gen. genet. 206, 382.

Section 11: Obtaining transformed tobacco plants

*Nicotiana tabacum* tobacco cultured in vitro was infected with *Agrobacterium tumefaciens* containing plasmid pBR60 according to the procedure of Horsch et al., well-known to a person skilled in the art (Horsch R. B. et al., 1985, Science 227, 1229–1231), the main steps of which are described below.

Discs of axenic *N. tabacum* tobacco plants (variety Wisconsin Havana 38, sensitive to pathogenic fungi) are incubated in a culture of *A. tumefaciens* harbouring plasmid pBR60. The discs, drained on Whatman paper, were transferred onto culture media in Petri dishes in order to multiply the transformed cells so as to obtain calluses, and then to produce buds in the presence of cefotaxime (500 μg/ml), which is designed to remove *Agrobacterium tumefaciens*, and kanamycin (100 μg/ml).

Buds resistant to kanamycin were then transferred onto a medium permitting the induction of roots in the presence of cefotaxime and kanamycin. The plantlets are then transplanted into pots in a substrate composed of peat and compost, and left to grow in a greenhouse. All the transformed plants (R0 generation) which survived the steps of regeneration and acclimatisation in the greenhouse proved morphologically normal and fertile. They were self-fertilised and gave seeds (R1 generation).

Section 12; Analysis of the genomic DNA of the transformed tobacco plants (R0 generation) according to the Southern blot technique.

The high molecular weight genomic DNA was isolated from mature leaves of transgenic plants of the R0 generation according to the method of extraction using cetyltrimethylammonium bromide and of purification by precipitation, described in the work "Plant Molecular Biology Manual" already cited.

10 μg of this genomic DNA were digested overnight at 37° C. with 20 units of the restriction enzymes HindIII and EcoRI. The restriction fragments obtained were separated by electrophoresis on agarose gel (1%). The DNA was transferred according to the Southern blot method onto a Nylon filter (Amersham Hybond N+), and hybridised with a nucleotide probe comprising a portion of the sequence of the recombinant gene, labelled by coupling to peroxidase (ECL kit, Amersham). The membranes are then washed and visualised according to the protocol recommended by Amersham.

Analysis of the films enables the following conclusions to be drawn:

some plants do not possess copies of the transferred recombinant gene (absence of signal), most of the plants tested contain at least one copy without rearrangement of the construction: 35S CaMV promoter—coding sequence of the complementary DNA of β-1,3-glucanase—NOS terminator, some profiles suggest that there are internal rearrangements in the construction, but these events are rare.

Section 13: Demonstration of the expression of soybean β-1,3-glucanase in transformed tobacco plants (of R0 generation).

a) Preparation of crude protein extracts of transformed tobacco plants (R0 generation).

Crude protein extracts were prepared from various plant tissues (root, stem, leaf, and the like). The tissue fragments were frozen in liquid nitrogen, reduced to powder and stored at -20° C. The powder was extracted at 4° C. in the presence of a 0.1M ammonium acetate buffer, pH 5.2, and subjected to a centrifugation at 10,000 g. The total protein concentration was determined on the supernatants, hereinafter referred to as crude protein extracts, following the technique of Bradford (Bradford, M. M., 1976, Anal. Biochem., 72, 248–254).

b) Demonstration by immunoblotting (Western blot)

The crude protein extracts of different transformed plants and of untransformed (control) plants are subjected to a Western blot, a technique well-known to a person skilled in the art and described, in particular, by H. Towbin et al., Proc. Ntl. Acad. Sci. USA, 76, 1972, 4350–4354, which comprises the following steps:

denaturation by heating to 100° C. for 10 min in a buffer, called loading buffer, consisting of 0.125M Tris-HCl, pH 6.8, 4% SDS, 0,002% bromophenol blue, 20% glycerol, 10% β-mercaptoethanol (according to the protocol described by Laemmli, U. K. Laemmli, Nature, 227, 1970, 680–685);

electrophoretic separation of the different proteins contained in the solubilisate according to the protocol described by Laemmli (ref. above);

electrotransfer of the said proteins contained in the gel onto a PVDF membrane (according to the technique of H. Towbin et al., Proc. Natl. Acad. Sci. USA 76, 1979, 4350–4354).

Immunodetection is carried out according to a protocol which comprises the following steps:

saturation of the PVDF membrane onto which the proteins have been transferred by incubation for not less than 2 hours at 37° C. in a 3% solution of gelatin, 3 washes in phosphate-buffered saline containing 0.05% of Tween 20 detergent, incubation (for 1 hour at 37° C.) in the presence of the immune serum prepared above (containing polyclonal antibodies which recognise the recombinant protein) diluted to 1/10,000 in phosphate-buffered saline, 3 washes in phosphate-buffered saline containing 0.05% of Tween 20 detergent.

The antigen-antibody complex is then visualised using an alkaline phosphatase-conjugated streptavidin/biotin system with the Amersham kit RPN 23 ("Blotting detection kit"), used according to the manufacturer's directions.

The blot obtained shows the presence of a protein of approximately 37±3 kDa for the transformed plants which is absent from the control plants (the protein deduced from cDNA sequence, from which its assumed signal peptide for an expression in eukaryotic cells has been cleaved, has a molecular weight of 38,156 Da).

Analysis according to the Western blot technique was performed on 30 transformed plants (responding positively to Southern blot). 28 plants showed an expression of the recombinant β-1,3-glucanase in Western blot.

c) Comparison of the electrophoretic migrations of soybean β-1,3-glucanases (recombinant proteins and natural protein).

The apparent molecular weight obtained for the recombinant protein expressed in the transformed tobacco plants was compared with that obtained for the natural protein present in an extract of soybean cells (see section 1) and natural tobacco β-1,3-glucanase present in an extract of tobacco cells (see section 1), by electrophoretic migration on parallel lanes according to the protocol described by Laemmli (U. K. Laemmli, Nature 227, 1970, 680–685). The sizes of these proteins were compared with those of proteins of known molecular masses (molecular weight markers of between 14,000 and 97,400 Da of Bio-Rad—ref. 61–0304).

The blots obtained after Western blot show that soybean β-1,3-glucanase synthesised in tobacco possesses the same apparent molecular weight as that of the natural soybean protein: 37±3 kDa. The post-translational maturation of this protein is hence performed in the same manner in a plant other than soybean. This apparent molecular weight of soybean β-1,3-glucanase is approximately 3 kDa higher than that of tobacco β-1,3-glucanase, whose molecular weight is 34,969 Da (H. Shinshi et al., 1988, Proc. Natl. Aca. Sci. USA, 85, 5541–5545). The molecular weight of soybean β-1,3-glucanase is hence in the region of 38 kDa, which is very close to the molecular weight predicted in section 5 for the mature protein of 338 amino acids predicted in section 5, which is 38,156 Da.

Section.14: Measurement of the resistance of transformed formed tobacco plants (R1 generation) to pathogenic fungi.

Tobacco plants regenerated (R0 generation) in the presence of kanamycin were self-pollinated. The mature seeds (R1 generation) are sown on Murashige and Skoog medium supplemented with 100 μg/ml of kanamycin.

The kanamycin-resistant plantlets of the R1 generation, derived from 13 chosen transformed plants, from a *Nicotiana tabacum* var. Wisconsin Havana 38 plant sensitive to the fungus *Chalara elegans* (also known as *Thielaviopsis basicola*), abbreviated to W38, were transferred to the greenhouse for evaluation of their resistance to this fungus. The latter was chosen since it is representative of the pathogenic fungi of tobacco possessing β-1,3-glucans in their wall. The study covered numbers of plantlets varying from 16 to 25 depending on the progeny of the transformed plants. The protocol chosen in this study is described below:

The plantlets are cultivated in pots (3×3 cm). On appearance of the 5th leaf, the plants are inoculated by depositing a suspension of $5 \times 10^5$ endoconidia of this fungus on the neck.

The endoconidia are taken from mycelial cultures of this fungus maintained on potato dextrose agar medium (Difco) at 22° C. and in the dark. The resistance to *Chalara elegans* is evaluated 45 days after inoculation.

The plants are scored according to the symptoms of infection and according to their level of vegetative development.

Two scorings are implemented:

Measurement of the weight (in grams) of the aerial parts of the plants

Measurement of a resistant index taking into account the impact of the disease on the whole of the plant.

The classes are defined according to the following criteria:

Score 0: plant dead

Score 1: terminal bud still green, root system destroyed

Score 2: development of the plants not exceeding 25% of that of the control, root system completely necrotic Score 3: development of the plants attaining 50% of the development of the control, root system displaying healthy portions Score 4: development of the plants identical to the control.

The resistance index of the progeny of a transformed plant represents the mean of the scores assigned to the plantlets derived from this plant.

The table below collates the main results obtained:

TABLE 1

Measurement of the resistance of progeny of transformed tobacco plants to pathogenic fungi

| | Number tested | Resistance Index | Weight of the aerial parts |
|---|---|---|---|
| Transformed plants | | | |
| No. 5 | 24 | 1 | 0.22 |
| No. 10 | 23 | 0.87 | 0.22 |
| No. 17 | 21 | 1.04 | 0.29 |
| No. 20 | 17 | 1.41 | 0.50 |
| No. 22 | 23 | 1 | 0.35 |
| No. 29 | 19 | 1.1 | 0.46 |
| No. 30 | 16 | 0.5 | 0.14 |
| No. 37 | 20 | 0.25 | 0.46 |
| No. 43 | 25 | 0.56 | 0.075 |
| No. 45 | 23 | 0.30 | 0.65 |
| No. 49 | 21 | 0.19 | 0.72 |
| No. 55 | 22 | 0.09 | 0.05 |
| No. 59 | 25 | 0.48 | 0.14 |
| Control plants | | | |
| W38 | 25 | 0.12 | 0.06 |

W38: Untransformed *Nicotiana tabacum* var. Wisconsin Havana 38 plant

It is seen on studying the above table that 12/13 of the progeny of transformed tobacco plants have a resistance index and a weight of the aerial parts which are higher than those of the progeny of the untransformed W38 plant.

The transformation of tobacco plants with the recombinant DNA of the invention hence confers on their progeny an increased resistance to pathogenic fungi.

Section 15: Purification of the recombinant β-1,3-glucanase from the leaves of transformed tobacco plants (R1 generation) and determination of its amino-terminal sequence.

1) Purification of the recombinant β-1,3-glucanase

The recombinant protein was purified from crude extracts of transformed tobacco leaf proteins, by ammonium sulphate precipitation and FPLC liquid chromatography on a cation exchange column based on synthetic polymer on a crosslinked agarose, according to the protocol described below:

Protocol for purification of the recombinant β-1,3-glucanase

STEP 1: The protein extract is precipitated with ammonium sulphate (60% saturation). The proteins which have precipitated are recovered by centrifugation (15,000 g for 30 min), solubilised in a buffer solution (100 mM ammonium acetate, pH 5.2) and dialysed overnight at 4° C. against a 100 mM ammonium acetate buffer solution, pH 5.2.

Immediately before proceeding, the concentration of the buffer solution of the protein extract is brought to 10 mM by passage through ready-to-use minicolumns (Pharmacia PD-10).

STEP 2: The protein extract is then purified by ion exchange chromatography based on synthetic polymer (Pharmacia Mono-S column) using an FPLC technique (Pharmacia).

The extract is applied to the Mono-S column equilibrated with a 10 mM ammonium acetate buffer, pH 5.2. The proteins retained on the column are eluted with a linear gradient from 10 to 500 mM ammonium acetate.

At each step, the soybean β-1,3-glucanase is identified by its molecular weight (polyacrylamide gel electrophoresis in the presence of SDS—visualisation with silver), and by its immunoblot (see Section 13b)) and its activity, measured by the colorimetric method described in Section 8 1).

2) Determination of the amino-terminal sequence of the recombinant β-1,3-glucanase After purification of the recombinant β-1,3-glucanase according to the protocol described above, sequencing of the amino-terminal end was carried out. The samples to be treated are brought to the surface of a PVDF (polyvinylidene difluoride) filter by electrotransfer according to the method described by H. TOWBIN et al. Proc. Ntl. Acad. Sci. USA (1979), 4350–4354, after polyacrylamide gel electrophoresis in the presence of SDS. The filter is introduced into a protein sequencer (model 470 A marketed by the company Applied Biosystems (USA)) equiped with a chromatograph (Applied Biosystems model 430) which continuously analyses the phenylthiohydantion derivatives formed, after each degradation cycle.

It was not possible to determine an amino-terminal sequence, despite the good operation of the sequencer, checked by the determination of the amino-terminal sequence of a control protein: the lactoglobulin.

It is thus probable that the amino-terminal sequence of the recombinant β-1,3-glucanase begins with a Gln, as predicted by comparison of the already determined amino-terminal sequences of dicotyledons (see section 5).

It has indeed already been shown that the amino-terminal Gln was blocked for another soybean β-1,3-glucanase (TAKEUCHI et al., 1990, Plant Physiol. 93, 673–682).

Section 16: Obtaining transformed rape plants.

The transformation is carried out according to the protocol of P. Guerche et al. (P. Guerche et al., 1987, Mol. Gen. Genet., 206, 382). The different culture media are those described by Pelletier et al. (Pelletier et al., 1983, Mol. Gen. Genet., 191, 244). Their composition is detailed below (Table 2).

a) Obtaining transformed roots.

Stem segments are removed from the apical tip of rape plants (*Brassica napus*: spring varieties Brutor and Westar and winter variety) approximately 1 m in height. These segments are surface sterilised, rinsed in sterile water, cut into segments 1.5 cm in length approximately and placed in a tube containing medium A.

Inoculation of the tip of this segment is performed by application of a suspension of the *Agrobacterium rhizogenes* strain containing plasmid pBR60.

Transformed roots appear on the stem segment after 1 to 2 weeks; they are removed and placed on agar medium B (15 g/l) supplemented with 500 μg of cefotaxime/ml.

b) Regeneration of transformed plants.

Root fragments are incubated for 15 days on medium D containing 3 mg/l of 2,4-dichlorophenoxyacetic acid, and then placed on RCC medium for induction of buds. Rooted plants are then obtained by passage of the buds through media F and G.

Section 17: Demonstration of the expression of soybean β-1,3-glucanase in transformed rape plants.

a) Preparation of crude protein extracts of transformed rape plants (R0 generation)

Crude protein extracts were prepared from leaves of the plant. These extracts were frozen in liquid nitrogen, reduced to powder and stored at −20° C. The powder was extracted at 4° C. in the presence of a 0.4M ammonium acetate buffer, pH 5.2, and subjected to a centrifugation at 10,000 g. The total protein concentration was determined on the supernatants, hereinafter referred to as crude protein extracts, following the technique of Bradford (Bradford, M. M., 1976, Anal. Biochem., 72,248–254).

b) Demonstration by immunoblotting (Western blot)

The crude protein extracts of different transformed plants and of untransformed (control) plants are subjected to a Western blot, a technique well-known to a person skilled in the art and described above.

The antigen-antibody complex is then visualised using an alkaline phosphatase-conjugated streptavidin/biotin system with Amersham kit RPN 23 ("Blotting detection kit"), used according to the manufacturer's directions.

The blot obtained shows the presence of a protein of approximately 37±3 kDa for the transformed plants, which is absent from the control plants.

Analysis according to the Western blot technique was performed on 30 transformed plants (responding positively to Southern blot). 38 plants showed an expression of the recombinant β-1,3-glucanase in Western blot.

TABLE 2

Composition of the different media used for obtaining transformed rape plants

| Composition (mg/l) | Medium | | | | |
|---|---|---|---|---|---|
| | A | B | RCC | F | G |
| $NH_4NO_3$ | 1,650 | | 1,650 | 1,650 | 825 |
| $KNO_3$ | 1,900 | 2,500 | 1,900 | 1,900 | 950 |
| $(NH_4)_2SO_4$ | | 134 | | | |
| $NaH_2PO_4$ | | 150 | | | |
| $KH_2PO_4$ | 170 | | 170 | 170 | 85 |
| $CaCl_2.2H_2O$ | 440 | 750 | 440 | 440 | 220 |
| $MgSO_4.7H_2O$ | 370 | 250 | 370 | 370 | 185 |
| $H_3BO_3$ | 12.4 | 3 | 12.4 | 6.2 | 6.2 |
| $MnSO_4.4H_2O$ | 33.6 | 10 | 33.6 | 22.3 | 22.3 |
| $ZnSO_4.7H_2O$ | 21 | 2 | 21 | 8.6 | 8.6 |
| KI | 1.66 | 0.75 | 1.66 | 0.83 | 0.83 |
| $Na_2MoO_4.2H_2O$ | 0.5 | 0.25 | 0.5 | 0.25 | 0.25 |
| $CuSo_4.5H_2O$ | 0.05 | 0.025 | 0.05 | 0.25 | 0.25 |
| $CoCl_2.6H_2O$ | 0.05 | 0.025 | 0.05 | 0.25 | 0.25 |
| $FeSO_4.7H_2O$ | 22.24 | 27.8 | 27.8 | 27.8 | 22.24 |
| $Na_2EDTA$ | 29.84 | 37.3 | 37.3 | 37.3 | 29.84 |
| Inositol | 100 | 100 | 100 | 100 | 100 |
| Nicotinic acid | 0.5 | 1 | 0.5 | 1 | 0.5 |
| Pyridoxine HCl | 0.5 | 1 | 0.5 | 1 | 0.5 |
| Thiamine | | 10 | | 10 | |
| Glycine | 2 | | 2 | | 2 |
| Glucose | 10,000 | 20,000 | | | 10,000 |
| Sucrose | 10,000 | | 10,000 | 10,000 | |

TABLE 2-continued

Composition of the different media used for obtaining transformed rape plants

| Composition (mg/l) | Medium | | | | |
|---|---|---|---|---|---|
| | A | B | RCC | F | G |
| D-mannitol | | 70,000 | 10,000 | | |
| NAA | | 1 | 1 | 0.1 | 0.1 |
| BA | | 1 | 0.5 | 0.5 | |
| 2,4D | | 0.25 | | | |
| Adenine sulphate | | | | | |
| IPA | | | 0.5 | | |
| $GA_3$ | | | 0.02 | | |
| Tween 80 | | 10 | | | |
| Agar | 8,000 | | 8,000 | 8,000 | 8,000 |
| pH | 5.8 | 5.8 | 5.8 | 5.8 | 5.8 |
| Gentamicin (sulphate) | 10 | | | | |

NAA = naphthaleneacetic acid
BA = 6-benzylaminopurine
2,4D = 2,4-dichlorophenoxyacetic acid
IPA = $N^6$-(2-isopentenyl)adenine
$GA_3$ = gibberellic acid
EDTA = ethylenediaminetetraacetic acid

---

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 309 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Ile Gly Val Cys Tyr Gly Met Leu Gly Asn Asn Leu Pro Ser Ala Asn
 1               5                  10                  15

Asp Val Ile Gly Leu Tyr Arg Ser Asn Asn Ile Lys Arg Met Arg Leu
                20                  25                  30

Tyr Asp Pro Asn Gln Ala Ala Leu Glu Ala Leu Arg Asn Ser Gly Ile
            35                  40                  45

Glu Leu Ile Leu Gly Val Pro Asn Ser Asp Leu Gln Gly Leu Ala Thr
    50                  55                  60

Asn Pro Asp Thr Ser Arg Gln Trp Val Gln Lys Asn Val Leu Asn Phe
65                  70                  75                  80

Trp Pro Ser Val Lys Ile Lys Tyr Val Ala Val Gly Asn Glu Val Ser
                85                  90                  95

Pro Val Gly Gly Ser Ser Ser Val Ala Gln Tyr Val Leu Pro Ala Ile
                100                 105                 110

Gln Asn Val Tyr Gln Ala Ile Arg Ala Gln Gly Leu His Asp Gln Ile
            115                 120                 125

Lys Val Ser Thr Ser Ile Asp Met Thr Leu Ile Gly Asn Ser Phe Pro
            130                 135                 140

Pro Ser Gln Gly Ser Phe Arg Gly Asp Val Arg Ser Tyr Leu Asp Pro
145                 150                 155                 160
```

```
Ile  Ile  Gly  Tyr  Leu  Val  Tyr  Ala  Asn  Ala  Pro  Leu  Leu  Val  Asn  Val
               165                     170                          175

Tyr  Pro  Tyr  Phe  Ser  Tyr  Thr  Gly  Asn  Pro  Arg  Asp  Ile  Ser  Leu  Pro
               180                     185                          190

Tyr  Ala  Leu  Phe  Thr  Ala  Pro  Asn  Val  Val  Val  Trp  Asp  Gly  Gln  Tyr
               195                     200                          205

Gly  Tyr  Gln  Asn  Leu  Phe  Asp  Ala  Met  Leu  Asp  Ser  Val  His  Ala  Ala
          210                     215                     220

Ile  Asp  Asn  Thr  Lys  Ile  Gly  Tyr  Val  Glu  Val  Val  Val  Ser  Glu  Ser
225                      230                     235                          240

Gly  Trp  Pro  Ser  Asp  Gly  Gly  Phe  Ala  Ala  Thr  Tyr  Asp  Asn  Ala  Arg
               245                     250                          255

Val  Tyr  Leu  Asp  Asn  Leu  Val  Arg  Arg  Ala  Asn  Arg  Gly  Ser  Pro  Arg
               260                     265                          270

Arg  Pro  Ser  Lys  Pro  Thr  Glu  Thr  Tyr  Ile  Phe  Ala  Met  Phe  Asp  Glu
               275                     280                          285

Asn  Gln  Lys  Asn  Pro  Glu  Ile  Glu  Lys  His  Phe  Gly  Leu  Phe  Asn  Pro
          290                     295                     300

Asn  Lys  Gln  Lys  Lys
305
```

(2) INFORMATION FOR SEQ ID NO:2:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:2:

```
Tyr  Pro  Phe  Gly  Phe  Gly  Gly  Lys  Arg  Leu  Gly  Lys  Val  Val  Ile  Asp
1                    5                     10                          15

Asp  Phe  Asn  Ala  Thr  Thr  Ser  Ile  Lys  Ser  Asp  Val
               20                     25
```

(2) INFORMATION FOR SEQ ID NO:3:

(i) SEQUENCE CHARACTERISTICS:
        (A) LENGTH: 338 amino acids
        (B) TYPE: amino acid
        (D) TOPOLOGY: linear (ii) MOLECULE TYPE: protein (xi) SEQUENCE DESCRIPTION: SEQ ID NO:3:

```
Gln  Ile  Gly  Val  Cys  Tyr  Gly  Met  Leu  Gly  Asn  Asn  Leu  Pro  Ser  Ala
1                    5                     10                          15

Asn  Asp  Val  Ile  Gly  Leu  Tyr  Arg  Ser  Asn  Asn  Ile  Lys  Arg  Met  Arg
               20                     25                          30

Leu  Tyr  Asp  Pro  Asn  Gln  Ala  Ala  Leu  Glu  Ala  Leu  Arg  Asn  Ser  Gly
               35                     40                          45

Ile  Glu  Leu  Ile  Leu  Gly  Val  Pro  Asn  Ser  Asp  Leu  Gln  Gly  Leu  Ala
          50                     55                     60

Thr  Asn  Pro  Asp  Thr  Ser  Arg  Gln  Trp  Val  Gln  Lys  Asn  Val  Leu  Asn
65                      70                     75                          80

Phe  Trp  Pro  Ser  Val  Lys  Ile  Lys  Tyr  Val  Ala  Val  Gly  Asn  Glu  Val
               85                     90                          95

Ser  Pro  Val  Gly  Gly  Ser  Ser  Val  Ala  Gln  Tyr  Val  Leu  Pro  Ala
```

|       |       |       |       | 100   |       |       |       |       | 105   |       |       |       |       | 110   |       |
|-------|-------|-------|-------|-------|-------|-------|-------|-------|-------|-------|-------|-------|-------|-------|-------|
| Ile   | Gln   | Asn   | Val   | Tyr   | Gln   | Ala   | Ile   | Arg   | Ala   | Gln   | Gly   | Leu   | His   | Asp   | Gln   |
|       |       | 115   |       |       |       |       | 120   |       |       |       |       | 125   |       |       |       |
| Ile   | Lys   | Val   | Ser   | Thr   | Ser   | Ile   | Asp   | Met   | Thr   | Leu   | Ile   | Gly   | Asn   | Ser   | Phe   |
|       | 130   |       |       |       |       | 135   |       |       |       |       | 140   |       |       |       |       |
| Pro   | Pro   | Ser   | Gln   | Gly   | Ser   | Phe   | Arg   | Gly   | Asp   | Val   | Arg   | Ser   | Tyr   | Leu   | Asp   |
| 145   |       |       |       |       | 150   |       |       |       |       | 155   |       |       |       |       | 160   |
| Pro   | Ile   | Ile   | Gly   | Tyr   | Leu   | Val   | Tyr   | Ala   | Asn   | Ala   | Pro   | Leu   | Leu   | Val   | Asn   |
|       |       |       |       | 165   |       |       |       |       | 170   |       |       |       |       | 175   |       |
| Val   | Tyr   | Pro   | Tyr   | Phe   | Ser   | Tyr   | Thr   | Gly   | Asn   | Pro   | Arg   | Asp   | Ile   | Ser   | Leu   |
|       |       |       | 180   |       |       |       |       | 185   |       |       |       |       | 190   |       |       |
| Pro   | Tyr   | Ala   | Leu   | Phe   | Thr   | Ala   | Pro   | Asn   | Val   | Val   | Val   | Trp   | Asp   | Gly   | Gln   |
|       |       | 195   |       |       |       |       | 200   |       |       |       |       | 205   |       |       |       |
| Tyr   | Gly   | Tyr   | Gln   | Asn   | Leu   | Phe   | Asp   | Ala   | Met   | Leu   | Asp   | Ser   | Val   | His   | Ala   |
|       | 210   |       |       |       |       | 215   |       |       |       |       | 220   |       |       |       |       |
| Ala   | Ile   | Asp   | Asn   | Thr   | Lys   | Ile   | Gly   | Tyr   | Val   | Glu   | Val   | Val   | Val   | Ser   | Glu   |
| 225   |       |       |       |       | 230   |       |       |       |       | 235   |       |       |       |       | 240   |
| Ser   | Gly   | Trp   | Pro   | Ser   | Asp   | Gly   | Gly   | Phe   | Ala   | Ala   | Thr   | Tyr   | Asp   | Asn   | Ala   |
|       |       |       |       | 245   |       |       |       |       | 250   |       |       |       |       | 255   |       |
| Arg   | Val   | Tyr   | Leu   | Asp   | Asn   | Leu   | Val   | Arg   | Arg   | Ala   | Asn   | Arg   | Gly   | Ser   | Pro   |
|       |       |       | 260   |       |       |       |       | 265   |       |       |       |       | 270   |       |       |
| Arg   | Arg   | Pro   | Ser   | Lys   | Pro   | Thr   | Glu   | Thr   | Tyr   | Ile   | Phe   | Ala   | Met   | Phe   | Asp   |
|       |       | 275   |       |       |       |       | 280   |       |       |       |       | 285   |       |       |       |
| Glu   | Asn   | Gln   | Lys   | Asn   | Pro   | Glu   | Ile   | Glu   | Lys   | His   | Phe   | Gly   | Leu   | Phe   | Asn   |
|       | 290   |       |       |       |       | 295   |       |       |       |       | 300   |       |       |       |       |
| Pro   | Asn   | Lys   | Gln   | Lys   | Lys   | Tyr   | Pro   | Phe   | Gly   | Phe   | Gly   | Gly   | Lys   | Arg   | Leu   |
| 305   |       |       |       |       | 310   |       |       |       |       | 315   |       |       |       |       | 320   |
| Gly   | Lys   | Val   | Val   | Ile   | Asp   | Asp   | Phe   | Asn   | Ala   | Thr   | Thr   | Ser   | Ile   | Lys   | Ser   |
|       |       |       |       | 325   |       |       |       |       | 330   |       |       |       |       | 335   |       |
| Asp   | Val   |       |       |       |       |       |       |       |       |       |       |       |       |       |       |

( 2 ) INFORMATION FOR SEQ ID NO:4:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

| Met | Ala | Pro | Ser | Gly | Lys | Ser | Thr | Leu | Leu | Leu | Leu | Phe | Leu | Leu | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Cys | Leu | Pro | Ser | Trp | Asn | Ala | Gly | Ala |     |     |     |     |     |     |     |
|     |     |     | 20  |     |     |     |     | 25  |     |     |     |     |     |     |     |

( 2 ) INFORMATION FOR SEQ ID NO:5:

( i ) SEQUENCE CHARACTERISTICS:
        ( A ) LENGTH: 89 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Ser | Ser | Pro | Leu | Lys | Asn | Ala | Leu | Val | Thr | Ala | Met | Leu | Ala | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

```
Gly Ala Leu Ser Ser Pro Thr Lys Gln His Val Gly Ile Pro Val Asn
             20                  25                  30

Ala Ser Pro Glu Val Gly Pro Gly Lys Tyr Ser Phe Lys Gln Val Arg
             35                  40                  45

Asn Pro Asn Tyr Lys Phe Asn Gly Pro Leu Ser Val Lys Lys Thr Tyr
             50                  55                  60

Leu Lys Tyr Gly Val Pro Ile Pro Ala Trp Leu Glu Asp Ala Val Gln
 65                  70                  75                  80

Asn Ser Thr Ser Gly Leu Ala Glu Arg
                 85
```

(2) INFORMATION FOR SEQ ID NO:6:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:6:

```
Met Arg Arg Thr Ser Lys Leu Thr Thr Phe Ser Leu Leu Phe Ser Leu
 1               5                  10                  15

Val Leu Leu Ser Ala Ala Leu Ala
             20
```

(2) INFORMATION FOR SEQ ID NO:7:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:7:

```
Met Pro Ser Leu Phe Ala Arg Asn Gln Arg Phe Ser Leu Ala Thr Leu
 1               5                  10                  15

Leu Leu Leu Leu Glu Leu Leu Thr Gly Asn Leu Arg Met Ala Asp Ala
             20                  25                  30
```

(2) INFORMATION FOR SEQ ID NO:8:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
ATTGGTGTGT GTTATGGCAT GCTGGGCAAC AATCTACCGT CAGCAAACGA TGTTATAGGT      60
CTTTATAGAT CAAATAACAT AAAGAGAATG AGACTCTATG ATCCTAATCA AGCTGCTCTA     120
GAAGCACTTA GAAATTCTGG CATTGAACTC ATTCTTGGGG TGCCAAACTC TGACCTTCAA     180
GGCCTTGCCA CCAATCCTGA CACTTCTCGT CAATGGGTGC AAAAAAACGT GTTGAACTTT     240
TGGCCTAGTG TCAAAATCAA GTACGTGGCA GTTGGAAATG AAGTGAGTCC CGTTGGAGGC     300
TCTTCTTCGG TAGCCCAATA TGTTCTACCT GCCATCCAAA ATGTATACCA AGCAATAAGA     360
GCTCAAGGCC TTCATGATCA AATCAAGGTT TCAACATCTA TTGACATGAC CCTAATAGGA     420
AACTCTTTCC CTCCATCGCA AGGTTCCTTC AGGGGTGATG TGAGATCATA CCTAGATCCC     480
```

```
ATAATTGGGT  ACTTGGTATA  TGCAAATGCA  CCATTACTAG  TCAATGTGTA  CCCTTATTTT         540

AGTTACACTG  GTAACCCCCG  TGACATATCA  CTTCCCTATG  CTCTTTTCAC  AGCACCAAAT         600

GTTGTGGTAT  GGGATGGTCA  ATATGGGTAC  CAAAATTTGT  TTGATGCTAT  GTTGGATTCA         660

GTACATGCAG  CCATTGATAA  CACTAAGATT  GGTTATGTGG  AGGTTGTTGT  ATCCGAGAGT         720

GGGTGGCCAT  CAGATGGAGG  ATTTGCTGCC  ACTTATGACA  ACGCACGCGT  GTACTTAGAC         780

AATTTGGTTC  GTCGTGCTAA  TAGAGGAAGC  CCAAGAAGGC  CTTCGAAGCC  CACTGAGACT         840

TATATATTTG  CCATGTTCGA  TGAAAATCAA  AAAAATCCAG  AGATAGAGAA  ACATTTTGGG         900

CTCTTCAATC  CCAACAAACA  AAAAAA                                                927
```

(2) INFORMATION FOR SEQ ID NO:9:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
ATGCCTTCTC  TCTTCGCTAG  AAACCAGAGG  TTCTCATTGG  CTACTCTCCT  GCTTCTTCTG          60

GAACTATTGA  CAGGAAACCT  TCGCATGGCA  GATGCT                                     96
```

(2) INFORMATION FOR SEQ ID NO:10:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
TACCCATTTG  GGTTTGGAGG  AAAGAGGCTA  GGGAAAGTTG  TTATTGACGA  CTTCAATGCA          60

ACAACTTCCA  TTAAGAGTGA  TGTG                                                   84
```

(2) INFORMATION FOR SEQ ID NO:11:

(i) SEQUENCE CHARACTERISTICS:
        (A) LENGTH: 1483 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 114..1223

(ix) FEATURE:
        (A) NAME/KEY: mat_peptide
        (B) LOCATION: 213..1223

(ix) FEATURE:
        (A) NAME/KEY: sig_peptide
        (B) LOCATION: 114..212

(xi) SEQUENCE DESCRIPTION: SEQ ID NO:11:

```
AAGCTTGCAT  GCCTGCAGGT  CGACTCTAGA  GGATCCCCCT  GGCGATCATC  AAGCCTAATA          60
```

|  |  |  |  |  |  |  |  |  |  |  |  |  |  |  |  |
|---|---|---|---|---|---|---|---|---|---|---|---|---|---|---|---|
| GAGGGCTAAT | CCTTCACTTG | TTTGTTTTGT | GGTGTATTAT | TACATTTTGC | ACC | ATG<br>Met<br>-33 | | | | | | | | | 116 |
| CCT<br>Pro | TCT<br>Ser | CTC<br>Leu<br>-30 | TTC<br>Phe | GCT<br>Ala | AGA<br>Arg | AAC<br>Asn | CAG<br>Gln<br>-25 | AGG<br>Arg | TTC<br>Phe | TCA<br>Ser | TTG<br>Leu | GCT<br>Ala<br>-20 | ACT<br>Thr | CTC<br>Leu | CTG<br>Leu | 164 |
| CTT<br>Leu | CTT<br>Leu<br>-15 | CTG<br>Leu | GAA<br>Glu | CTA<br>Leu | TTG<br>Leu | ACA<br>Thr<br>-10 | GGA<br>Gly | AAC<br>Asn | CTT<br>Leu | CGC<br>Arg | ATG<br>Met<br>-5 | GCA<br>Ala | GAT<br>Asp | GCT<br>Ala | CAA<br>Gln | 212 |
| ATT<br>Ile<br>1 | GGT<br>Gly | GTG<br>Val | TGT<br>Cys | TAT<br>Tyr<br>5 | GGC<br>Gly | ATG<br>Met | CTG<br>Leu | GGC<br>Gly | AAC<br>Asn<br>10 | AAT<br>Asn | CTA<br>Leu | CCG<br>Pro | TCA<br>Ser | GCA<br>Ala<br>15 | AAC<br>Asn | 260 |
| GAT<br>Asp | GTT<br>Val | ATA<br>Ile | GGT<br>Gly<br>20 | CTT<br>Leu | TAT<br>Tyr | AGA<br>Arg | TCA<br>Ser | AAT<br>Asn<br>25 | AAC<br>Asn | ATA<br>Ile | AAG<br>Lys | AGA<br>Arg | ATG<br>Met<br>30 | AGA<br>Arg | CTC<br>Leu | 308 |
| TAT<br>Tyr | GAT<br>Asp | CCT<br>Pro<br>35 | AAT<br>Asn | CAA<br>Gln | GCT<br>Ala | GCT<br>Ala | CTA<br>Leu<br>40 | GAA<br>Glu | GCA<br>Ala | CTT<br>Leu | AGA<br>Arg | AAT<br>Asn<br>45 | TCT<br>Ser | GGC<br>Gly | ATT<br>Ile | 356 |
| GAA<br>Glu | CTC<br>Leu<br>50 | ATT<br>Ile | CTT<br>Leu | GGG<br>Gly | GTG<br>Val | CCA<br>Pro<br>55 | AAC<br>Asn | TCT<br>Ser | GAC<br>Asp | CTT<br>Leu | CAA<br>Gln<br>60 | GGC<br>Gly | CTT<br>Leu | GCC<br>Ala | ACC<br>Thr | 404 |
| AAT<br>Asn<br>65 | CCT<br>Pro | GAC<br>Asp | ACT<br>Thr | TCT<br>Ser | CGT<br>Arg<br>70 | CAA<br>Gln | TGG<br>Trp | GTG<br>Val | CAA<br>Gln | AAA<br>Lys<br>75 | AAC<br>Asn | GTG<br>Val | TTG<br>Leu | AAC<br>Asn | TTT<br>Phe<br>80 | 452 |
| TGG<br>Trp | CCT<br>Pro | AGT<br>Ser | GTC<br>Val | AAA<br>Lys<br>85 | ATC<br>Ile | AAG<br>Lys | TAC<br>Tyr | GTG<br>Val | GCA<br>Ala<br>90 | GTT<br>Val | GGA<br>Gly | AAT<br>Asn | GAA<br>Glu | GTG<br>Val<br>95 | AGT<br>Ser | 500 |
| CCC<br>Pro | GTT<br>Val | GGA<br>Gly | GGC<br>Gly<br>100 | TCT<br>Ser | TCT<br>Ser | TCG<br>Ser | GTA<br>Val | GCC<br>Ala<br>105 | CAA<br>Gln | TAT<br>Tyr | GTT<br>Val | CTA<br>Leu | CCT<br>Pro<br>110 | GCC<br>Ala | ATC<br>Ile | 548 |
| CAA<br>Gln | AAT<br>Asn | GTA<br>Val<br>115 | TAC<br>Tyr | CAA<br>Gln | GCA<br>Ala | ATA<br>Ile | AGA<br>Arg<br>120 | GCT<br>Ala | CAA<br>Gln | GGC<br>Gly | CTT<br>Leu | CAT<br>His<br>125 | GAT<br>Asp | CAA<br>Gln | ATC<br>Ile | 596 |
| AAG<br>Lys | GTT<br>Val<br>130 | TCA<br>Ser | ACA<br>Thr | TCT<br>Ser | ATT<br>Ile | GAC<br>Asp<br>135 | ATG<br>Met | ACC<br>Thr | CTA<br>Leu | ATA<br>Ile | GGA<br>Gly<br>140 | AAC<br>Asn | TCT<br>Ser | TTC<br>Phe | CCT<br>Pro | 644 |
| CCA<br>Pro<br>145 | TCG<br>Ser | CAA<br>Gln | GGT<br>Gly | TCC<br>Ser | TTC<br>Phe<br>150 | AGG<br>Arg | GGT<br>Gly | GAT<br>Asp | GTG<br>Val | AGA<br>Arg<br>155 | TCA<br>Ser | TAC<br>Tyr | CTA<br>Leu | GAT<br>Asp | CCC<br>Pro<br>160 | 692 |
| ATA<br>Ile | ATT<br>Ile | GGG<br>Gly | TAC<br>Tyr | TTG<br>Leu<br>165 | GTA<br>Val | TAT<br>Tyr | GCA<br>Ala | AAT<br>Asn | GCA<br>Ala<br>170 | CCA<br>Pro | TTA<br>Leu | CTA<br>Leu | GTC<br>Val | AAT<br>Asn<br>175 | GTG<br>Val | 740 |
| TAC<br>Tyr | CCT<br>Pro | TAT<br>Tyr<br>180 | TTT<br>Phe | AGT<br>Ser | TAC<br>Tyr | ACT<br>Thr | GGT<br>Gly<br>185 | AAC<br>Asn | CCC<br>Pro | CGT<br>Arg | GAC<br>Asp | ATA<br>Ile<br>190 | TCA<br>Ser | CTT<br>Leu | CCC<br>Pro | 788 |
| TAT<br>Tyr | GCT<br>Ala | CTT<br>Leu<br>195 | TTC<br>Phe | ACA<br>Thr | GCA<br>Ala | CCA<br>Pro | AAT<br>Asn<br>200 | GTT<br>Val | GTG<br>Val | GTA<br>Val | TGG<br>Trp | GAT<br>Asp<br>205 | GGT<br>Gly | CAA<br>Gln | TAT<br>Tyr | 836 |
| GGG<br>Gly | TAC<br>Tyr | CAA<br>Gln<br>210 | AAT<br>Asn | TTG<br>Leu | TTT<br>Phe | GAT<br>Asp | GCT<br>Ala<br>215 | ATG<br>Met | TTG<br>Leu | GAT<br>Asp | TCA<br>Ser | GTA<br>Val<br>220 | CAT<br>His | GCA<br>Ala | GCC<br>Ala | 884 |
| ATT<br>Ile<br>225 | GAT<br>Asp | AAC<br>Asn | ACT<br>Thr | AAG<br>Lys | ATT<br>Ile<br>230 | GGT<br>Gly | TAT<br>Tyr | GTG<br>Val | GAG<br>Glu | GTT<br>Val<br>235 | GTT<br>Val | GTA<br>Val | TCC<br>Ser | GAG<br>Glu | AGT<br>Ser<br>240 | 932 |
| GGG<br>Gly | TGG<br>Trp | CCA<br>Pro | TCA<br>Ser<br>245 | GAT<br>Asp | GGA<br>Gly | GGA<br>Gly | TTT<br>Phe | GCT<br>Ala<br>250 | GCC<br>Ala | ACT<br>Thr | TAT<br>Tyr | GAC<br>Asp | AAC<br>Asn<br>255 | GCA<br>Ala | CGC<br>Arg | 980 |
| GTG<br>Val | TAC<br>Tyr | TTA<br>Leu | GAC<br>Asp | AAT<br>Asn | TTG<br>Leu | GTT<br>Val | CGT<br>Arg | CGT<br>Arg | GCT<br>Ala | AAT<br>Asn | AGA<br>Arg | GGA<br>Gly | AGC<br>Ser | CCA<br>Pro | AGA<br>Arg | 1028 |

|  |  |  |  |  |  |  |  |  |  |  |  |  |  |  |  |
|--|--|--|--|--|--|--|--|--|--|--|--|--|--|--|--|
|  |  |  | 260 |  |  |  | 265 |  |  |  | 270 |  |  |  |  |
| AGG | CCT | TCG | AAG | CCC | ACT | GAG | ACT | TAT | ATA | TTT | GCC | ATG | TTC | GAT | GAA | 1076 |
| Arg | Pro | Ser | Lys | Pro | Thr | Glu | Thr | Tyr | Ile | Phe | Ala | Met | Phe | Asp | Glu |  |
|  |  | 275 |  |  |  | 280 |  |  |  |  | 285 |  |  |  |  |
| AAT | CAA | AAA | AAT | CCA | GAG | ATA | GAG | AAA | CAT | TTT | GGG | CTC | TTC | AAT | CCC | 1124 |
| Asn | Gln | Lys | Asn | Pro | Glu | Ile | Glu | Lys | His | Phe | Gly | Leu | Phe | Asn | Pro |  |
|  | 290 |  |  |  |  | 295 |  |  |  |  | 300 |  |  |  |  |
| AAC | AAA | CAA | AAA | AAA | TAC | CCA | TTT | GGG | TTT | GGA | GGA | AAG | AGG | CTA | GGG | 1172 |
| Asn | Lys | Gln | Lys | Lys | Tyr | Pro | Phe | Gly | Phe | Gly | Gly | Lys | Arg | Leu | Gly |  |
| 305 |  |  |  |  | 310 |  |  |  |  | 315 |  |  |  |  | 320 |  |
| AAA | GTT | GTT | ATT | GAC | GAC | TTC | AAT | GCA | ACA | ACT | TCC | ATT | AAG | AGT | GAT | 1220 |
| Lys | Val | Val | Ile | Asp | Asp | Phe | Asn | Ala | Thr | Thr | Ser | Ile | Lys | Ser | Asp |  |
|  |  |  |  | 325 |  |  |  |  | 330 |  |  |  |  | 335 |  |  |

```
GTG                                                                      1273
Val

TAAGGTTGGA ATCCTACTCC TCAAATCTC  TGTTATTCCA CCCATAAAAT
AAGAGAGAAT ATGTTGTTTG TGTGAAATAT GTATATATCC TTCAGTCTTG GATGAATAAA        1333
ATTTGTGAAA ATTTTATTTT TTTTTTTTT  GGACTAGAAA TAGCCTGATA CTTAATTATT        1393
ATCTTTTTAT ACCACACGTT GGTTTCCTTC ATGAGTACAA ACCGAAATAA AACCAACAAT        1453
TAATCTTGTT TTATTACAAC ACACAAGCTT                                         1483
```

( 2 ) INFORMATION FOR SEQ ID NO:12:

( i ) SEQUENCE CHARACTERISTICS:
        ( A ) LENGTH: 370 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Met | Pro | Ser | Leu | Phe | Ala | Arg | Asn | Gln | Arg | Phe | Ser | Leu | Ala | Thr | Leu |
|-----|-----|-----|-----|-----|-----|-----|-----|-----|-----|-----|-----|-----|-----|-----|-----|
| -33 |     |     | -30 |     |     |     | -25 |     |     |     | -20 |     |     |     |     |
| Leu | Leu | Leu | Leu | Glu | Leu | Leu | Thr | Gly | Asn | Leu | Arg | Met | Ala | Asp | Ala |
|     |     | -15 |     |     |     | -10 |     |     |     |     | -5  |     |     |     |     |
| Gln | Ile | Gly | Val | Cys | Tyr | Gly | Met | Leu | Gly | Asn | Asn | Leu | Pro | Ser | Ala |
|     | 1   |     |     |     | 5   |     |     |     |     | 10  |     |     |     |     | 15  |
| Asn | Asp | Val | Ile | Gly | Leu | Tyr | Arg | Ser | Asn | Asn | Ile | Lys | Arg | Met | Arg |
|     |     |     |     | 20  |     |     |     |     | 25  |     |     |     |     | 30  |     |
| Leu | Tyr | Asp | Pro | Asn | Gln | Ala | Ala | Leu | Glu | Ala | Leu | Arg | Asn | Ser | Gly |
|     |     |     | 35  |     |     |     |     | 40  |     |     |     |     | 45  |     |     |
| Ile | Glu | Leu | Ile | Leu | Gly | Val | Pro | Asn | Ser | Asp | Leu | Gln | Gly | Leu | Ala |
|     |     | 50  |     |     |     |     | 55  |     |     |     |     | 60  |     |     |     |
| Thr | Asn | Pro | Asp | Thr | Ser | Arg | Gln | Trp | Val | Gln | Lys | Asn | Val | Leu | Asn |
|     | 65  |     |     |     |     | 70  |     |     |     |     | 75  |     |     |     |     |
| Phe | Trp | Pro | Ser | Val | Lys | Ile | Lys | Tyr | Val | Ala | Val | Gly | Asn | Glu | Val |
| 80  |     |     |     |     | 85  |     |     |     |     | 90  |     |     |     |     | 95  |
| Ser | Pro | Val | Gly | Gly | Ser | Ser | Ser | Val | Ala | Gln | Tyr | Val | Leu | Pro | Ala |
|     |     |     |     | 100 |     |     |     |     | 105 |     |     |     |     | 110 |     |
| Ile | Gln | Asn | Val | Tyr | Gln | Ala | Ile | Arg | Ala | Gln | Gly | Leu | His | Asp | Gln |
|     |     |     | 115 |     |     |     |     | 120 |     |     |     |     | 125 |     |     |
| Ile | Lys | Val | Ser | Thr | Ser | Ile | Asp | Met | Thr | Leu | Ile | Gly | Asn | Ser | Phe |
|     |     |     | 130 |     |     |     |     | 135 |     |     |     |     | 140 |     |     |
| Pro | Pro | Ser | Gln | Gly | Ser | Phe | Arg | Gly | Asp | Val | Arg | Ser | Tyr | Leu | Asp |
|     |     |     | 145 |     |     |     |     | 150 |     |     |     |     | 155 |     |     |
| Pro | Ile | Ile | Gly | Tyr | Leu | Val | Tyr | Ala | Asn | Ala | Pro | Leu | Leu | Val | Asn |
| 160 |     |     |     |     | 165 |     |     |     |     | 170 |     |     |     |     | 175 |

| | | | | | | | | | | | | | | |
|---|---|---|---|---|---|---|---|---|---|---|---|---|---|---|
|Val|Tyr|Pro|Tyr|Phe|Ser|Tyr|Thr|Gly|Asn|Pro|Arg|Asp|Ile|Ser|Leu|
| | | | |180| | | |185| | | | |190| |
|Pro|Tyr|Ala|Leu|Phe|Thr|Ala|Pro|Asn|Val|Val|Trp|Asp|Gly|Gln|
| | | |195| | | |200| | | |205| | | |
|Tyr|Gly|Tyr|Gln|Asn|Leu|Phe|Asp|Ala|Met|Leu|Asp|Ser|Val|His|Ala|
| | |210| | | |215| | | |220| | | | |
|Ala|Ile|Asp|Asn|Thr|Lys|Ile|Gly|Tyr|Val|Glu|Val|Val|Ser|Glu|
| |225| | | |230| | | | |235| | | | |
|Ser|Gly|Trp|Pro|Ser|Asp|Gly|Gly|Phe|Ala|Ala|Thr|Tyr|Asp|Asn|Ala|
|240| | | |245| | | |250| | | | |255| |
|Arg|Val|Tyr|Leu|Asp|Asn|Leu|Val|Arg|Arg|Ala|Asn|Arg|Gly|Ser|Pro|
| | | |260| | | |265| | | |270| | | |
|Arg|Arg|Pro|Ser|Lys|Pro|Thr|Glu|Thr|Tyr|Ile|Phe|Ala|Met|Phe|Asp|
| | |275| | | |280| | | |285| | | | |
|Glu|Asn|Gln|Lys|Asn|Pro|Glu|Ile|Glu|Lys|His|Phe|Gly|Leu|Phe|Asn|
| |290| | | |295| | | |300| | | | | |
|Pro|Asn|Lys|Gln|Lys|Lys|Tyr|Pro|Phe|Gly|Phe|Gly|Lys|Arg|Leu|
| |305| | |310| | | |315| | | | | | |
|Gly|Lys|Val|Val|Ile|Asp|Asp|Phe|Asn|Ala|Thr|Thr|Ser|Ile|Lys|Ser|
|320| | | |325| | | |330| | | | |335| |
|Asp|Val| | | | | | | | | | | | | |

( 2 ) INFORMATION FOR SEQ ID NO:13:

( i ) SEQUENCE CHARACTERISTICS:
        ( A ) LENGTH: 1483 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 114..1223

( i x ) FEATURE:
        ( A ) NAME/KEY: sig_peptide
        ( B ) LOCATION: 114..212

( i x ) FEATURE:
        ( A ) NAME/KEY: mat_peptide
        ( B ) LOCATION: 213..1223

( x i ) SEQUENCE DESCRIPTION: SEQ ID NO:13:

```
AAGCTTGCAT GCCTGCAGGT CGACTCTAGA GGATCCCCCT GGCGATCATC AAGCCTAATA        60

GAGGGCTAAT CCTTCACTTG TTTGTTTTGT GGTGTATTCA TATGTTTGGA TCC ATG          116
                                                             Met
                                                             -33

CCT TCT CTC TTC GCT AGA AAC CAG AGG TTC TCA TTG GCT ACT CTC CTG          164
Pro Ser Leu Phe Ala Arg Asn Gln Arg Phe Ser Leu Ala Thr Leu Leu
    -30             -25                 -20

CTT CTT CTG GAA CTA TTG ACA GGA AAC CTT CGC ATG GCA GAT GCT CAA          212
Leu Leu Leu Glu Leu Leu Thr Gly Asn Leu Arg Met Ala Asp Ala Gln
    -15             -10                  -5

ATT GGT GTG TGT TAT GGC ATG CTG GGC AAC AAT CTA CCG TCA GCA AAC          260
Ile Gly Val Cys Tyr Gly Met Leu Gly Asn Asn Leu Pro Ser Ala Asn
  1               5                  10                  15

GAT GTT ATA GGT CTT TAT AGA TCA AAT AAC ATA AAG AGA ATG AGA CTC          308
```

|     |     |     |     |     |     |     |     |     |     |     |     |     |     |     |      |
|-----|-----|-----|-----|-----|-----|-----|-----|-----|-----|-----|-----|-----|-----|-----|------|
| Asp | Val | Ile | Gly | Leu | Tyr | Arg | Ser | Asn | Ile | Lys | Arg | Met | Arg | Leu |      |
|     |     |     | 20  |     |     |     |     | 25  |     |     |     | 30  |     |     |      |
| TAT | GAT | CCT | AAT | CAA | GCT | GCT | CTA | GAA | GCA | CTT | AGA | AAT | TCT | GGC | ATT  | 356 |
| Tyr | Asp | Pro | Asn | Gln | Ala | Ala | Leu | Glu | Ala | Leu | Arg | Asn | Ser | Gly | Ile  |
|     |     | 35  |     |     |     | 40  |     |     |     |     | 45  |     |     |     |      |
| GAA | CTC | ATT | CTT | GGG | GTG | CCA | AAC | TCT | GAC | CTT | CAA | GGC | CTT | GCC | ACC  | 404 |
| Glu | Leu | Ile | Leu | Gly | Val | Pro | Asn | Ser | Asp | Leu | Gln | Gly | Leu | Ala | Thr  |
|     | 50  |     |     |     | 55  |     |     |     |     | 60  |     |     |     |     |      |
| AAT | CCT | GAC | ACT | TCT | CGT | CAA | TGG | GTG | CAA | AAA | AAC | GTG | TTG | AAC | TTT  | 452 |
| Asn | Pro | Asp | Thr | Ser | Arg | Gln | Trp | Val | Gln | Lys | Asn | Val | Leu | Asn | Phe  |
| 65  |     |     |     | 70  |     |     |     |     | 75  |     |     |     |     | 80  |      |
| TGG | CCT | AGT | GTC | AAA | ATC | AAG | TAC | GTG | GCA | GTT | GGA | AAT | GAA | GTG | AGT  | 500 |
| Trp | Pro | Ser | Val | Lys | Ile | Lys | Tyr | Val | Ala | Val | Gly | Asn | Glu | Val | Ser  |
|     |     |     |     | 85  |     |     |     |     | 90  |     |     |     |     | 95  |      |
| CCC | GTT | GGA | GGC | TCT | TCT | TCG | GTA | GCC | CAA | TAT | GTT | CTA | CCT | GCC | ATC  | 548 |
| Pro | Val | Gly | Gly | Ser | Ser | Ser | Val | Ala | Gln | Tyr | Val | Leu | Pro | Ala | Ile  |
|     |     |     | 100 |     |     |     |     | 105 |     |     |     |     | 110 |     |      |
| CAA | AAT | GTA | TAC | CAA | GCA | ATA | AGA | GCA | CAA | GGC | CTT | CAT | GAT | CAA | ATC  | 596 |
| Gln | Asn | Val | Tyr | Gln | Ala | Ile | Arg | Ala | Gln | Gly | Leu | His | Asp | Gln | Ile  |
|     |     | 115 |     |     |     |     | 120 |     |     |     |     | 125 |     |     |      |
| AAG | GTT | TCA | ACA | TCT | ATT | GAC | ATG | ACC | CTA | ATA | GGA | AAC | TCT | TTC | CCT  | 644 |
| Lys | Val | Ser | Thr | Ser | Ile | Asp | Met | Thr | Leu | Ile | Gly | Asn | Ser | Phe | Pro  |
|     | 130 |     |     |     |     | 135 |     |     |     |     | 140 |     |     |     |      |
| CCA | TCG | CAA | GGT | TCC | TTC | AGG | GGT | GAT | GTG | AGA | TCA | TAC | CTA | GAT | CCC  | 692 |
| Pro | Ser | Gln | Gly | Ser | Phe | Arg | Gly | Asp | Val | Arg | Ser | Tyr | Leu | Asp | Pro  |
| 145 |     |     |     | 150 |     |     |     |     | 155 |     |     |     |     | 160 |      |
| ATA | ATT | GGG | TAC | TTG | GTA | TAT | GCA | AAT | GCA | CCA | TTA | CTA | GTC | AAT | GTG  | 740 |
| Ile | Ile | Gly | Tyr | Leu | Val | Tyr | Ala | Asn | Ala | Pro | Leu | Leu | Val | Asn | Val  |
|     |     |     |     | 165 |     |     |     |     | 170 |     |     |     |     | 175 |      |
| TAC | CCT | TAT | TTT | AGT | TAC | ACT | GGT | AAC | CCC | CGT | GAC | ATA | TCA | CTT | CCC  | 788 |
| Tyr | Pro | Tyr | Phe | Ser | Tyr | Thr | Gly | Asn | Pro | Arg | Asp | Ile | Ser | Leu | Pro  |
|     |     |     | 180 |     |     |     |     | 185 |     |     |     |     | 190 |     |      |
| TAT | GCT | CTT | TTC | ACA | GCA | CCA | AAT | GTT | GTG | GTA | TGG | GAT | GGT | CAA | TAT  | 836 |
| Tyr | Ala | Leu | Phe | Thr | Ala | Pro | Asn | Val | Val | Val | Trp | Asp | Gly | Gln | Tyr  |
|     |     | 195 |     |     |     |     | 200 |     |     |     |     | 205 |     |     |      |
| GGG | TAC | CAA | AAT | TTG | TTT | GAT | GCT | ATG | TTG | GAT | TCA | GTA | CAT | GCA | GCC  | 884 |
| Gly | Tyr | Gln | Asn | Leu | Phe | Asp | Ala | Met | Leu | Asp | Ser | Val | His | Ala | Ala  |
|     | 210 |     |     |     |     | 215 |     |     |     |     | 220 |     |     |     |      |
| ATT | GAT | AAC | ACT | AAG | ATT | GGT | TAT | GTG | GAG | GTT | GTT | GTA | TCC | GAG | AGT  | 932 |
| Ile | Asp | Asn | Thr | Lys | Ile | Gly | Tyr | Val | Glu | Val | Val | Val | Ser | Glu | Ser  |
| 225 |     |     |     |     | 230 |     |     |     |     | 235 |     |     |     |     | 240  |
| GGG | TGG | CCA | TCA | GAT | GGA | GGA | TTT | GCT | GCC | ACT | TAT | GAC | AAC | GCA | CGC  | 980 |
| Gly | Trp | Pro | Ser | Asp | Gly | Gly | Phe | Ala | Ala | Thr | Tyr | Asp | Asn | Ala | Arg  |
|     |     |     |     | 245 |     |     |     |     | 250 |     |     |     |     | 255 |      |
| GTG | TAC | TTA | GAC | AAT | TTG | GTT | CGT | CGT | GCT | AAT | AGA | GGA | AGC | CCA | AGA  | 1028 |
| Val | Tyr | Leu | Asp | Asn | Leu | Val | Arg | Arg | Ala | Asn | Arg | Gly | Ser | Pro | Arg  |
|     |     |     | 260 |     |     |     |     | 265 |     |     |     |     | 270 |     |      |
| AGG | CCT | TCG | AAG | CCC | ACT | GAG | ACT | TAT | ATA | TTT | GCC | ATG | TTC | GAT | GAA  | 1076 |
| Arg | Pro | Ser | Lys | Pro | Thr | Glu | Thr | Tyr | Ile | Phe | Ala | Met | Phe | Asp | Glu  |
|     |     | 275 |     |     |     | 280 |     |     |     |     | 285 |     |     |     |      |
| AAT | CAA | AAA | AAT | CCA | GAG | ATA | GAG | AAA | CAT | TTT | GGG | CTC | TTC | AAT | CCC  | 1124 |
| Asn | Gln | Lys | Asn | Pro | Glu | Ile | Glu | Lys | His | Phe | Gly | Leu | Phe | Asn | Pro  |
|     | 290 |     |     |     |     | 295 |     |     |     |     | 300 |     |     |     |      |
| AAC | AAA | CAA | AAA | AAA | TAC | CCA | TTT | GGG | TTT | GGA | GGA | AAG | AGG | CTA | GGG  | 1172 |
| Asn | Lys | Gln | Lys | Lys | Tyr | Pro | Phe | Gly | Phe | Gly | Gly | Lys | Arg | Leu | Gly  |
| 305 |     |     |     |     | 310 |     |     |     |     | 315 |     |     |     |     | 320  |
| AAA | GTT | GTT | ATT | GAC | GAC | TTC | AAT | GCA | ACA | ACT | TCC | ATT | AAG | AGT | GAT  | 1220 |
| Lys | Val | Val | Ile | Asp | Asp | Phe | Asn | Ala | Thr | Thr | Ser | Ile | Lys | Ser | Asp  |
|     |     |     |     | 325 |     |     |     |     | 330 |     |     |     |     | 335 |      |

```
GTG  TAAGGTTGAG  CTCCTAAGCT  TCAAAATCTC  TGTTATTCCA  CCCATAAAAT           1273
Val

AAGAGAGAAT  ATGTTGTTTG  TGTGAAATAT  GTATATATCC  TTCAGTCTTG  GATGAATAAA    1333

ATTTGTGAAA  ATTTTATTTT  TTTTTTTTTT  GGACTAGAAA  TAGCCTGATA  CTTAATTATT    1393

ATCTTTTTAT  ACCACACGTT  GGTTTCCTTC  ATGAGTACAA  ACCGAAATAA  AACCAACAAT    1453

TAATCTTGTT  TTATTACAAC  ACACAAGCTT                                        1483
```

( 2 ) INFORMATION FOR SEQ ID NO:14:

( i ) SEQUENCE CHARACTERISTICS:
        ( A ) LENGTH: 370 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met  Pro  Ser  Leu  Phe  Ala  Arg  Asn  Gln  Arg  Phe  Ser  Leu  Ala  Thr  Leu
-33            -30                      -25                      -20

Leu  Leu  Leu  Leu  Glu  Leu  Leu  Thr  Gly  Asn  Leu  Arg  Met  Ala  Asp  Ala
          -15                      -10                      -5

Gln  Ile  Gly  Val  Cys  Tyr  Gly  Met  Leu  Gly  Asn  Asn  Leu  Pro  Ser  Ala
     1              5                        10                           15

Asn  Asp  Val  Ile  Gly  Leu  Tyr  Arg  Ser  Asn  Ile  Lys  Arg  Met  Arg
                    20                   25                        30

Leu  Tyr  Asp  Pro  Asn  Gln  Ala  Ala  Leu  Glu  Ala  Leu  Arg  Asn  Ser  Gly
               35                   40                        45

Ile  Glu  Leu  Ile  Leu  Gly  Val  Pro  Asn  Ser  Asp  Leu  Gln  Gly  Leu  Ala
          50                   55                        60

Thr  Asn  Pro  Asp  Thr  Ser  Arg  Gln  Trp  Val  Gln  Lys  Asn  Val  Leu  Asn
     65                   70                        75

Phe  Trp  Pro  Ser  Val  Lys  Ile  Lys  Tyr  Val  Ala  Val  Gly  Asn  Glu  Val
80                        85                        90                   95

Ser  Pro  Val  Gly  Gly  Ser  Ser  Val  Ala  Gln  Tyr  Val  Leu  Pro  Ala
                    100                  105                       110

Ile  Gln  Asn  Val  Tyr  Gln  Ala  Ile  Arg  Ala  Gln  Gly  Leu  His  Asp  Gln
               115                  120                       125

Ile  Lys  Val  Ser  Thr  Ser  Ile  Asp  Met  Thr  Leu  Ile  Gly  Asn  Ser  Phe
          130                  135                       140

Pro  Pro  Ser  Gln  Gly  Ser  Phe  Arg  Gly  Asp  Val  Arg  Ser  Tyr  Leu  Asp
     145                  150                       155

Pro  Ile  Ile  Gly  Tyr  Leu  Val  Tyr  Ala  Asn  Ala  Pro  Leu  Leu  Val  Asn
160                  165                       170                       175

Val  Tyr  Pro  Tyr  Phe  Ser  Tyr  Thr  Gly  Asn  Pro  Arg  Asp  Ile  Ser  Leu
               180                  185                       190

Pro  Tyr  Ala  Leu  Phe  Thr  Ala  Pro  Asn  Val  Val  Trp  Asp  Gly  Gln
          195                  200                       205

Tyr  Gly  Tyr  Gln  Asn  Leu  Phe  Asp  Ala  Met  Leu  Asp  Ser  Val  His  Ala
          210                  215                       220

Ala  Ile  Asp  Asn  Thr  Lys  Ile  Gly  Tyr  Val  Glu  Val  Val  Ser  Glu
     225                  230                       235

Ser  Gly  Trp  Pro  Ser  Asp  Gly  Gly  Phe  Ala  Ala  Thr  Tyr  Asp  Asn  Ala
240                  245                       250                       255

Arg  Val  Tyr  Leu  Asp  Asn  Leu  Val  Arg  Arg  Ala  Asn  Arg  Gly  Ser  Pro
               260                  265                       270
```

```
Arg  Arg  Pro  Ser  Lys  Pro  Thr  Glu  Thr  Tyr  Ile  Phe  Ala  Met  Phe  Asp
              275                 280                           285

Glu  Asn  Gln  Lys  Asn  Pro  Glu  Ile  Glu  Lys  His  Phe  Gly  Leu  Phe  Asn
              290                 295                           300

Pro  Asn  Lys  Gln  Lys  Lys  Tyr  Pro  Phe  Gly  Phe  Gly  Gly  Lys  Arg  Leu
              305                 310                           315

Gly  Lys  Val  Val  Ile  Asp  Asp  Phe  Asn  Ala  Thr  Thr  Ser  Ile  Lys  Ser
320                      325                      330                      335

Asp  Val
```

(2) INFORMATION FOR SEQ ID NO:15:

(i) SEQUENCE CHARACTERISTICS:
        (A) LENGTH: 1038 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 4..1017

(xi) SEQUENCE DESCRIPTION: SEQ ID NO:15:

```
CAT  ATG  ATT  GGT  GTG  TGT  TAT  GGC  ATG  CTG  GGC  AAC  AAT  CTA  CCG  TCA    48
     Met  Ile  Gly  Val  Cys  Tyr  Gly  Met  Leu  Gly  Asn  Asn  Leu  Pro  Ser
     1              5                        10                       15

GCA  AAC  GAT  GTT  ATA  GGT  CTT  TAT  AGA  TCA  AAT  AAC  ATA  AAG  AGA  ATG    96
Ala  Asn  Asp  Val  Ile  Gly  Leu  Tyr  Arg  Ser  Asn  Asn  Ile  Lys  Arg  Met
               20                   25                        30

AGA  CTC  TAT  GAT  CCT  AAT  CAA  GCT  GCT  CTA  GAA  GCA  CTT  AGA  AAT  TCT   144
Arg  Leu  Tyr  Asp  Pro  Asn  Gln  Ala  Ala  Leu  Glu  Ala  Leu  Arg  Asn  Ser
               35                   40                        45

GGC  ATT  GAA  CTC  ATT  CTT  GGG  GTG  CCA  AAC  TCT  GAC  CTT  CAA  GGC  CTT   192
Gly  Ile  Glu  Leu  Ile  Leu  Gly  Val  Pro  Asn  Ser  Asp  Leu  Gln  Gly  Leu
          50                        55                        60

GCC  ACC  AAT  CCT  GAC  ACT  TCT  CGT  CAA  TGG  GTG  CAA  AAA  AAC  GTG  TTG   240
Ala  Thr  Asn  Pro  Asp  Thr  Ser  Arg  Gln  Trp  Val  Gln  Lys  Asn  Val  Leu
     65                       70                        75

AAC  TTT  TGG  CCT  AGT  GTC  AAA  ATC  AAG  TAC  GTG  GCA  GTT  GGA  AAT  GAA   288
Asn  Phe  Trp  Pro  Ser  Val  Lys  Ile  Lys  Tyr  Val  Ala  Val  Gly  Asn  Glu
80                       85                        90                       95

GTG  AGT  CCC  GTT  GGA  GGC  TCT  TCT  TCG  GTA  GCC  CAA  TAT  GTT  CTA  CCT   336
Val  Ser  Pro  Val  Gly  Gly  Ser  Ser  Ser  Val  Ala  Gln  Tyr  Val  Leu  Pro
                    100                      105                      110

GCC  ATC  CAA  AAT  GTA  TAC  CAA  GCA  ATA  AGA  GCA  CAA  GGC  CTT  CAT  GAT   384
Ala  Ile  Gln  Asn  Val  Tyr  Gln  Ala  Ile  Arg  Ala  Gln  Gly  Leu  His  Asp
               115                      120                      125

CAA  ATC  AAG  GTT  TCA  ACA  TCT  ATT  GAC  ATG  ACC  CTA  ATA  GGA  AAC  TCT   432
Gln  Ile  Lys  Val  Ser  Thr  Ser  Ile  Asp  Met  Thr  Leu  Ile  Gly  Asn  Ser
          130                      135                      140

TTC  CCT  CCA  TCG  CAA  GGT  TCC  TTC  AGG  GGT  GAT  GTG  AGA  TCA  TAC  CTA   480
Phe  Pro  Pro  Ser  Gln  Gly  Ser  Phe  Arg  Gly  Asp  Val  Arg  Ser  Tyr  Leu
     145                      150                      155

GAT  CCC  ATA  ATT  GGG  TAC  TTG  GTA  TAT  GCA  AAT  GCA  CCA  TTA  CTA  GTC   528
Asp  Pro  Ile  Ile  Gly  Tyr  Leu  Val  Tyr  Ala  Asn  Ala  Pro  Leu  Leu  Val
160                      165                      170                      175

AAT  GTG  TAC  CCT  TAT  TTT  AGT  TAC  ACT  GGT  AAC  CCC  CGT  GAC  ATA  TCA   576
```

| | | | | | | | | | | | | | | |
|---|---|---|---|---|---|---|---|---|---|---|---|---|---|---|
| Asn | Val | Tyr | Pro | Tyr 180 | Phe | Ser | Tyr | Thr | Gly 185 | Asn | Pro | Arg | Asp | Ile Ser 190 |

| | | | | | | | | | | | | | | | |
|---|---|---|---|---|---|---|---|---|---|---|---|---|---|---|---|
| CTT | CCC | TAT | GCT | CTT | TTC | ACA | GCA | CCA | AAT | GTT | GTG | GTA | TGG | GAT GGT | 624 |
| Leu | Pro | Tyr | Ala 195 | Leu | Phe | Thr | Ala | Pro 200 | Asn | Val | Val | Val | Trp 205 | Asp Gly | |
| CAA | TAT | GGG | TAC | CAA | AAT | TTG | TTT | GAT | GCT | ATG | TTG | GAT | TCA | GTA CAT | 672 |
| Gln | Tyr | Gly 210 | Tyr | Gln | Asn | Leu | Phe 215 | Asp | Ala | Met | Leu | Asp 220 | Ser | Val His | |
| GCA | GCC | ATT | GAT | AAC | ACT | AAG | ATT | GGT | TAT | GTG | GAG | GTT | GTT | GTA TCC | 720 |
| Ala | Ala 225 | Ile | Asp | Asn | Thr | Lys 230 | Ile | Gly | Tyr | Val | Glu 235 | Val | Val | Val Ser | |
| GAG | AGT | GGG | TGG | CCA | TCA | GAT | GGA | GGA | TTT | GCT | GCC | ACT | TAT | GAC AAC | 768 |
| Glu 240 | Ser | Gly | Trp | Pro 245 | Ser | Asp | Gly | Gly 250 | Phe | Ala | Ala | Thr 255 | Tyr | Asp Asn | |
| GCA | CGC | GTG | TAC | TTA | GAC | AAT | TTG | GTT | CGT | CGT | GCT | AAT | AGA | GGA AGC | 816 |
| Ala | Arg | Val | Tyr | Leu 260 | Asp | Asn | Leu | Val 265 | Arg | Arg | Ala | Asn 270 | Arg | Gly Ser | |
| CCA | AGA | AGG | CCT | TCG | AAG | CCC | ACT | GAG | ACT | TAT | ATA | TTT | GCC | ATG TTC | 864 |
| Pro | Arg | Arg | Pro 275 | Ser | Lys | Pro | Thr 280 | Glu | Thr | Tyr | Ile 285 | Phe | Ala | Met Phe | |
| GAT | GAA | AAT | CAA | AAA | AAT | CCA | GAG | ATA | GAG | AAA | CAT | TTT | GGG | CTC TTC | 912 |
| Asp | Glu | Asn 290 | Gln | Lys | Asn | Pro 295 | Glu | Ile | Glu | Lys 300 | His | Phe | Gly | Leu Phe | |
| AAT | CCC | AAC | AAA | CAA | AAA | AAA | TAC | CCA | TTT | GGG | TTT | GGA | GGA | AAG AGG | 960 |
| Asn | Pro 305 | Asn | Lys | Gln | Lys 310 | Lys | Tyr | Pro | Phe 315 | Gly | Phe | Gly | Gly | Lys Arg | |
| CTA | GGG | AAA | GTT | GTT | ATT | GAC | GAC | TTC | AAT | GCA | ACA | ACT | TCC | ATT AAG | 1008 |
| Leu 320 | Gly | Lys | Val | Val 325 | Ile | Asp | Asp | Phe | Asn 330 | Ala | Thr | Thr | Ser 335 | Ile Lys | |
| AGT | GAT | GTG | TAAGGTTGAG | CTCCTAAGCT | T | | | | | | | | | | 1038 |
| Ser | Asp | Val | | | | | | | | | | | | | |

( 2 ) INFORMATION FOR SEQ ID NO:16:

( i ) SEQUENCE CHARACTERISTICS:
        ( A ) LENGTH: 338 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| | | | | | | | | | | | | | | |
|---|---|---|---|---|---|---|---|---|---|---|---|---|---|---|
| Met 1 | Ile | Gly | Val | Cys 5 | Tyr | Gly | Met | Leu | Gly 10 | Asn | Asn | Leu | Pro | Ser Ala 15 |
| Asn | Asp | Val | Ile 20 | Gly | Leu | Tyr | Arg | Ser 25 | Asn | Asn | Ile | Lys | Arg 30 | Met Arg |
| Leu | Tyr | Asp 35 | Pro | Asn | Gln | Ala | Ala 40 | Leu | Glu | Ala | Leu | Arg 45 | Asn | Ser Gly |
| Ile | Glu 50 | Leu | Ile | Leu | Gly | Val 55 | Pro | Asn | Ser | Asp | Leu 60 | Gln | Gly | Leu Ala |
| Thr 65 | Asn | Pro | Asp | Thr | Ser 70 | Arg | Gln | Trp | Val | Gln 75 | Lys | Asn | Val | Leu Asn 80 |
| Phe | Trp | Pro | Ser | Val 85 | Lys | Ile | Lys | Tyr | Val 90 | Ala | Val | Gly | Asn | Glu Val 95 |
| Ser | Pro | Val | Gly 100 | Gly | Ser | Ser | Val | Ala 105 | Gln | Tyr | Val | Leu | Pro 110 | Ala |
| Ile | Gln | Asn 115 | Val | Tyr | Gln | Ala | Ile 120 | Arg | Ala | Gln | Gly | Leu 125 | His | Asp Gln |
| Ile | Lys | Val | Ser | Thr | Ser | Ile | Asp | Met | Thr | Leu | Ile | Gly | Asn | Ser Phe |

```
        130                          135                                140
Pro  Pro  Ser  Gln  Gly  Ser  Phe  Arg  Gly  Asp  Val  Arg  Ser  Tyr  Leu  Asp
145                      150                      155                      160

Pro  Ile  Ile  Gly  Tyr  Leu  Val  Tyr  Ala  Asn  Ala  Pro  Leu  Leu  Val  Asn
                    165                      170                     175

Val  Tyr  Pro  Tyr  Phe  Ser  Tyr  Thr  Gly  Asn  Pro  Arg  Asp  Ile  Ser  Leu
               180                           185                190

Pro  Tyr  Ala  Leu  Phe  Thr  Ala  Pro  Asn  Val  Val  Val  Trp  Asp  Gly  Gln
          195                      200                     205

Tyr  Gly  Tyr  Gln  Asn  Leu  Phe  Asp  Ala  Met  Leu  Asp  Ser  Val  His  Ala
     210                      215                     220

Ala  Ile  Asp  Asn  Thr  Lys  Ile  Gly  Tyr  Val  Glu  Val  Val  Val  Ser  Glu
225                      230                     235                          240

Ser  Gly  Trp  Pro  Ser  Asp  Gly  Gly  Phe  Ala  Ala  Thr  Tyr  Asp  Asn  Ala
                    245                     250                     255

Arg  Val  Tyr  Leu  Asp  Asn  Leu  Val  Arg  Arg  Ala  Asn  Arg  Gly  Ser  Pro
               260                      265                     270

Arg  Arg  Pro  Ser  Lys  Pro  Thr  Glu  Thr  Tyr  Ile  Phe  Ala  Met  Phe  Asp
          275                      280                     285

Glu  Asn  Gln  Lys  Asn  Pro  Glu  Ile  Glu  Lys  His  Phe  Gly  Leu  Phe  Asn
     290                      295                     300

Pro  Asn  Lys  Gln  Lys  Lys  Tyr  Pro  Phe  Gly  Phe  Gly  Gly  Lys  Arg  Leu
305                      310                     315                          320

Gly  Lys  Val  Val  Ile  Asp  Asp  Phe  Asn  Ala  Thr  Thr  Ser  Ile  Lys  Ser
                    325                     330                     335

Asp  Val
```

( 2 ) INFORMATION FOR SEQ ID NO:17:

( i ) SEQUENCE CHARACTERISTICS:
      ( A ) LENGTH: 1829 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i x ) FEATURE:
      ( A ) NAME/KEY: CDS
      ( B ) LOCATION: 438..1547

( i x ) FEATURE:
      ( A ) NAME/KEY: mat_peptide
      ( B ) LOCATION: 537..1547

( i x ) FEATURE:
      ( A ) NAME/KEY: sig_peptide
      ( B ) LOCATION: 438..536

( x i ) SEQUENCE DESCRIPTION: SEQ ID NO:17:

```
AAGCTTGCAC  GACACACTTG  TCTACTCCAA  AAATATCAAA  GATACAGTCC  TCAGAAGACC      60

AAAGGGCCAA  TTGAGACTTT  TCAACAAAGG  GTAATATCCG  GAAACCTCCT  CGGATTCCAT     120

TGCCCAGCTA  TCTGTCACTT  TATTGTGAAG  ATAGTGGAAA  AGGAAGGTGG  CTCCTACAAA     180

TGCCATCATT  GCGATAAAGG  AAAGGCCATC  GTTGAAGATG  CCTCTGCCGA  CAGTGGTCCC     240

AAAGATGGAC  CCCCACCCAC  GAGGAGCATC  GTGGAAAAAG  AAGACGTTCC  AACCACGTCT     300

TCAAAGCAAG  TGGATTGATG  TGATATCTCC  ACTGACGTAA  GGGATGACGC  ACAATCCCAC     360
```

| | | | | | | | | | | | | | | | |
|---|---|---|---|---|---|---|---|---|---|---|---|---|---|---|---|
| TATCCTTCGC | AAGACCCTTC | CTCTATATAA | GGAAGTTCAT | TTCATTTGGA | GAGAACACGG | | | | | | | | | | 420 |

GGGACTCTAG AGGATCC ATG CCT TCT CTC TTC GCT AGA AAC CAG AGG TTC    470
                        Met Pro Ser Leu Phe Ala Arg Asn Gln Arg Phe
                        -33            -30                      -25

TCA TTG GCT ACT CTC CTG CTT CTT CTG GAA CTA TTG ACA GGA AAC CTT    518
Ser Leu Ala Thr Leu Leu Leu Leu Leu Glu Leu Leu Thr Gly Asn Leu
        -20                  -15                        -10

CGC ATG GCA GAT GCT CAA ATT GGT GTG TGT TAT GGC ATG CTG GGC AAC    566
Arg Met Ala Asp Ala Gln Ile Gly Val Cys Tyr Gly Met Leu Gly Asn
    -5                      1                5                        10

AAT CTA CCG TCA GCA AAC GAT GTT ATA GGT CTT TAT AGA TCA AAT AAC    614
Asn Leu Pro Ser Ala Asn Asp Val Ile Gly Leu Tyr Arg Ser Asn Asn
                  15                        20                        25

ATA AAG AGA ATG AGA CTC TAT GAT CCT AAT CAA GCT GCT CTA GAA GCA    662
Ile Lys Arg Met Arg Leu Tyr Asp Pro Asn Gln Ala Ala Leu Glu Ala
              30                        35                        40

CTT AGA AAT TCT GGC ATT GAA CTC ATT CTT GGG GTG CCA AAC TCT GAC    710
Leu Arg Asn Ser Gly Ile Glu Leu Ile Leu Gly Val Pro Asn Ser Asp
              45                        50                        55

CTT CAA GGC CTT GCC ACC AAT CCT GAC ACT TCT CGT CAA TGG GTG CAA    758
Leu Gln Gly Leu Ala Thr Asn Pro Asp Thr Ser Arg Gln Trp Val Gln
        60                        65                        70

AAA AAC GTG TTG AAC TTT TGG CCT AGT GTC AAA ATC AAG TAC GTG GCA    806
Lys Asn Val Leu Asn Phe Trp Pro Ser Val Lys Ile Lys Tyr Val Ala
75                    80                        85                        90

GTT GGA AAT GAA GTG AGT CCC GTT GGA GGC TCT TCT TCG GTA GCC CAA    854
Val Gly Asn Glu Val Ser Pro Val Gly Gly Ser Ser Ser Val Ala Gln
                  95                        100                    105

TAT GTT CTA CCT GCC ATC CAA AAT GTA TAC CAA GCA ATA AGA GCA CAA    902
Tyr Val Leu Pro Ala Ile Gln Asn Val Tyr Gln Ala Ile Arg Ala Gln
              110                       115                  120

GGC CTT CAT GAT CAA ATC AAG GTT TCA ACA TCT ATT GAC ATG ACC CTA    950
Gly Leu His Asp Gln Ile Lys Val Ser Thr Ser Ile Asp Met Thr Leu
          125                       130                  135

ATA GGA AAC TCT TTC CCT CCA TCG CAA GGT TCC TTC AGG GGT GAT GTG    998
Ile Gly Asn Ser Phe Pro Pro Ser Gln Gly Ser Phe Arg Gly Asp Val
140                    145                        150

AGA TCA TAC CTA GAT CCC ATA ATT GGG TAC TTG GTA TAT GCA AAT GCA    1046
Arg Ser Tyr Leu Asp Pro Ile Ile Gly Tyr Leu Val Tyr Ala Asn Ala
155                    160                        165                  170

CCA TTA CTA GTC AAT GTG TAC CCT TAT TTT AGT TAC ACT GGT AAC CCC    1094
Pro Leu Leu Val Asn Val Tyr Pro Tyr Phe Ser Tyr Thr Gly Asn Pro
                  175                        180                    185

CGT GAC ATA TCA CTT CCC TAT GCT CTT TTC ACA GCA CCA AAT GTT GTG    1142
Arg Asp Ile Ser Leu Pro Tyr Ala Leu Phe Thr Ala Pro Asn Val Val
              190                       195                  200

GTA TGG GAT GGT CAA TAT GGG TAC CAA AAT TTG TTT GAT GCT ATG TTG    1190
Val Trp Asp Gly Gln Tyr Gly Tyr Gln Asn Leu Phe Asp Ala Met Leu
          205                       210                  215

GAT TCA GTA CAT GCA GCC ATT GAT AAC ACT AAG ATT GGT TAT GTG GAG    1238
Asp Ser Val His Ala Ala Ile Asp Asn Thr Lys Ile Gly Tyr Val Glu
        220                       225                    230

GTT GTT GTA TCC GAG AGT GGG TGG CCA TCA GAT GGA GGA TTT GCT GCC    1286
Val Val Val Ser Glu Ser Gly Trp Pro Ser Asp Gly Gly Phe Ala Ala
235                    240                        245                  250

ACT TAT GAC AAC GCA CGC GTG TAC TTA GAC AAT TTG GTT CGT CGT GCT    1334
Thr Tyr Asp Asn Ala Arg Val Tyr Leu Asp Asn Leu Val Arg Arg Ala
                255                        260                  265

AAT AGA GGA AGC CCA AGA AGG CCT TCG AAG CCC ACT GAG ACT TAT ATA    1382

|     |     |     |     |     |     |     |     |     |     |     |     |     |     |     |      |
| --- | --- | --- | --- | --- | --- | --- | --- | --- | --- | --- | --- | --- | --- | --- | ---- |
| Asn | Arg | Gly | Ser | Pro | Arg | Arg | Pro | Ser | Lys | Pro | Thr | Glu | Thr | Tyr | Ile  |
|     |     |     | 270 |     |     |     |     | 275 |     |     |     |     | 280 |     |      |
| TTT | GCC | ATG | TTC | GAT | GAA | AAT | CAA | AAA | AAT | CCA | GAG | ATA | GAG | AAA | CAT  | 1430 |
| Phe | Ala | Met | Phe | Asp | Glu | Asn | Gln | Lys | Asn | Pro | Glu | Ile | Glu | Lys | His  |
|     |     | 285 |     |     |     |     | 290 |     |     |     |     | 295 |     |     |      |
| TTT | GGG | CTC | TTC | AAT | CCC | AAC | AAA | CAA | AAA | AAA | TAC | CCA | TTT | GGG | TTT  | 1478 |
| Phe | Gly | Leu | Phe | Asn | Pro | Asn | Lys | Gln | Lys | Lys | Tyr | Pro | Phe | Gly | Phe  |
|     | 300 |     |     |     |     | 305 |     |     |     |     | 310 |     |     |     |      |
| GGA | GGA | AAG | AGG | CTA | GGG | AAA | GTT | GTT | ATT | GAC | GAC | TTC | AAT | GCA | ACA  | 1526 |
| Gly | Gly | Lys | Arg | Leu | Gly | Lys | Val | Val | Ile | Asp | Asp | Phe | Asn | Ala | Thr  |
| 315 |     |     |     |     | 320 |     |     |     |     | 325 |     |     |     |     | 330  |
| ACT | TCC | ATT | AAG | AGT | GAT | GTG | TAAGGTTGAG | CTCGAATTTC | CCCGATCGTT |||||| 1577 |
| Thr | Ser | Ile | Lys | Ser | Asp | Val |     |     |     |     |     |     |     |     |      |
|     |     |     |     | 335 |     |     |     |     |     |     |     |     |     |     |      |

```
CAAACATTTG  GCAATAAAGT  TTCTTAAGAT  TGAATCCTGT  TGCCGGTCTT  GCGATGATTA      1637

TCATATAATT  TCTGTTGAAT  TACGTTAAGC  ATGTAATAAT  TAACATGTAA  TGCATGACGT      1697

TATTTATGAG  ATGGGTTTTT  ATGATTAGAG  TCCCGCAATT  ATACATTTAA  TACGCGATAG      1757

AAAACAAAAT  ATAGCGCGCA  AACTAGGATA  AATTATCGCG  CGCGGTGTCA  TCTATGTTAC      1817

TAGATCGAAT  TC                                                              1829
```

( 2 ) INFORMATION FOR SEQ ID NO:18:

( i ) SEQUENCE CHARACTERISTICS:
           ( A ) LENGTH: 370 amino acids
           ( B ) TYPE: amino acid
           ( D ) TOPOLOGY: linear ( i i ) MOLECULE TYPE: protein ( x i ) SEQUENCE DESCRIPTION: SEQ ID NO:18:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Pro | Ser | Leu | Phe | Ala | Arg | Asn | Gln | Arg | Phe | Ser | Leu | Ala | Thr | Leu |
| -33 |     |     | -30 |     |     |     | -25 |     |     |     | -20 |     |     |     |     |
| Leu | Leu | Leu | Leu | Glu | Leu | Leu | Thr | Gly | Asn | Leu | Arg | Met | Ala | Asp | Ala |
|     |     | -15 |     |     |     | -10 |     |     |     |     | -5  |     |     |     |     |
| Gln | Ile | Gly | Val | Cys | Tyr | Gly | Met | Leu | Gly | Asn | Asn | Leu | Pro | Ser | Ala |
|     | 1   |     |     |     | 5   |     |     |     |     | 10  |     |     |     |     | 15  |
| Asn | Asp | Val | Ile | Gly | Leu | Tyr | Arg | Ser | Asn | Asn | Ile | Lys | Arg | Met | Arg |
|     |     |     | 20  |     |     |     |     | 25  |     |     |     |     | 30  |     |     |
| Leu | Tyr | Asp | Pro | Asn | Gln | Ala | Ala | Leu | Glu | Ala | Leu | Arg | Asn | Ser | Gly |
|     |     |     | 35  |     |     |     | 40  |     |     |     |     | 45  |     |     |     |
| Ile | Glu | Leu | Ile | Leu | Gly | Val | Pro | Asn | Ser | Asp | Leu | Gln | Gly | Leu | Ala |
|     |     | 50  |     |     |     |     | 55  |     |     |     |     | 60  |     |     |     |
| Thr | Asn | Pro | Asp | Thr | Ser | Arg | Gln | Trp | Val | Gln | Lys | Asn | Val | Leu | Asn |
|     | 65  |     |     |     |     | 70  |     |     |     |     | 75  |     |     |     |     |
| Phe | Trp | Pro | Ser | Val | Lys | Ile | Lys | Tyr | Val | Ala | Val | Gly | Asn | Glu | Val |
| 80  |     |     |     |     | 85  |     |     |     |     | 90  |     |     |     |     | 95  |
| Ser | Pro | Val | Gly | Gly | Ser | Ser | Ser | Val | Ala | Gln | Tyr | Val | Leu | Pro | Ala |
|     |     |     |     | 100 |     |     |     |     | 105 |     |     |     |     | 110 |     |
| Ile | Gln | Asn | Val | Tyr | Gln | Ala | Ile | Arg | Ala | Gln | Gly | Leu | His | Asp | Gln |
|     |     |     | 115 |     |     |     |     | 120 |     |     |     |     | 125 |     |     |
| Ile | Lys | Val | Ser | Thr | Ser | Ile | Asp | Met | Thr | Leu | Ile | Gly | Asn | Ser | Phe |
|     |     |     | 130 |     |     |     |     | 135 |     |     |     |     | 140 |     |     |
| Pro | Pro | Ser | Gln | Gly | Ser | Phe | Arg | Gly | Asp | Val | Arg | Ser | Tyr | Leu | Asp |
|     |     |     | 145 |     |     |     |     | 150 |     |     |     |     | 155 |     |     |
| Pro | Ile | Ile | Gly | Tyr | Leu | Val | Tyr | Ala | Asn | Ala | Pro | Leu | Leu | Val | Asn |
| 160 |     |     |     |     | 165 |     |     |     |     | 170 |     |     |     |     | 175 |

| | | | | | | | | | | | | | | |
|---|---|---|---|---|---|---|---|---|---|---|---|---|---|---|
| Val | Tyr | Pro | Tyr | Phe | Ser | Tyr | Thr | Gly | Asn | Pro | Arg | Asp | Ile | Ser | Leu |
| | | | | 180 | | | | | 185 | | | | | 190 | |
| Pro | Tyr | Ala | Leu | Phe | Thr | Ala | Pro | Asn | Val | Val | Val | Trp | Asp | Gly | Gln |
| | | | 195 | | | | | 200 | | | | 205 | | | |
| Tyr | Gly | Tyr | Gln | Asn | Leu | Phe | Asp | Ala | Met | Leu | Asp | Ser | Val | His | Ala |
| | | 210 | | | | | 215 | | | | 220 | | | | |
| Ala | Ile | Asp | Asn | Thr | Lys | Ile | Gly | Tyr | Val | Glu | Val | Val | Ser | Glu | |
| | 225 | | | | | 230 | | | | 235 | | | | | |
| Ser | Gly | Trp | Pro | Ser | Asp | Gly | Gly | Phe | Ala | Ala | Thr | Tyr | Asp | Asn | Ala |
| 240 | | | | | 245 | | | | 250 | | | | | 255 | |
| Arg | Val | Tyr | Leu | Asp | Asn | Leu | Val | Arg | Arg | Ala | Asn | Arg | Gly | Ser | Pro |
| | | | 260 | | | | | 265 | | | | | 270 | | |
| Arg | Arg | Pro | Ser | Lys | Pro | Thr | Glu | Thr | Tyr | Ile | Phe | Ala | Met | Phe | Asp |
| | | | 275 | | | | 280 | | | | | 285 | | | |
| Glu | Asn | Gln | Lys | Asn | Pro | Glu | Ile | Glu | Lys | His | Phe | Gly | Leu | Phe | Asn |
| | | 290 | | | | | 295 | | | | | 300 | | | |
| Pro | Asn | Lys | Gln | Lys | Lys | Tyr | Pro | Phe | Gly | Phe | Gly | Gly | Lys | Arg | Leu |
| | 305 | | | | | | 310 | | | | | 315 | | | |
| Gly | Lys | Val | Val | Ile | Asp | Asp | Phe | Asn | Ala | Thr | Thr | Ser | Ile | Lys | Ser |
| 320 | | | | 325 | | | | | 330 | | | | | 335 | |
| Asp | Val | | | | | | | | | | | | | | |

( 2 ) INFORMATION FOR SEQ ID NO:19:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:19:

GATCATGAAG GCCTTGTGCT CTTATTGCTT GG        32

( 2 ) INFORMATION FOR SEQ ID NO:20:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:20:

GAGAAGGCAT GGATCCAAAC ATATGAATAC ACCAC        35

( 2 ) INFORMATION FOR SEQ ID NO:21:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:21:

CAGAGATTTT GAAGCTTAGG AGCTCAACCT TACACATC            38

( 2 ) INFORMATION FOR SEQ ID NO:22:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:22:

TATGATTGGT GTGTGTTATG GCATGACTAA CCACACACAA TACC            44

( 2 ) INFORMATION FOR SEQ ID NO:23:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

Met Ile Gly Val Xaa Tyr Gly Met Leu
  1               5

( 2 ) INFORMATION FOR SEQ ID NO:24:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

Met Ile Gly Val Xaa Tyr Gly Met Leu Gly Asn Asn Leu Pro
  1               5                   10

( 2 ) INFORMATION FOR SEQ ID NO:25:

( i ) SEQUENCE CHARACTERISTICS:
        ( A ) LENGTH: 337 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

Ile Gly Val Cys Tyr Gly Met Leu Gly Asn Asn Leu Pro Ser Ala Asn
1               5                   10                  15

Asp Val Ile Gly Leu Tyr Arg Ser Asn Asn Ile Lys Arg Met Arg Leu
                20                  25                  30

Tyr Asp Pro Asn Gln Ala Ala Leu Glu Ala Leu Arg Asn Ser Gly Ile
            35                  40                  45

Glu Leu Ile Leu Gly Val Pro Asn Ser Asp Leu Gln Gly Leu Ala Thr
        50                  55                  60

Asn Pro Asp Thr Ser Arg Gln Trp Val Gln Lys Asn Val Leu Asn Phe
65                  70                  75                  80

-continued

| | | | | | | | | | | | | | |
|---|---|---|---|---|---|---|---|---|---|---|---|---|---|
|Trp|Pro|Ser|Val|Lys 85|Ile|Lys|Tyr|Val|Ala 90|Val|Gly|Asn|Glu|Val|Ser 95|
|Pro|Val|Gly|Gly 100|Ser|Ser|Ser|Val|Ala 105|Gln|Tyr|Val|Leu|Pro 110|Ala|Ile|
|Gln|Asn|Val 115|Tyr|Gln|Ala|Ile|Arg 120|Ala|Gln|Gly|Leu|His 125|Asp|Gln|Ile|
|Lys|Val 130|Ser|Thr|Ser|Ile|Asp 135|Met|Thr|Leu|Ile|Gly 140|Asn|Ser|Phe|Pro|
|Pro 145|Ser|Gln|Gly|Ser|Phe 150|Arg|Gly|Asp|Val|Arg 155|Ser|Tyr|Leu|Asp|Pro 160|
|Ile|Ile|Gly|Tyr|Leu 165|Val|Tyr|Ala|Asn|Ala 170|Pro|Leu|Leu|Val|Asn 175|Val|
|Tyr|Pro|Tyr|Phe 180|Ser|Tyr|Thr|Gly|Asn 185|Pro|Arg|Asp|Ile|Ser 190|Leu|Pro|
|Tyr|Ala|Leu 195|Phe|Thr|Ala|Pro|Asn 200|Val|Val|Val|Trp|Asp 205|Gly|Gln|Tyr|
|Gly|Tyr 210|Gln|Asn|Leu|Phe|Asp 215|Ala|Met|Leu|Asp|Ser 220|Val|His|Ala|Ala|
|Ile 225|Asp|Asn|Thr|Lys|Ile 230|Gly|Tyr|Val|Glu|Val 235|Val|Val|Ser|Glu|Ser 240|
|Gly|Trp|Pro|Ser|Asp 245|Gly|Gly|Phe|Ala|Ala 250|Thr|Tyr|Asp|Asn|Ala 255|Arg|
|Val|Tyr|Leu|Asp 260|Asn|Leu|Val|Arg|Arg 265|Ala|Asn|Arg|Gly|Ser 270|Pro|Arg|
|Arg|Pro|Ser 275|Lys|Pro|Thr|Glu|Thr 280|Tyr|Ile|Phe|Ala|Met 285|Phe|Asp|Glu|
|Asn|Gln 290|Lys|Asn|Pro|Glu|Ile 295|Glu|Lys|His|Phe|Gly 300|Leu|Phe|Asn|Pro|
|Asn 305|Lys|Gln|Lys|Lys|Tyr 310|Pro|Phe|Gly|Phe|Gly 315|Gly|Lys|Arg|Leu|Gly 320|
|Lys|Val|Val|Ile|Asp 325|Asp|Phe|Asn|Ala|Thr 330|Thr|Ser|Ile|Lys|Ser 335|Asp|
|Val|

( 2 ) INFORMATION FOR SEQ ID NO:26:

( i ) SEQUENCE CHARACTERISTICS:
        ( A ) LENGTH: 370 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

| | | | | | | | | | | | | | | | |
|---|---|---|---|---|---|---|---|---|---|---|---|---|---|---|---|
|Met 1|Asp|Thr|Ser|His 5|Lys|His|Ile|Ala|Leu 10|Gln|Met|Ala|Ala|Ile 15|Ile|
|Leu|Leu|Gly|Leu 20|Leu|Val|Ser|Ser|Thr 25|Glu|Ile|Val|Gly|Ala 30|Gln|Ser|
|Val|Gly|Val 35|Cys|Tyr|Gly|Met|Leu 40|Gly|Asn|Asn|Leu|Pro 45|Pro|Ala|Ser|
|Gln|Val 50|Val|Gln|Leu|Tyr|Lys 55|Ser|Lys|Asn|Ile|Arg 60|Arg|Met|Arg|Leu|
|Tyr 65|Asp|Pro|Asn|Gln|Ala 70|Ala|Leu|Gln|Ala|Leu 75|Arg|Gly|Ser|Asn|Ile 80|
|Glu|Val|Met|Leu|Gly 85|Val|Pro|Asn|Ser|Asp 90|Leu|Gln|Asn|Ile|Ala 95|Ala|

| | | | | | | | | | | | | | | |
|---|---|---|---|---|---|---|---|---|---|---|---|---|---|---|
| Asn | Pro | Ser | Asn 100 | Ala | Asn | Asn | Trp | Val 105 | Gln | Arg | Asn | Val | Arg 110 | Asn | Phe |
| Trp | Pro | Ala 115 | Val | Lys | Phe | Arg | Tyr 120 | Ile | Ala | Val | Gly | Asn 125 | Glu | Val | Ser |
| Pro | Val 130 | Thr | Gly | Thr | Ser | Ser 135 | Leu | Thr | Arg | Tyr | Leu 140 | Leu | Pro | Ala | Met |
| Arg 145 | Asn | Ile | Arg | Asn | Ala 150 | Ile | Ser | Ser | Ala | Gly 155 | Leu | Gln | Asn | Asn | Ile 160 |
| Lys | Val | Ser | Ser | Ser 165 | Val | Asp | Met | Thr | Leu 170 | Ile | Gly | Asn | Ser | Phe 175 | Pro |
| Pro | Ser | Gln | Gly 180 | Ser | Phe | Arg | Asn | Asp 185 | Val | Arg | Ser | Phe | Ile 190 | Asp | Pro |
| Ile | Ile | Gly 195 | Phe | Val | Arg | Arg | Ile 200 | Asn | Ser | Pro | Leu | Leu 205 | Val | Asn | Ile |
| Tyr | Pro 210 | Tyr | Phe | Ser | Tyr | Ala 215 | Gly | Asn | Pro | Arg | Asp 220 | Ile | Ser | Leu | Pro |
| Tyr 225 | Ala | Leu | Phe | Thr | Ala 230 | Pro | Asn | Val | Val | Val 235 | Gln | Asp | Gly | Ser | Leu 240 |
| Gly | Tyr | Arg | Asn | Leu 245 | Phe | Asp | Ala | Met | Ser 250 | Asp | Ala | Val | Tyr | Ala 255 | Ala |
| Leu | Ser | Arg | Ala 260 | Gly | Gly | Gly | Ser | Ile 265 | Glu | Ile | Val | Val | Ser 270 | Glu | Ser |
| Gly | Trp | Pro 275 | Ser | Ala | Gly | Ala | Phe 280 | Ala | Ala | Thr | Thr | Asn 285 | Asn | Ala | Ala |
| Thr | Tyr 290 | Tyr | Lys | Asn | Leu | Ile 295 | Gln | His | Val | Lys | Arg 300 | Gly | Ser | Pro | Arg |
| Arg 305 | Pro | Asn | Lys | Val | Ile 310 | Glu | Thr | Tyr | Leu | Phe 315 | Ala | Met | Phe | Asp | Glu 320 |
| Asn | Asn | Lys | Asn | Pro 325 | Glu | Leu | Glu | Lys | His 330 | Phe | Gly | Leu | Phe | Ser 335 | Pro |
| Asn | Lys | Gln | Pro 340 | Lys | Tyr | Pro | Leu | Ser 345 | Phe | Gly | Phe | Ser | Asp 350 | Arg | Tyr |
| Trp | Asp | Ile 355 | Ser | Ala | Glu | Asn | Asn 360 | Ala | Thr | Ala | Ala | Ser 365 | Leu | Ile | Ser |
| Glu | Met 370 | | | | | | | | | | | | | | |

We claim

1. A DNA construct, which codes for a protein having β-1,3-glucanase activity, wherein said protein comprises the following sequence ($a_1$) (SEQ ID NO. 1)

Ile Gly Val Cys Tyr Gly Met Leu Gly Asn Asn
Leu Pro Ser Ala Asn Asp Val Ile Gly Leu Tyr
Arg Ser Asn Asn Ile Lys Arg Met Arg Leu Tyr
Asp Pro Asn Gln Ala Ala Leu Glu Ala Leu Arg
Asn Ser Gly Ile Glu Leu Ile Leu Gly Val Pro
Asn Ser Asp Leu Gln Gly Leu Ala Thr Asn Pro
Asp Thr Ser Arg Gln Trp Val Gln Lys Asn Val
Leu Asn Phe Trp Pro Ser Val Lys Ile Lys Tyr
Val Ala Val Gly Asn Glu Val Ser Pro Val Gly
Gly Ser Ser Ser Val Ala Gln Tyr Val Leu Pro
Ala Ile Gln Asn Val Tyr Gln Ala Ile Arg Ala
Gln Gly Leu His Asp Gln Ile Lys Val Ser Thr
Ser Ile Asp Met Thr Leu Ile Gly Asn Ser Phe
Pro Pro Ser Gln Gly Ser Phe Arg Gly Asp Val
Arg Ser Tyr Leu Asp Pro Ile Ile Gly Tyr Leu
Val Tyr Ala Asn Ala Pro Leu Leu Val Asn Val
Tyr Pro Tyr Phe Ser Tyr Thr Gly Asn Pro Arg
Asp Ile Ser Leu Pro Tyr Ala Leu Phe Thr Ala
Pro Asn Val Val Val Trp Asp Gly Gln Tyr Gly
Tyr Gln Asn Leu Phe Asp Ala Met Leu Asp Ser
Val His Ala Ala Ile Asp Asn Thr Lys Ile Gly
Tyr Val Glu Val Val Val Ser Glu Ser Gly Trp
Pro Ser Asp Gly Gly Phe Ala Ala Thr Tyr Asp
Asn Ala Arg Val Tyr Leu Asp Asn Leu Val Arg
Arg Ala Asn Arg Gly Ser Pro Arg Arg Pro Ser
Lys Pro Thr Glu Thr Tyr Ile Phe Ala Met Phe
Asp Glu Asn Gln Lys Asn Pro Glu Ile Glu Lys
His Phe Gly Leu Phe Asn Pro Asn Lys Gln Lys Lys.

2. A DNA construct according to claim 1, further comprising immediately downstream of the nucleotide sequence coding for the amino acid sequence ($a_1$) (SEQ ID NO. 1), the nucleotide sequence coding for the amino acid sequence ($a_4$) (SEQ ID NO. 2) below:

Tyr Pro Phe Gly Phe Gly Gly Lys Arg Leu Gly Lys
Val Val Ile Asp Asp Phe Asn Ala Thr Thr Ser Ile Lys Ser
Asp Val truncated in its carboxy-terminal portion by 0 to 27 amino acids.

3. A DNA construct according to claim 2, further comprising immediately upstream of the nucleotide sequence coding for the amino acid sequence ($a_1$) (SEQ ID NO. 1), a codon for Gln.

4. A DNA construct according to claim 3, which codes for a protein having β-1,3-glucanase activity, which comprises the following sequence ($a_5$) (SEQ ID NO. 3)

Gln Ile Gly Val Cys Tyr Gly Met Leu Gly Asn
Asn Leu Pro Ser Ala Asn Asp Val Ile Gly Leu
Tyr Arg Ser Asn Asn Ile Lys Arg Met Arg Leu
Tyr Asp Pro Asn Gln Ala Ala Leu Glu Ala Leu
Arg Asn Ser Gly Ile Glu Leu Ile Leu Gly Val
Pro Asn Ser Asp Leu Gln Gly Leu Ala Thr Asn
Pro Asp Thr Ser Arg Gln Trp Val Gln Lys Asn
Val Leu Asn Phe Trp Pro Ser Val Lys Ile Lys
Tyr Val Ala Val Gly Asn Glu Val Ser Pro Val
Gly Gly Ser Ser Ser Val Ala Gln Tyr Val Leu
Pro Ala Ile Gln Asn Val Tyr Gln Ala Ile Arg
Ala Gln Gly Leu His Asp Gln Ile Lys Val Ser
Thr Ser Ile Asp Met Thr Leu Ile Gly Asn Ser
Phe Pro Pro Ser Gln Gly Ser Phe Arg Gly Asp
Val Arg Ser Tyr Leu Asp Pro Ile Ile Gly Tyr
Leu Val Tyr Ala Asn Ala Pro Leu Leu Val Asn
Val Tyr Pro Tyr Phe Ser Tyr Thr Gly Asn Pro
Arg Asp Ile Ser Leu Pro Tyr Ala Leu Phe Thr
Ala Pro Asn Val Val Val Trp Asp Gly Gln Tyr
Gly Tyr Gln Asn Leu Phe Asp Ala Met Leu Asp
Ser Val His Ala Ala Ile Asp Asn Thr Lys Ile
Gly Tyr Val Glu Val Val Val Ser Glu Ser Gly

-continued
Trp Pro Ser Asp Gly Gly Phe Ala Ala Thr Tyr

-continued
Asp Asn Ala Arg Val Tyr Leu Asp Asn Leu Val
Arg Arg Ala Asn Arg Gly Ser Pro Arg Arg Pro
Ser Lys Pro Thr Glu Thr Tyr Ile Phe Ala Met
Phe Asp Glu Asn Gln Lys Asn Pro Glu Ile Glu
Lys His Phe Gly Leu Phe Asn Pro Asn Lys Gln
Lys Lys Tyr Pro Phe Gly Phe Gly Gly Lys Arg
Leu Gly Lys Val Val Ile Asp Asp Phe Asn Ala
Thr Thr Ser Ile Lys Ser Asp Val.

5. A DNA construct according to claim 3 which contains, upstream of said codon for Gln preceding the nucleotide sequence coding for the amino acid sequence ($a_1$) (SEQ ID NO. 1), a region encoding a signal sequence.

6. A DNA construct according to claim 5, wherein said region encoding a signal sequence encodes a signal peptide of the following sequence ($a_2$) (SEQ ID NO. 7)

Met Pro Ser Leu Phe Ala Arg Asn Gln Arg Phe Ser Leu Ala
Thr Leu Leu Leu Leu Leu Glu Leu Leu Thr Gly Asn Leu Arg
Met Ala Asp Ala.

7. A DNA construct according to claim 1, wherein the nucleotide sequence coding for the amino acid sequence ($a_1$) (SEQ ID NO. 1) is the following sequence ($Na_1$) (SEQ ID NO. 8)

ATTGGTGTGT GTTATGGCAT GCTGGGCAAC AATCTACCGT CAGCAAACGA
TGTTATAGGT CTTTATAGAT CAAATAACAT AAAGAGAATG AGACTCTATG
ATCCTAATCA AGCTGCTCTA GAAGCACTTA GAAATTCTGG CATTGAACTC
ATTCTTGGGG TGCCAAACTC TGACCTTCAA GGCCTTGCCA CCAATCCTGA
CACTTCTCGT CAATGGGTGC AAAAAAACGT GTTGAACTTT TGGCCTAGTG
TCAAAATCAA GTACGTGGCA GTTGGAAATG AAGTGAGTCC CGTTGGAGGC
TCTTCTTCGG TAGCCCAATA TGTTCTACCT GCCATCCAAA ATGTATACCA
AGCAATAAGA GCTCAAGGCC TTCATGATCA AATCAAGGTT TCAACATCTA
TTGACATGAC CCTAATAGGA AACTCTTTCC CTCCATCGCA AGGTTCCTTC
AGGGGTGATG TGAGATCATA CCTAGATCCC ATAATTGGGT ACTTGGTATA
TGCAAATGCA CCATTACTAG TCAATGTGTA CCCTTATTTT AGTTACACTG
GTAACCCCCG TGACATATCA CTTCCCTATG CTCTTTTCAC AGCACCAAAT
GTTGTGGTAT GGGATGGTCA ATATGGGTAC CAAAATTTGT TTGATGCTAT
GTTGGATTCA GTACATGCAG CCATTGATAA CACTAAGATT GGTTATGTGG
AGGTTGTTGT ATCCGAGAGT GGGTGGCCAT CAGATGGAGG ATTTGCTGCC
ACTTATGACA ACGCACGCGT GTACTTAGAC AATTTGGTTC GTCGTGCTAA
TAGAGGAAGC CCAAGAAGGC CTTCGAAGCC CACTGAGACT TATATATTTG
CCATGTTCGA TGAAAATCAA AAAAATCCAG AGATAGAGAA ACATTTTGGG
CTCTTCAATC CCAACAAACA AAAAAAA.

8. A DNA construct according to claim 6, wherein the nucleotide sequence coding for the amino acid sequence ($a_2$) (SEQ ID NO. 7) is the following sequence ($Na_2$) (SEQ ID NO. 9)

ATGCCTTCTC TCTTCGCTAG AAACCAGAGG TTCTCATTGG CTACTCTCCT
GCTTCTTCTG GAACTATTGA CAGGAAACCT TCGCATGGCA GATGCT.

9. A DNA construct according to claim 2 wherein the nucleotide sequence coding for the amino acid sequence (a₄) (SEQ ID NO. 2) is the following sequence (Na₄) (SEQ ID NO. 10)

TACCCATTTG GGTTTGGAGG AAAGAGGCTA GGGAAAGTTG TTATTGACGA
CTTCAATGCA ACAACTTCCA TTAAGAGTGA TGTG.

10. A bacterium which contains a DNA construct according to claim 1 operably linked to cis-acting signals effective for its replication and its expression in said bacterium.

11. A plant cell transformed with a DNA construct according to claim 1 operably linked to cis-acting signals effective for its expression in said cell.

12. A plant cell according to claim 11, which belongs to a species selected from the group consisting of *Nicotiana tabacum, Helianthus annuus* and *Brassica napus*.

13. A plant or plant part, which plant or plant part contains a DNA construct according to claim 1 operably linked to cis-acting signals effective for its expression in said plant or plant part.

14. A plant or plant part according to claim 13, which plant or plant part belongs to a species selected from the group consisting of *Nicotiana tabacum, Helianthus annuus* and *Brassica napus*.

15. A plant part according to claim 13, which is capable of forming a complete new plant or of producing seeds.

16. A plant part according to claim 15, which is a seed.

17. An isolated, purified protein having β-1,3-glucanase activity, which comprises a region having the amino acid sequence (a₁) (SEQ ID NO. 1)

Ile Gly Val Cys Tyr Gly Met Leu Gly Asn Asn Leu Pro Ser
Ala Asn Asp Val Ile Gly Leu Tyr Arg Ser Asn Asn Ile Lys
Arg Met Arg Leu Tyr Asp Pro Asn Gln Ala Ala Leu Glu Ala
Leu Arg Asn Ser Gly Ile Glu Leu Ile Leu Gly Val Pro Asn
Ser Asp Leu Gln Gly Leu Ala Thr Asn Pro Asp Thr Ser Arg
Gln Trp Val Gln Lys Asn Val Leu Asn Phe Trp Pro Ser Val
Lys Ile Lys Tyr Val Ala Val Gly Asn Glu Val Ser Pro Val
Gly Gly Ser Ser Ser Val Ala Gln Tyr Val Leu Pro Ala Ile
Gln Asn Val Tyr Gln Ala Ile Arg Ala Gln Gly Leu His Asp
Gln Ile Val Ser Thr Ser Ile Asp Met Thr Leu Ile Gly
Asn Ser Phe Pro Pro Ser Gln Gly Ser Phe Arg Gly Asp Val
Arg Ser Tyr Leu Asp Pro Ile Ile Gly Tyr Leu Val Tyr Ala
Asn Ala Pro Leu Leu Val Asn Val Tyr Pro Tyr Phe Ser Tyr
Thr Gly Asn Pro Arg Asp Ile Ser Leu Pro Tyr Ala Leu Phe
Thr Ala Pro Asn Val Val Val Trp Asp Gly Gln Tyr Gly Tyr
Gln Asn Leu Phe Asp Ala Met Leu Asp Ser Val His Ala Ala
Ile Asp Asn Thr Lys Ile Gly Tyr Val Glu Val Val Val Ser
Glu Ser Gly Trp Pro Ser Asp Gly Gly Phe Ala Ala Thr Tyr
Asp Asn Ala Arg Val Tyr Asp Asn Leu Val Arg Arg Ala
Asn Arg Gly Ser Pro Arg Arg Pro Ser Lys Pro Thr Glu Thr
Tyr Ile Phe Ala Met Phe Asp Glu Asn Gln Lys Asn Pro Glu
Ile Glu Lys His Phe Gly Leu Phe Asn Pro Asn Lys Gln Lys
Lys.

18. An isolated, purified protein according to claim 17, further comprising immediately downstream of the sequence (a₁) (SEQ ID NO. 1), a region having the amino acid sequence (a₄) (SEQ ID NO. 2)

Tyr Pro Phe Gly Phe Gly Gly Lys Arg Leu Gly Lys
Val Val Ile Asp Asp Phe Asn Ala Thr Thr Ser Ile Lys Ser
Asp Val.

truncated in its carboxy-terminal portion by 0 to 27 amino acids.

19. An isolated, purified protein having β-1,3-glucanase activity, comprising a region having the amino acid sequence (a₅) (SEQ ID NO. 3)

Gln Ile Gly Val Cys Tyr Gly Met Leu Gly Asn Asn Leu Pro
Ser Ala Asn Asp Val Ile Gly Leu Tyr Arg Ser Asn Asn Ile
Lys Arg Met Arg Leu Tyr Asp Pro Asn Gln Ala Ala Leu Glu
Ala Leu Arg Asn Ser Gly Ile Glu Leu Ile Leu Gly Val Pro
Asn Ser Asp Leu Gln Gly Leu Ala Thr Asn Pro Asp Thr Ser
Arg Gln Trp Val Gln Lys Asn Val Leu Asn Phe Trp Pro Ser
Val Lys Ile Lys Tyr Val Ala Val Gly Asn Glu Val Ser Pro
Val Gly Gly Ser Ser Ser Val Ala Gln Tyr Val Leu Pro Ala
Ile Gln Asn Val Tyr Gln Ala Ile Arg Ala Gly Gly Leu His
Asp Gln Ile Lys Val Ser Thr Ser Ile Asp Met Thr Leu Ile
Gly Asn Ser Phe Pro Pro Ser Gln Gly Ser Phe Arg Gly Asp
Val Arg Ser Tyr Leu Asp Pro Ile Ile Gly Tyr Leu Val Tyr
Ala Asn Ala Pro Leu Leu Val Asn Val Tyr Pro Tyr Phe Ser
Tyr Thr Gly Asn Pro Arg Asp Ile Ser Leu Pro Tyr Ala Leu
Phe Thr Ala Pro Asn Val Val Val Trp Asp Gly Gln Tyr Gly
Tyr Gln Asn Leu Phe Asp Ala Met Leu Asp Ser Val His Ala
Ala Ile Asp Asn Thr Lys Ile Gly Tyr Val Glu Val Val Val
Ser Glu Ser Gly Trp Pro Ser Asp Gly Gly Phe Ala Ala Thr
Tyr Asp Asn Ala Arg Val Tyr Leu Asp Asn Leu Val Arg Arg
Ala Asn Arg Gly Ser Pro Arg Arg Pro Ser Lys Pro Thr Glu
Thr Tyr Ile Phe Ala Met Phe Asp Glu Asn Gln Lys Asn Pro
Glu Ile Glu Lys His Phe Gly Leu Phe Asn Pro Asn Lys Gln
Lys Lys Tyr Pro Phe Gly Phe Gly Gly Lys Arg Leu Gly Lys
Val Val Ile Asp Asp Phe Asn Ala Thr Thr Ser Ile Lys Ser
Asp Val.

20. An isolated, purified protein according to claim 17, which possesses an apparent molecular mass of 36±3 kDa.

21. An isolated, purified protein according to claim 17, which possesses an apparent molecular mass of 37±3 kDa.

22. An isolated, purified protein according to claim 17, which possesses an apparent molecular mass of 39±3 kDa.

23. A method for preparing a protein according to claim 17, which comprises culturing a bacterium of claim 10.

24. A method for preparing a protein according to claim 17, which comprises culturing a plant cell of claim 11.

25. A method for preparing a protein according to claim 17, which comprises culturing a plant or plant part of claim 13.

* * * * *